(12) United States Patent
Zheng et al.

(10) Patent No.: US 8,354,400 B2
(45) Date of Patent: Jan. 15, 2013

(54) BENZOXAZOLE COMPOUNDS AND METHODS OF USE

(75) Inventors: Wanjun Zheng, Londonderry, NH (US); Mark Spyvee, Hampstead, NY (US); Fabian Gusovsky, Andover, MA (US); Sally T. Ishizaka, Weston, MA (US)

(73) Assignee: Eisai R&D Co., Ltd. (JP)

( * ) Notice: Subject to any disclaimer, the term of this patent is extended or adjusted under 35 U.S.C. 154(b) by 94 days.

(21) Appl. No.: 13/121,012

(22) PCT Filed: Sep. 25, 2009

(86) PCT No.: PCT/US2009/058398
§ 371 (c)(1),
(2), (4) Date: Apr. 12, 2011

(87) PCT Pub. No.: WO2010/036905
PCT Pub. Date: Apr. 1, 2010

(65) Prior Publication Data
US 2011/0183967 A1    Jul. 28, 2011

Related U.S. Application Data

(60) Provisional application No. 61/100,678, filed on Sep. 26, 2008.

(51) Int. Cl.
| | |
|---|---|
| *A61K 31/551* | (2006.01) |
| *A61K 31/5355* | (2006.01) |
| *A61K 31/496* | (2006.01) |
| *A61K 31/4402* | (2006.01) |
| *A61K 31/4409* | (2006.01) |
| *A61K 31/443* | (2006.01) |
| *A61K 31/4453* | (2006.01) |
| *A61K 31/4468* | (2006.01) |
| *A61K 31/428* | (2006.01) |

(52) U.S. Cl. ............... 514/218; 514/232.5; 514/252.11; 514/316; 514/333; 514/375; 540/575; 544/137; 544/357; 546/187; 546/256; 548/224

(58) Field of Classification Search ................ None
See application file for complete search history.

(56) References Cited

FOREIGN PATENT DOCUMENTS

| WO | WO 02/051821 A1 | 7/2002 |
|---|---|---|
| WO | WO 03/004023 A1 | 1/2003 |
| WO | WO 03/050095 A1 | 6/2003 |
| WO | WO 2005/044807 A2 | 5/2005 |
| WO | WO 2006/026316 A2 | 3/2006 |
| WO | WO 2007/064773 A2 | 6/2007 |

OTHER PUBLICATIONS

Notification Concerning Transmittal of International Preliminary Report on Patentability (Chapter I of The Patent Cooperation Treaty) corresponding to International Application No. PCT/US2009/058398 mailed Apr. 7, 2011.
Evans et al. "Synthesis of a group of 1*H*-benzimidazoles and their screening for anti-inflammatory activity", *Eur. J. Med. Chem.* 31:635-642 (1996).
Notification of Transmittal of the International Search Report and the Written Opinion of the International Searching Authority, or the Declaration corresponding to International Application No. PCT/US2009/058398 mailed Nov. 27, 2009.

*Primary Examiner* — Joseph K. McKane
*Assistant Examiner* — Alicia L Otton
(74) *Attorney, Agent, or Firm* — Myers Bigel Sibley & Sajovec, PA

(57) ABSTRACT

The present invention provides benzoxazole compounds and pharmaceutically acceptable salts thereof and pharmaceutical compositions including the same. The present invention further provides methods of use as described herein.

21 Claims, 8 Drawing Sheets

BENZOXAZOLE COMPOUNDS AND METHODS OF USE

RELATED APPLICATION INFORMATION

The present application is a 35 U.S.C. §371 national phase application of PCT International Application No. PCT/US2009/058398, having an international filing date of Sep. 25, 2009, claiming priority to U.S. Provisional Patent Application No. 61/100,678 filed Sep. 26, 2008. The disclosures of each application are incorporated herein by reference in their entireties. The above PCT International Application was published in the English language and has been accorded International Publication No. WO 2010/036905 A1.

BACKGROUND OF THE INVENTION

Many early immune responses to damage or infection are initiated by a family of innate immune toll-like receptors (TLRs). The TLR family has broad specificity, recognizing molecular structures that are highly conserved among pathogenic organisms or different types of physical damage. The ligands of specific TLRs include endotoxin, single- or double-stranded RNA, peptidoglycan, flagellin, heat shock proteins, and in the case of TLR9, unmethylated CpG sequences in DNA (Bell et al., *Trends Immunol.* 24:528-533 (2003) and Wagner, *Trends Immunol.* 25:381-6 (2004)). While this early sensing of disease or damage is critical to the ensuing immune response, it can also be the source of inappropriate or damaging responses as well. For example, TLR9 has been implicated in autoimmune disorders, including lupus, which has long been associated with anti-DNA antibody reactivity, and multiple sclerosis (Prinz et al., *J Clin Invest* 116:456-464 (2006)). TLR9 also appears to underlie the uncontrolled inflammatory response that is associated with death from septic shock (Plitas et al., *J Exp Med* 205: 1277-83 (2008)).

TLR9 was first identified as an innate immune receptor expressed by human B cells and plasmacytoid dendritic cells (PDC) that binds unmethylated CpG sequences, resulting, in cellular activation and cytokine secretion (Hemmi et al., *Nature* 408:740-745 (2000)). These sequences are over-represented in bacterial DNA in comparison to eukaryotic DNA, and therefore can serve as an indicator of bacterial infection. However, eukaryotic DNA contains some unmethylated CpG and is capable of stimulating TLR9 as well (Vallin et al., *J Immunol.* 163:6306-13 (1999) and Leadbetter et al. (2002)). While DNA from dying cells is typically ingested and sequestered from the system, lupus is associated with genetic defects that lead to poor clearance and accumulation of excessive cell debris (Krislman et al., *Seminars in Immunology* 18:240-243 (2006)), exposing, the immune system to abnormally high levels of ligand. This condition, combined with targeted uptake of DNA-containing complexes by either complex-specific immunoglobulin on B cells, or Fc receptors on dendritic or antigen-presenting cells, can result in presentation and reaction to autoantigen, a response boosted by the presence of TLR9 ligand in the stimulating complex. This observation is exemplified by the fact that PDC respond to complexes found in systemic lupus erythematosus (SLE) serum by secreting α-interferon, and that this is Fc receptor and DNA-dependent and mediated by TLR9 (Leadbetter et al., (2002) and Means et al., *J Clin Invest.* 1152:407-17 (2005)). The resulting α-interferon can further drive dendritic cell and B cell maturation. Correspondingly, array data show activation of α-interferon inducible genes in patients with severe disease (Bennett et al., *J Exp Med.* 197:711-23 (2003)). As PDC are the predominant source of α-interferon in the body, this observation further associates this cell population with disease.

B cells are also central to lupus autoimmunity, and are driven to proliferate and produce IL-6 and antibodies by TLR9 stimulation with synthetic oligonucleotides. Due to preferential association with B cells expressing autoreactive cell surface immunoglobulin, autoantigen-specific cells will predominate in this response. A self-reinforcing cycle is thus at work, in which DNA or RNA-containing cell debris combines with antibodies from TLR9-stimulated autoantigen-specific B cells to stimulate plasmacytoid dendritic cells via Fc receptors.

SUMMARY OF THE INVENTION

A first embodiment of the present invention provides a compound of formula (I):

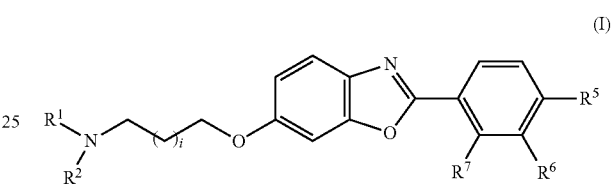

or a pharmaceutically acceptable salt thereof,
wherein one of $R^5$, $R^6$, or $R^7$ is a group of formula (a):

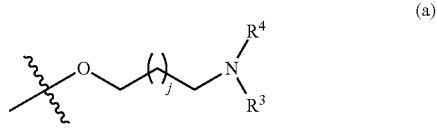

and when $R^5$ is (a), $R^6$ and $R^7$ are both H, when $R^6$ is (a), $R^5$ and $R^7$ are both H, and when $R^7$ is (a), $R^5$ and $R^6$ are both H;

i and j are the same and are 0, 1, 2, 3, or 4;

$R^1$ and $R^4$ are the same and selected from the group consisting of H, $CH_3$, and $CH_2CH_3$;

$R^2$ is $CH_3$ and $R^3$ is selected from the group consisting of $(CH_2)_hN(CH_3)_2$ and $(CH_2)_2$—O—$(CH_2)_2$—O—$(CH_2)_2N(CH_3)_2$, wherein h is 2, 3, or 4; or $R^2$ and $R^3$ are the same and selected from the group consisting of:

$(CH_2)_kCH_3$, wherein k is 0, 1 or 2;

$(CH_2)_mN(CH_2CH_3)_2$, wherein m is 2 or 3;

$(CH_2)_nN(CH_3)_2$, wherein n is 2, 3 or 4;

$(CH_2)_p$—O—$(CH_2)_qN(CH_3)_2$, wherein p and q are the same and are 2 or 3;

a group of formula (b):

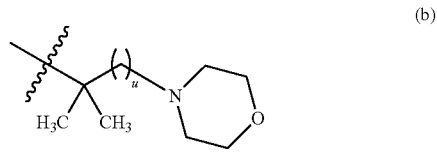

wherein u is 0 or 1; or a group of formula (c):

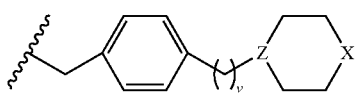

wherein v is 0 or 1, Z is N or CH,
and X is O or NCH$_3$; or
R$^1$—N—R$^2$ and R$^3$—N—R$^4$ are the same and selected from the group consisting of:
a group of formula (d):

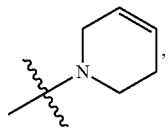

and
a group of formula (e):

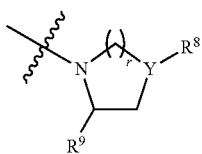

wherein
r is 1, 2, or 3,
Y is CH or N,
R$^8$ is H, CH$_3$, CH(CH$_3$)$_2$, N(CH$_3$)$_2$, CH$_2$OCH$_3$, or a group of formula (f):

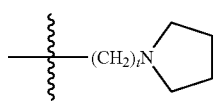

wherein t is 0 or 1, and
R$^9$ is H, CH$_2$OCH$_3$, or a group of formula (f).

A second embodiment of the present invention provides a pharmaceutical composition including a compound as described herein.

A third embodiment of the present invention provides a method of treating an immunological disorder such as sepsis, lupus, rheumatoid arthritis, or multiple sclerosis in a subject, including administering to the subject a compound as described herein in an effective amount.

A fourth embodiment of the present invention provides a method of treating lupus in a subject, including administering to the subject a compound as described herein in an effective amount.

A fifth embodiment of the present invention provides the use of a compound as described herein for the manufacture of a medicament for treating immunological disorders such as sepsis, lupus, rheumatoid arthritis, or multiple sclerosis.

Other embodiments of the present invention are disclosed herein and discussed in greater detail below.

DETAILED DESCRIPTION

A. Definitions

Figure 1:
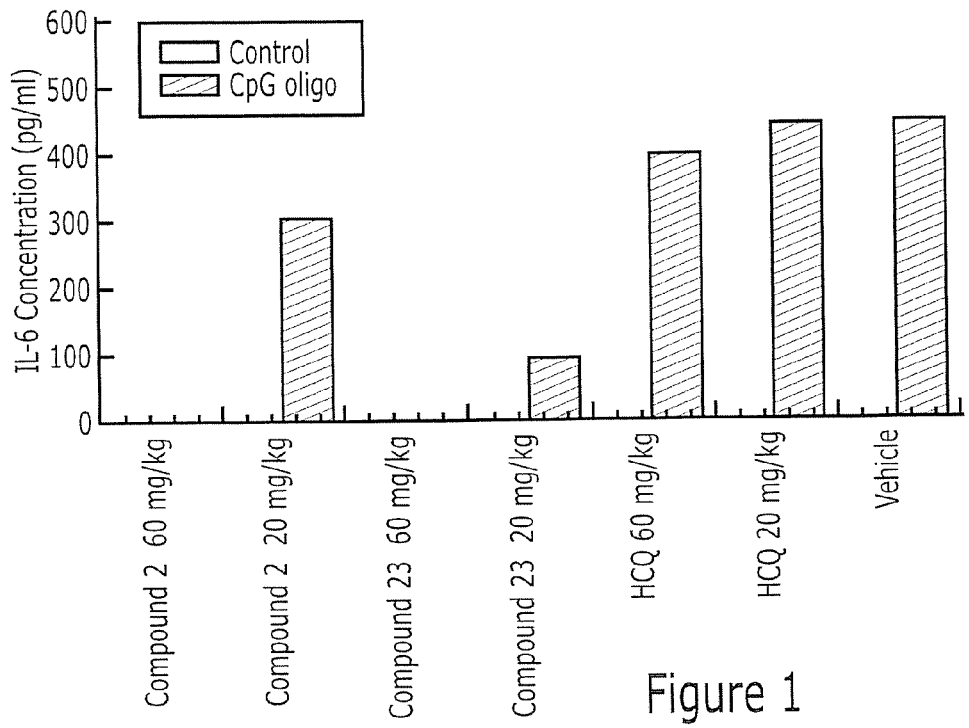
FIG. 1 is a bar graph showing the concentration of interleukin 6 (IL-6) detected in lymph nodes removed from mice after two weeks of administration of 20 mg/kg or 60 mg/kg of Compound 2, Compound 23, or hydroxychloroquine (HCQ) in vivo, and stimulation of the lymph nodes ex vivo with oligo CpG 1668, as described in Example 11.

"Treatment", "treat", and "treating" refer to reversing, alleviating, or inhibiting the progress of a disorder or disease as described herein. Moreover, as used herein, "treatment" of a subject includes the application or administration of a compound of the invention described herein to a subject, or application or administration of the compound to a cell or tissue from a subject, who has an immunological disorder, has a symptom of such an immunological disorder, or is at risk of (or susceptible to) such an immunological disorder, with the purpose of curing, healing, alleviating, relieving, altering, remedying, ameliorating, improving, or affecting the disorder, the symptom of the disorder, or the risk of (or susceptibility to) the disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of a more severe form or symptom of the disorder. The treatment or amelioration of symptoms can be based on objective or subjective parameters; including, the results of a physical examination, a psychiatric evaluation, or a diagnostic test known in the art.

In one embodiment, the term "treating" includes improving a symptom of an immunological disorder such as improvement or relief from inflammation, infection, fever, altered mental status, organ dysfunction, anemia, joint pain, fatigue, cognitive difficulties, spasticity and/or tremors caused by or associated with an immunological disorder.

"Prevention", "prevent", and "preventing" refer to eliminating or reducing the incidence or onset of a disorder or disease as described herein, as compared to that which would occur in the absence of the measure taken.

"Effective amount" refers to an amount that causes relief of symptoms of a disorder or disease as noted through clinical testing and evaluation, patient observation, and/or the like. An "effective amount" can further designate a dose that causes a detectable change in biological or chemical activity. The detectable changes may be detected and/or further quantified by one skilled in the art for the relevant mechanism or process. Moreover, an "effective amount" can designate an amount that maintains a desired physiological state, i.e., reduces or prevents significant decline and/or promotes improvement in the condition of interest. An "effective amount" can further refer to a therapeutically effective amount.

"Subject", as used herein, means a mammalian subject (e.g., dog, cat, horse, cow, sheep, goat, monkey, etc.), and particularly human subjects (including both male and female subjects, and including neonatal, infant, juvenile, adolescent, adult and geriatric subjects, and further including various races and ethnicities including, but not limited to, white, black, Asian, American Indian and Hispanic).

As used herein, the term "a pharmaceutically acceptable salt" refers to the relatively non-toxic, inorganic and organic acid salts of compounds of the invention. These salts can be prepared in situ during, the final isolation and purification of the compounds or by reacting the purified compound in its free form separately with a suitable organic or inorganic acid and isolating the salt thus formed. Representative acid salts include acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts. In one embodiment, the pharmaceutically acceptable salt is a hydrochloride/chloride salt.

B. Compounds

Some of the compounds described herein can comprise one or more asymmetric centers, and thus, the compounds can exist in various isomeric forms, e.g., stereoisomers and/or diastereomers. When the orientation of a bond around a chiral center is not specified in a formula, it is to be understood that the formula encompasses every possible isomer such as geometric isomer, optical isomer, stereoisomer and tautomer based on asymmetric carbon, which can occur in the structures of the inventive compounds.

As noted above, the present invention provides a compound of formula (I):

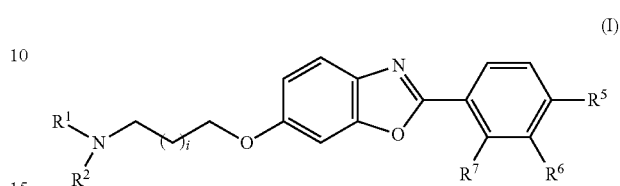

or a pharmaceutically acceptable salt thereof, wherein $R^1$, $R^2$, $R^5$, $R^6$, and $R^7$ are defined as described herein above.

In some embodiments of the compound of formula (I), i and j are both 1.

In further embodiments, $R^2$ and $R^3$ are the same and selected from the group consisting of:

$(CH_2)_k CH_3$, wherein k is 0, 1 or 2;

$(CH_2)_m N(CH_2 CH_3)_2$, wherein m is 2 or 3;

the group of formula (b) described herein above; and the group of formula (c) described herein above.

According to other embodiments, $R^1$—N—$R^2$ and $R^3$—N—$R^4$ are the same and are selected from:

a group of formula (g): a group of formula (h):

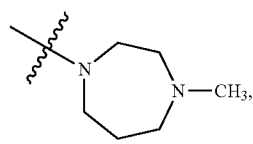

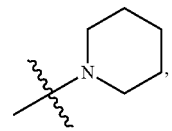

a group of formula (i): a group of formula (j):

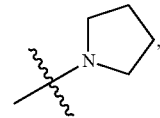

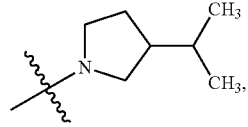

a group of formula (k): a group of formula (m):

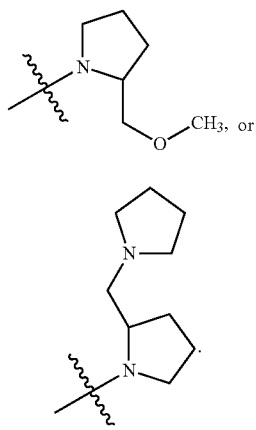

In some embodiments of the compound of formula (I):
i and j are both 1;
$R^1$ and $R^4$ are the same and selected from the group consisting of H and $CH_3$;
$R^2$ is $CH_3$ and $R^3$ is selected from the group consisting of $(CH_2)_2N(CH_3)_2$ and $(CH_2)_2$—O—$(CH_2)_2$—O—$(CH_2)_2N(CH_3)_2$, or
$R^2$ and $R^3$ are the same and selected from the group consisting of:
a) $(CH_2)_k CH_3$, wherein k is 0, 1, or 2;
b) $(CH_2)_m N(CH_2 CH_3)_2$, wherein M is 2 or 3;
c) the group of formula (b) described herein above; and
d) the group of formula (c) described hereinabove; or
$R^1$—N—$R^2$ and $R^3$—N—$R^4$ are the same and selected from the group consisting of:
the group of formula (g), the group of formula (h), the group of formula (i), the group of formula (j), the group of formula (k), and the group of formula (m) all as described herein above.

In further embodiments, $R^5$ is the group of formula (a) described hereinabove, and $R^6$ and $R^7$ are each H.

In particular embodiments of the compound of formula (I), the compound has a structure selected from:

| Compound | Structure |
|---|---|
| Compound 1 | 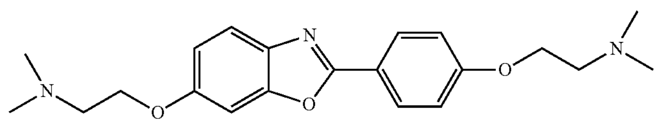 |
| Compound 2 | 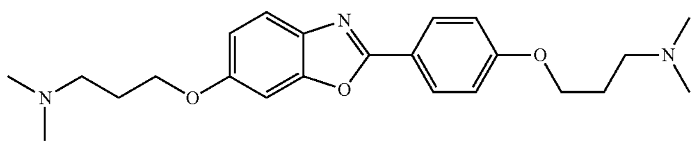 |
| Compound 3 | 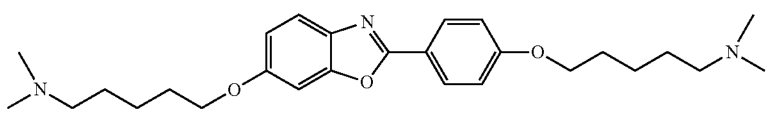 |
| Compound 4 | 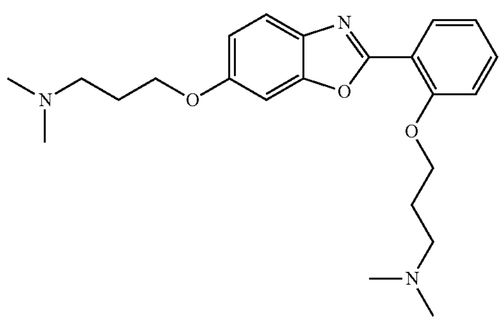 [SMILES: CN(C)CCCOc1ccc2nc(-c3ccccc3OCCCN(C)C)oc2c1] |
| Compound 5 | 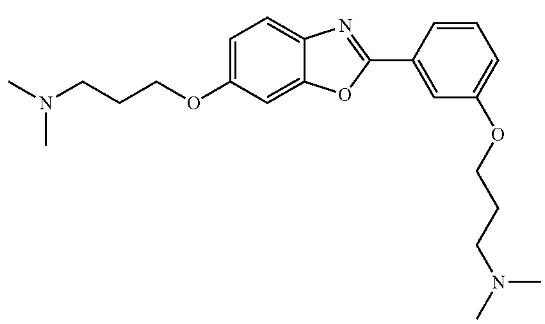 |

| Compound | Structure |
|---|---|
| Compound 6 | 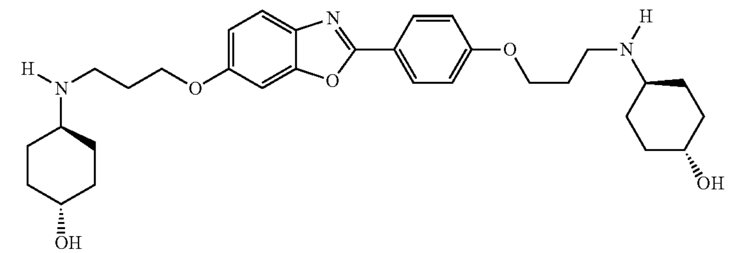 [SMILES: O[C@H]1CC[C@H](NCCCOc2ccc(-c3nc4ccc(OCCCN[C@H]5CC[C@H](O)CC5)cc4o3)cc2)CC1] |
| Compound 7 | 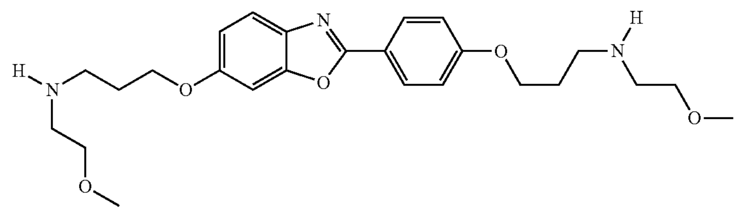 [SMILES: COCCNCCCOc1ccc(-c2nc3ccc(OCCCNCCOC)cc3o2)cc1] |
| Compound 8 | 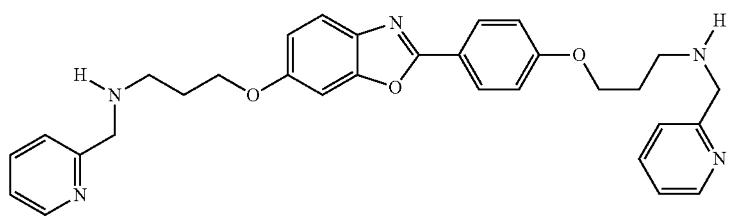 [SMILES: c1ccc(CNCCCOc2ccc(-c3nc4ccc(OCCCNCc5ccccn5)cc4o3)cc2)nc1] |
| Compound 9 | 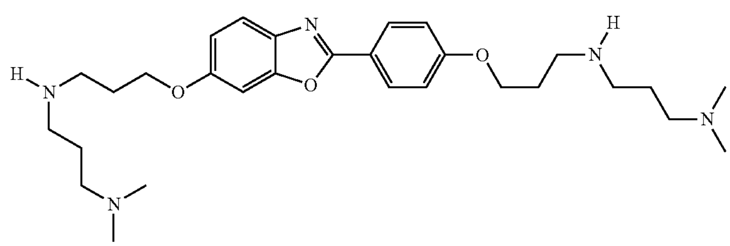 [SMILES: CN(C)CCCNCCCOc1ccc(-c2nc3ccc(OCCCNCCCN(C)C)cc3o2)cc1] |
| Compound 10 | 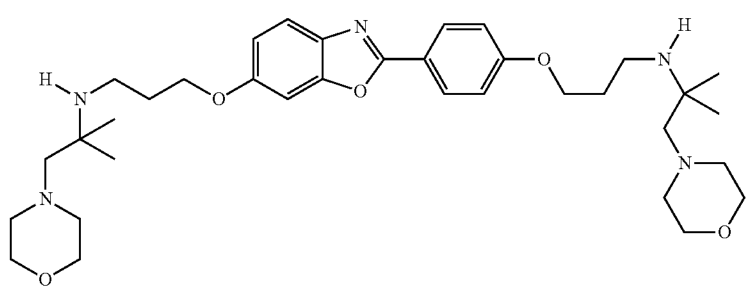 [SMILES: CC(C)(CN1CCOCC1)NCCCOc1ccc(-c2nc3ccc(OCCCNC(C)(C)CN4CCOCC4)cc3o2)cc1] |
| Compound 11 | 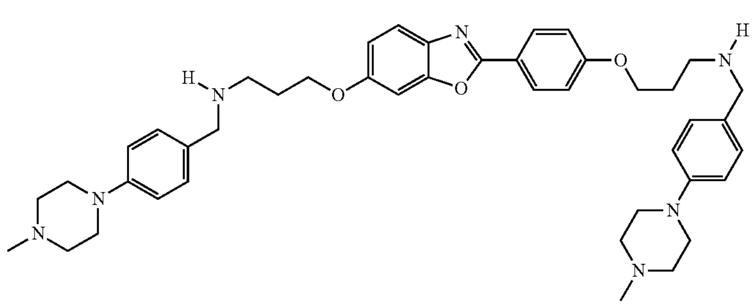 [SMILES: CN1CCN(c2ccc(CNCCCOc3ccc(-c4nc5ccc(OCCCNCc6ccc(N7CCN(C)CC7)cc6)cc5o4)cc3)cc2)CC1] |

-continued
| Compound | Structure |
|---|---|
| Compound 12 | 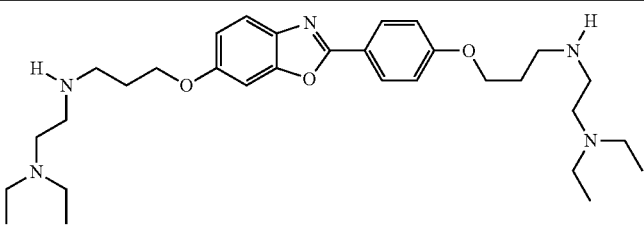 |
| Compound 13 | 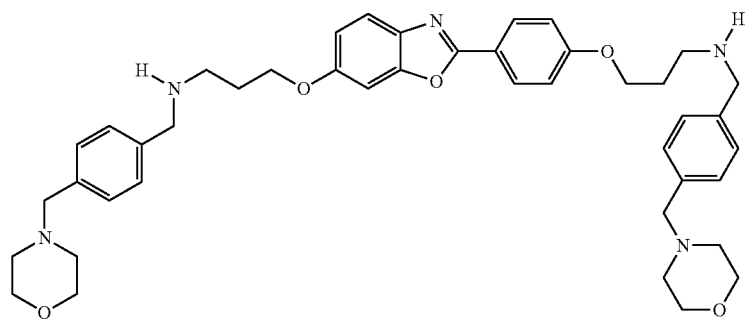 [SMILES: c1cc(CN2CCOCC2)ccc1CNCCCOc1ccc(-c2nc3ccc(OCCCNCc4ccc(CN5CCOCC5)cc4)cc3o2)cc1] |
| Compound 14 | 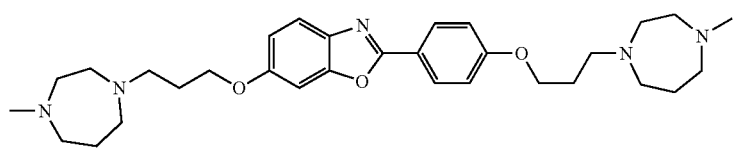 |
| Compound 15 | 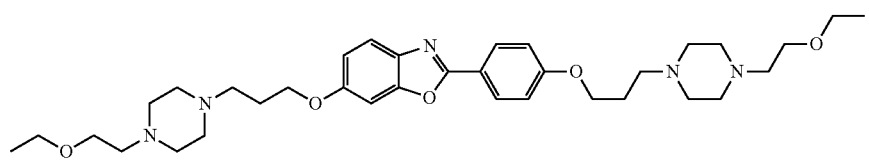 [SMILES: CCOCCN1CCN(CCCOc2ccc(-c3nc4ccc(OCCCN5CCN(CCOCC)CC5)cc4o3)cc2)CC1] |
| Compound 16 | 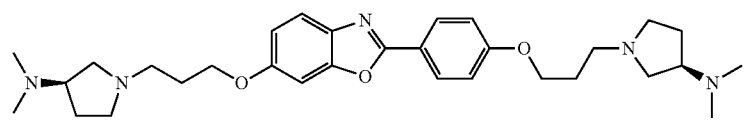 |
| Compound 17 | 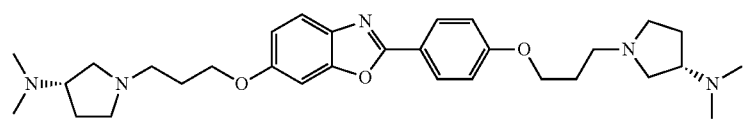 |
| Compound 18 | 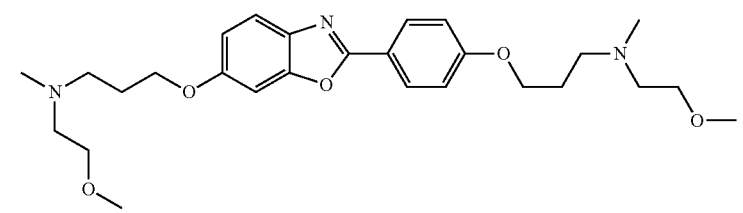 |
| Compound 19 | 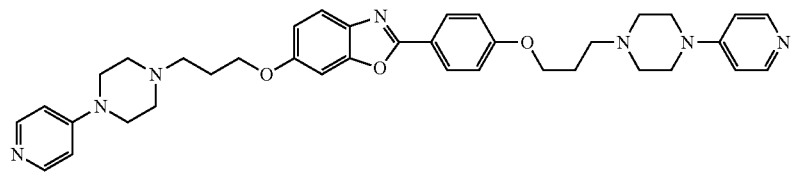 [SMILES: c1cc(N2CCN(CCCOc3ccc(-c4nc5ccc(OCCCN6CCN(c7ccncc7)CC6)cc5o4)cc3)CC2)ccn1] |

-continued
| Compound | Structure |
|---|---|
| Compound 20 | 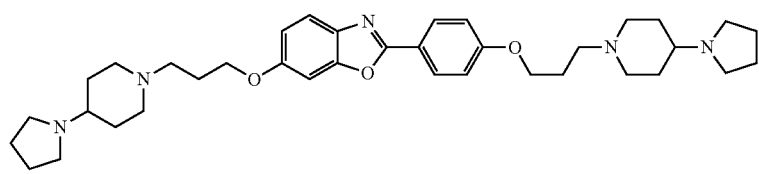 [SMILES: c1cc(-c2nc3ccc(OCCCN4CCC(N5CCCC5)CC4)cc3o2)ccc1OCCCN1CCC(N2CCCC2)CC1] |
| Compound 21 | 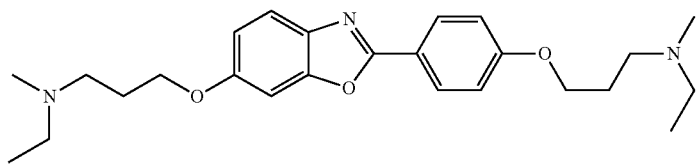 [SMILES: CCN(C)CCCOc1ccc(-c2nc3ccc(OCCCN(C)CC)cc3o2)cc1] |
| Compound 22 | 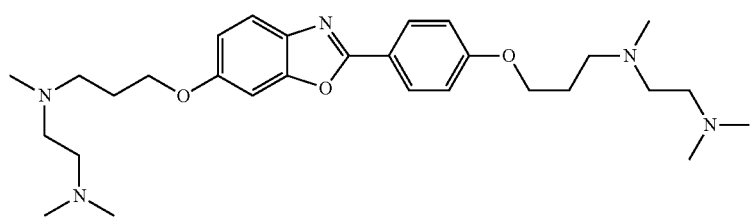 |
| Compound 23 | 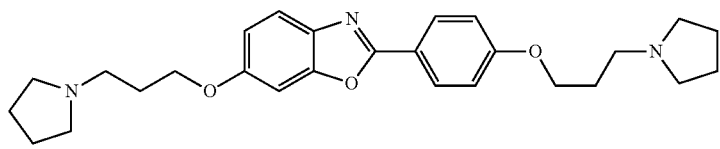 |
| Compound 24 | 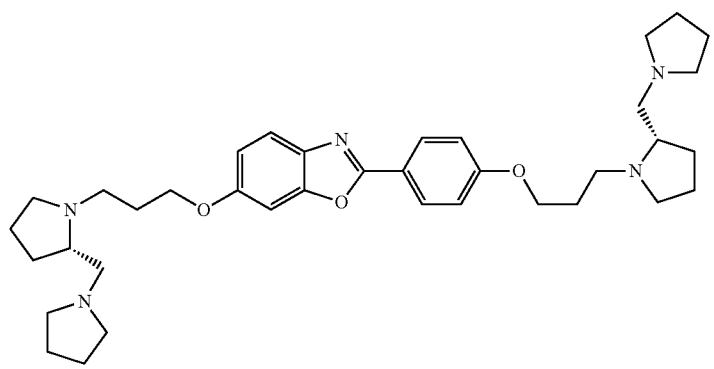 |
| Compound 25 | 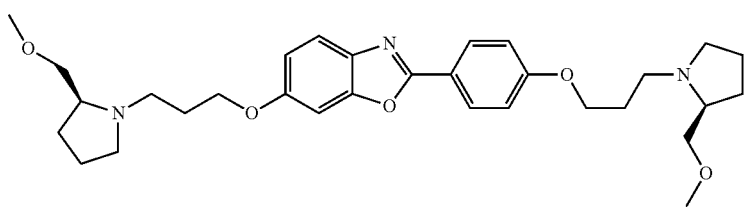 [SMILES: COC[C@@H]1CCCN1CCCOc1ccc(-c2nc3ccc(OCCCN4CCC[C@H]4COC)cc3o2)cc1] |
| Compound 26 | 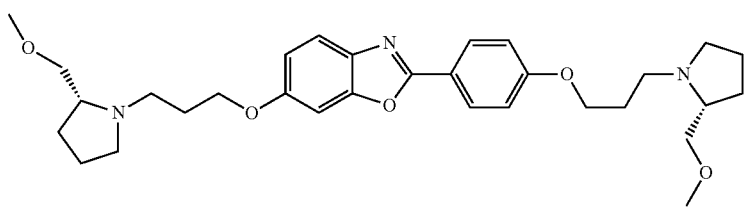 [SMILES: COC[C@H]1CCCN1CCCOc1ccc(-c2nc3ccc(OCCCN4CCC[C@@H]4COC)cc3o2)cc1] |

-continued
| Compound | Structure |
|---|---|
| Compound 27 | 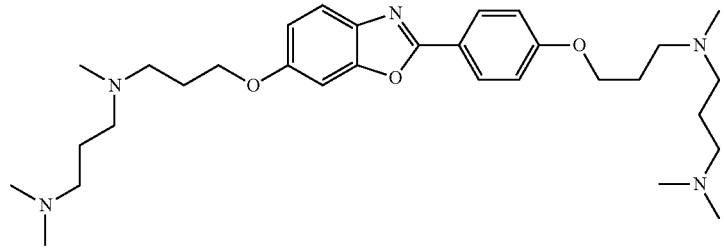 |
| Compound 28 | 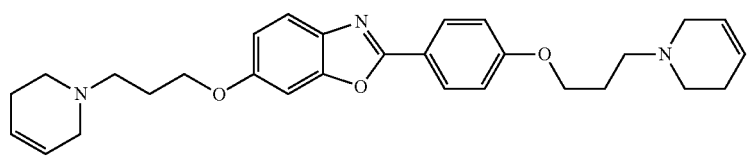 [SMILES: C1=CCN(CCCOc2ccc(-c3nc4ccc(OCCCN5CC=CCC5)cc4o3)cc2)CC1] |
| Compound 29 | 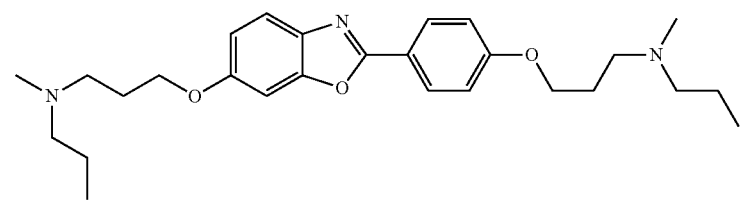 [SMILES: CCCN(C)CCCOc1ccc(-c2nc3ccc(OCCCN(C)CCC)cc3o2)cc1] |
| Compound 30 | 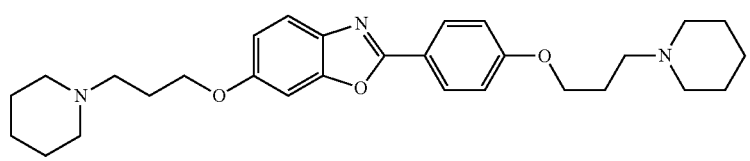 |
| Compound 31 | 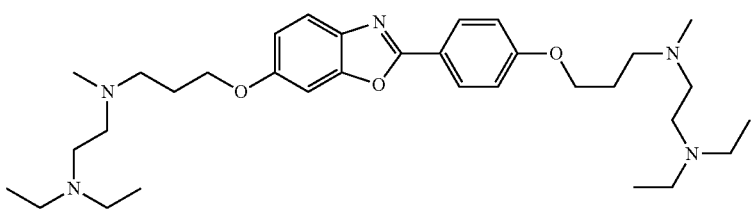 |
| Compound 32 | 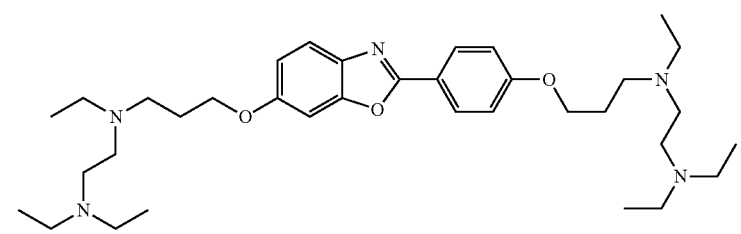 [SMILES: CCN(CC)CCN(CC)CCCOc1ccc(-c2nc3ccc(OCCCN(CC)CCN(CC)CC)cc3o2)cc1] |
| Compound 33 | 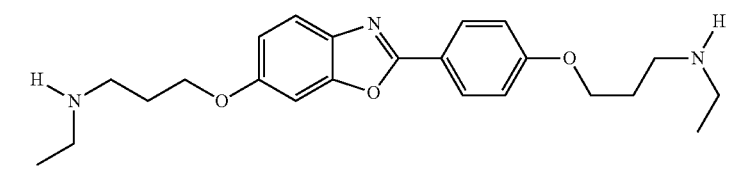 [SMILES: CCNCCCOc1ccc(-c2nc3ccc(OCCCNCC)cc3o2)cc1] |
| Compound 34 | 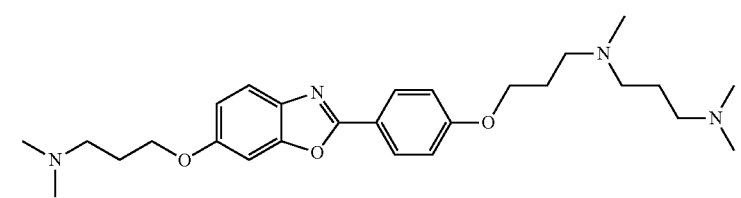 |

| Compound | Structure |
|---|---|
| Compound 35 | 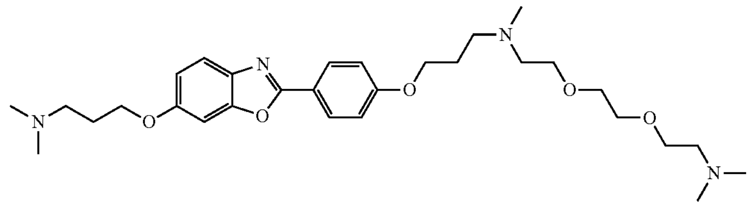 |
| Compound 36 | 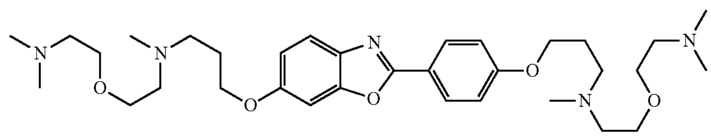 |
| Compound 37 | 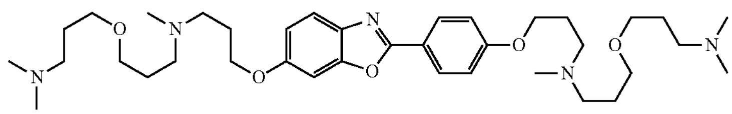 |
| Compound 38 | 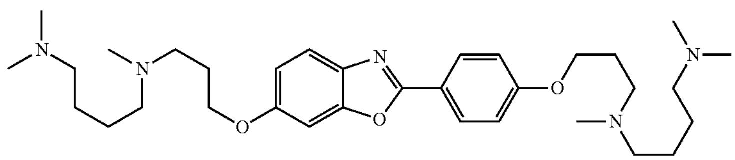 |

In another embodiment, the compound of Formula I is selected from the group consisting of Compound 1, Compound 2, Compound 10, Compound 11, Compound 12, Compound 13, Compound 14, Compound 16, Compound 17, Compound 26, Compound 29, Compound 30, Compound 31, Compound 32, Compound 34, and Compound 35 or a pharmaceutically acceptable salt thereof. In another embodiment, the compound is selected from the group consisting of Compound 13, Compound 16, Compound 22, Compound 23, Compound 26, Compound 27, Compound 30, Compound 34, and Compound 35 or a pharmaceutically acceptable salt thereof. In another embodiment, the compound is selected from the group consisting of Compound 23, Compound 26, and Compound 30, or a pharmaceutically acceptable salt thereof. In yet another embodiment, the compound is Compound 23 or a pharmaceutically acceptable salt thereof.

C. Synthesis of Compounds

Compounds described herein can be prepared by a sequence of reactions. General methods for preparing compounds of the present invention are set forth below. In certain cases, a particular compound is described by way of example as presented further below in the section describing the examples. Except as provided below, in the following methods, $R^1$, $R^2$, $R^3$, $R^4$, i, and j are the same as defined in Formula I, above.

Method 1—Alkylation, Amination or Alkylation, Amination and N-Methylation

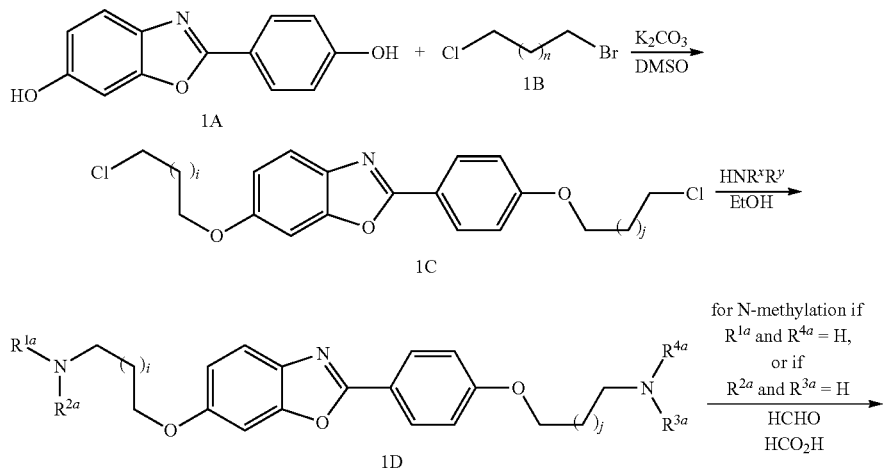

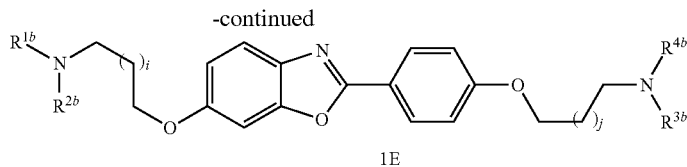

1E

In the reaction scheme of Method 1 shown above:
n, i, and j are the same and are 0, 1, 2, 3, or 4;
$R^{1a}$ and $R^{4a}$ are both the same as $R^x$;
$R^{2a}$ and $R^{3a}$ are both the same as $R^y$;
$R^{1b}$ and $R^{4b}$ are the same;
$R^{2b}$ and $R^{3b}$ are the same;
when $R^{1a}$ and $R^{4a}$ are both H, $R^{1b}$ and $R^{4b}$ are both methyl; and
when $R^{2a}$ and $R^{3a}$ are both H, $R^{2b}$ and $R^{3b}$ are both methyl.

In one method of synthesizing symmetrical compounds according to embodiments of the invention, 2-(4-hydroxyphenyl)benzoxazol-6-ol (1A) may be reacted with a bromochloroalkane (1B), e.g., in the presence of potassium carbonate in dimethyl sulfoxide (DMSO), to form the dichloroether derivative (1C). 2-(3-hydroxyphenyl)benzoxazol-6-ol and 2-(2-hydroxyphenyl)benzoxazol-6-ol may also be used in lieu of compound 1A. The dichloroether derivative (1C) may then be reacted with an amine (HNR$^x$R$^y$) to form diamine (1D). In the synthetic scheme for Method 1, the amine is generically referred to as HNR$^x$R$^y$ to indicate that a single amine reactant may be used to form the amine groups —NR$^{1a}$R$^{2a}$ and —NR$^{3a}$R$^{4a}$ in diamine (1D). As such, R$^x$ is the same as R$^{1a}$ and R$^{4a}$, and R$^y$ is the same as R$^{2a}$ and R$^{3a}$. Additionally, if R$^{1a}$ and R$^{4a}$ are hydrogen, or if R$^{2a}$ and R$^{3a}$ are hydrogen, the compound may optionally undergo N-methylation to form the N-methyl derivatives (1E). Compounds 1D and 1E may both be compounds according to embodiments of the invention.

Method 2—Mitsunobu Reaction or Mitsunobu Reaction and N-Methylation

In the reaction scheme of Method 2 shown above:
n, i, and j are the same and are 0, 1, 2, 3, or 4;
$R^{1a}$ and $R^{4a}$ are both the same as $R^x$:
$R^{2a}$ and $R^{3a}$ are both the same as $R^y$; and
$R^{1b}$ and $R^{4b}$ are the same;
$R^{2b}$ and $R^{3b}$ are the same;
when $R^{1a}$ and $R^{4a}$ are both H, $R^{1b}$ and $R^{4b}$ are both methyl; and
when $R^{2a}$ and $R^{3a}$ are both H, $R^{2b}$ and $R^{3b}$ are both methyl.

In another method for synthesizing symmetrical compounds according to embodiments of the invention, 2-(4-hydroxyphenyl)benzoxazol-6-ol (2A) may be reacted with a hydroxyalkylamine (2B), via the Mitsunobu reaction, to produce a diamine (2C). 2-(3-hydroxyphenyl)benzoxazol-6-ol and 2-(2-hydroxyphenyl)benzoxazol-6-ol may also be used in lieu of compound 2A. Additionally, if $R^{1a}$ and $R^{4a}$ are hydrogen, or if $R^{2a}$ and $R^{3a}$ are hydrogen, the compound may optionally undergo N-methylation to form the N-methyl derivatives (2D). Compounds 2C and 2D may both be compounds according to embodiments of the invention.

Method 3—for Asymmetric Side Chain Analogs

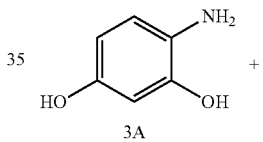

3A

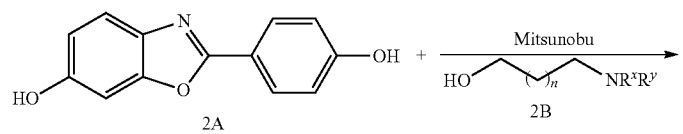

2A  2B

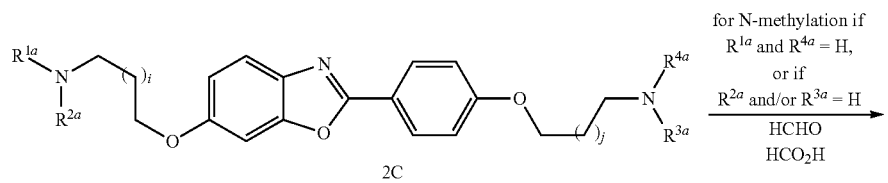

2C

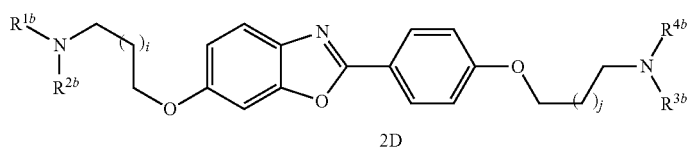

2D

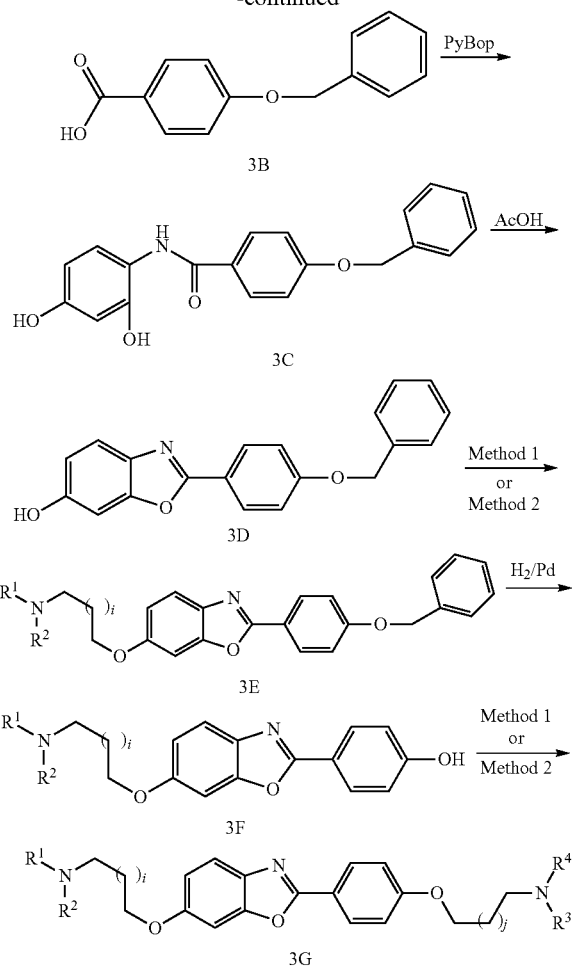

In the reaction scheme of Method 3:
$R^1$ and $R^4$ are the same and selected from the group consisting of H and $CH_3$; and
$R^2$ is $CH_3$ and $R^3$ is selected from the group consisting of $(CH_2)_2N(CH_3)_2$, and $(CH_2)_2$—O—$(CH_2)_2$—O—$(CH_2)_2$ $N(CH_3)_2$.

Asymmetric compounds according to some embodiments of the invention may be synthesized via Method 3. In such case, 4-aminobenzene-1,3-diol (3A) may be reacted with a benzoic acid having a protected hydroxyl group, such as 4-(benzyloxy)benzoic acid (3B), 3-(benzyloxy)benzoic acid or 2-(benzyloxy)benzoic acid in the presence of benzotriazole-1-yl-oxy-tris-(dimethylamino)-phosphonium hexafluorophosphate (PyBop), to form the benzamide derivative (3C). The benzamide may then cyclized to form the benzoxazole ring (3D). At this point, either Method 1 or Method 2, described above, may be used to convert the hydroxy-functional benzoxazole (3D) to the amine (3E). Referring to Methods 1 and 2, $R^1$ may be $R^{1a}$ or $R^{1b}$ and $R^2$ may be $R^{2a}$ or $R^{2b}$. The benzyl ether group may then be deprotected, e.g., by hydrogenation with palladium, to form the hydroxy-functional amine (3F). Then, either Method 1 or Method 2 may be used to transform the hydroxyl-functional amine to the diamine (3G). Referring to Methods 1 and 2, $R^4$ may be $R^{4a}$ or $R^{4b}$ and $R^3$ may be $R^{3a}$ or $R^{3b}$.

D. Pharmaceutical Compositions

In one embodiment, the present invention is a pharmaceutical composition comprising the compound. In another embodiment, the pharmaceutical composition further comprises a pharmaceutically acceptable carrier. The term "pharmaceutically acceptable carrier" as used herein refers to any substance, not itself a therapeutic agent, used as a vehicle for delivery of a therapeutic agent to a subject.

The compositions of the present invention may be suitable for formulation for oral, parenteral, inhalation spray, topical, rectal, nasal, sublingual, buccal, vaginal or implanted reservoir administration, etc. Preferably, the compositions are administered orally, topically, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

A pharmaceutically acceptable oil may be employed as a solvent or suspending medium in compositions of the present invention. Fatty acids, such as oleic acid and its glyceride derivatives are suitably included in injectable formulations, as are natural pharmaceutically acceptable oils, such as olive oil or castor oil, especially in their polyoxyethylated versions. The oil containing compositions of the present invention may also contain a long-chain alcohol diluent or dispersant, such as carboxymethyl cellulose or similar dispersing agents that are commonly used in the formulation of pharmaceutically acceptable dosage forms including emulsions and suspensions. The compositions suitably further comprise surfactants (such as non-ionic detergents including Tween® or Span®) other emulsifying agents, or bioavailability enhancers.

The compositions of this invention may be in the form of an orally acceptable dosage form including, but not limited to, capsules, tablets, suspensions or solutions. The oral dosage form can include at least one excipient. Excipients used in oral formulations of the present can include diluents, substances added to mask or counteract a disagreeable taste or odor, flavors, dyes, fragrances, and substances added to improve the appearance of the composition. Some oral dosage forms of the present invention suitably include excipients, such as disintegrants, binding agents, adhesives, wetting agents, polymers, lubricants, or glidants that permit or facilitate formation of a dose unit of the composition into a discrete article such as a capsule or tablet suitable for oral administration additional. Excipient-containing tablet compositions of the invention can be prepared by any suitable method of pharmacy which includes the step of bringing into association one or more excipients with a compound of the present invention in a combination of dissolved, suspended, nanoparticulate, microparticulate or controlled-release, slow-release, programmed-release, timed-release, pulse-release, sustained-release or extended-release forms thereof.

Alternatively, pharmaceutically acceptable compositions of this invention may be in the form of a suppository for rectal administration. The suppositories can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of the present invention may be in the form of a topical solution, ointment, or cream in which the active component is suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Where the topical formulation is in the form of an ointment or cream, suitable carriers include, but are not limited to, mineral oil, sorbitan monostearate, polysorbate 60, cetyl esters wax, cetearyl alcohol, 2 octyldodecanol, benzyl alcohol and water.

When the pharmaceutically acceptable composition is an ophthalmic formulation, it may be a micronized suspension in isotonic, pH adjusted sterile aqueous solution, or as a solution in isotonic, pH adjusted sterile saline, either with or without a preservative such as benzylalkonium chloride. Alternatively, for ophthalmic uses, the pharmaceutically acceptable compositions may be formulated in the form of an ointment.

The pharmaceutically acceptable compositions of this invention may also be administered by nasal, aerosol or by inhalation administration routes. Such compositions are prepared according to techniques well-known in the art of pharmaceutical formulation and may be prepared as solutions in saline, employing, benzyl alcohol or other suitable preservatives, absorption promoters to enhance bioavailability, fluorocarbons, and/or other conventional solubilizing or dispersing agents.

Additionally, the pharmaceutical formulation including compounds of the present invention can be in the form of a parenteral formulation.

In certain embodiments, the pharmaceutically acceptable compositions of this invention are formulated preferably for oral administration.

E. Methods of Use

In another embodiment, the present invention is a method of preventing or treating an immunological disorder in a subject comprising administering a subject a therapeutically effective amount of a compound of the invention. In a particular embodiment, the compound of the present invention used to prevent or treat an immunological disorder, according to methods of the present invention, is a compound of Formula I selected from the group consisting of: Compound 13, Compound 16, Compound 22, Compound 23, Compound 26, Compound 27, Compound 30, Compound 34, and Compound 35 or a pharmaceutically acceptable salt thereof. In another embodiment, the compound is selected from the group consisting of Compound 23, Compound 26, and Compound 30 or a pharmaceutically acceptable salt thereof. In another embodiment, the compound is Compound 23 or a pharmaceutically acceptable salt thereof.

In one embodiment the immunological disorder prevented or treated with the method of the present invention is an autoimmune disease. As used herein the term "autoimmune disease" refers to maladies that are generally caused by the failure of the immune system to distinguish self components from non-self components. Autoimmune diseases that can be prevented or treated by compounds of the present invention include, but are not limited to, lupus (such as SLE), pemphigus vulgaris, myasthenia gravis, hemolytic anemia, thrombocytopenia purpura, Grave's disease, Sjogren's disease, dermatomyositis, Hashimoto's disease, polymyositis, inflammatory bowel disease, multiple sclerosis, diabetes mellitus, ulcerative colitis, rheumatoid arthritis, scleroderma and psoriasis. In particular embodiments of the present invention, the autoimmune disease is lupus or multiple sclerosis. In some embodiments, the autoimmune disease is SLE. As used herein, lupus refers to an autoimmune disease characterized by antibodies against self-cellular components including DNA, RNA, histones, and nucleosomes. Physical symptoms include kidney disease resulting, from autoantibody or immune complex deposition in the glomeruli, cutaneous rash, photosensitivity, arthritis and neurologic disorders including seizures and psychosis. The disease predominantly affects women, and usually strikes young, adults. While rarely directly fatal, it is associated with increased mortality and has a severe impact on quality of life, with ongoing fatigue, weight loss, atherosclerotic risk, and fever.

In another embodiment, the immunological disorder is sepsis. As used herein, sepsis refers to a systemic inflammatory response caused by an infection. Compounds of the present invention may be administered to treat severe sepsis and septic shock, both of which may result from sepsis. In particular embodiments, compounds of the present invention may be administered to treat severe sepsis. In other embodiments, compounds of the present invention may be used to treat septic shock.

According to further embodiments of the present invention, the compounds described herein can used for the treatment of lupus, multiple sclerosis and/or rheumatoid arthritis during relatively short periods of time when the disease flares such that symptoms of the disease increase in intensity and/or type. In some embodiments, the compounds described herein can be used as a chronic treatment, e.g., treatment that lasts days, months or years.

In some embodiments of the present invention, the compounds described herein can be co-administered with an additional agent useful for treating lupus, i.e., a combination therapy. The additional agent useful for treating lupus can be one or more of the following classes of drugs: steroids (e.g., glucocorticoids and corticosteroids), immunosuppressives, nonsteroidal anti-inflammatory drugs (NSAIDs), antibody therapies, interferons, cytotoxics and antimalarials. In some embodiments, the additional agent useful for treating lupus is at least one of the following: dehydroepiandrosterone (DHEA), prednisone, prednisolone, methylprednisolone, hydrocortisone, fludrocortisone, clobetasol, halobetasol, triamcinolone, betamethasone, fluocinolone, fluocinonide, leflunomide, azathioprine, methotrexate, mitoxantrone, cladribine, chlorambucil, cyclophosphamide, cyclosporine, mycophenolate (including mycophenoloc acid, mycophenolate mofetil and mycophenolate sodium), celecoxib, diclofenac, fenoprofen, flurbiprofen, ibuprofen, ketoprofen, fenbufen, indomethacin, meclofamate, meloxicam, nabumetone, naproxen, oxaprozin, rofecoxib, salicylates, acetylsalicylic acid, acetaminophen, sulindac, tolmetin, rituximab, belimumab, infliximab, adalimumab, epratuzumab, natalizumab, α-interferon and/or quinine and quinine derivatives such as hydroxychloroquine, chloroquine, quinidine and quinacrine.

In some embodiments, the compounds described herein can be co-administered with an additional agent useful for treating multiple sclerosis, i.e., a combination therapy. The additional agent useful for treating multiple sclerosis can be one or more of the following classes of drugs: steroids (e.g., glucocorticoids and corticosteroids), immunosuppressives, antibody therapies and interferons. In some embodiments, the additional agent useful for treating multiple sclerosis is at least one of the following: dehydroepiandrosterone, prednisone, prednisolone, methylprednisolone, hydrocortisone, fludrocortisone, clobetasol, halobetasol, triamcinolone, betamethasone, fluocinolone, fluocinonide, azathioprine, methotrexate, novantrone, copaxone, cladribine, chlorambucil, cyclophosphamide, cyclosporine, mycophenolate (including mycophenoloc acid, mycophenolate mofetil and mycophenolate sodium), rituximab, belimumab, epratuzumab, natalizumab and/or β-interferons.

In still other embodiments, the compounds described herein can be co-administered with an additional agent useful for treating rheumatoid arthritis, i.e., a combination therapy. The additional agent useful for treating rheumatoid arthritis can be one or more of the following classes of drugs: cyclooxygenase-2 (COX-2) inhibitors, NSAIDs, disease-modifying antirheumatic drugs (DMARDs), steroids, immunosuppressives and antibody therapies. In some embodiments, the additional agent useful for treating rheumatoid arthritis is at least one of the following: celecoxib, diclofenac, fenoprofen, flurbiprofen, ibuprofen, ketoprofen, fenbufen, indomethacin, meclofamate, meloxicam, nabumetone, naproxen, oxaprozin, rofecoxib, acetylsalicylic acid, acetaminophen, sulindac, tolmetin, dehydroepiandrosterone, prednisone, prednisolone, methylprednisolone, hydrocortisone, fludrocortisone, clobetasol, halobetasol, triamcinolone, betamethasone, fluocinolone, fluocinonide, leflunomide, azathioprine, methotrexate, mitoxantrone, cladribine, chlorambucil, cyclophosphamide, cyclosporine, mycophenolate mofetil, rituximab, belimumab, infliximab, adalimumab, epratuzumab, natalizumab, anakinra, abatacept, auranofin, aurothioglucose, aurothiomalate, sulfasalazine, minocycline and/or quinine and quinine derivatives such as hydroxychloroquine, chloroquine, quinidine and quinacrine.

In some embodiments, the compounds described herein can be co-administered with an additional agent useful for treating sepsis, i.e., a combination therapy. The additional agent useful for treating sepsis can be one or more of the following classes of drugs: antibiotics, aminoglycosides, colloid or crystalloid fluids (i.e., fluid therapy), vasopressors, inotropic drugs, steroids and anticoagulants. In some embodiments, the additional agent useful for treating sepsis is at least one of the following: albumin, starch, norepinephrine, dopamine, vasopressin, dobutamine, prednisone, prednisolone, methylprednisolone, hydrocortisone, fludrocortisone, and activated protein C including, but not limited to, human recombinant activated protein C (rhAPC).

In further embodiments, the compounds can be used to decrease the doses of other treatments used in combination to treat the disorders described herein, for example, in steroid sparing regimens.

In some embodiments, the compounds described herein are administered prior to, concurrently with or subsequent to the administration of the additional agent useful for treating lupus, multiple sclerosis, rheumatoid arthritis and/or sepsis.

Administration of the compounds described herein "prior to" administration of the additional agent refers to administering the compounds described herein to a subject prior to initial treatment with the additional agent, or prior to administration of the additional agent during a treatment protocol that includes administering the compounds described herein and the additional agent to a subject population that is at risk or afflicted with lupus, multiple sclerosis, rheumatoid arthritis and/or sepsis.

With concurrent administration, the compounds described herein and the additional agent are administered at the same point in time or immediately following one another. In general, the compounds described herein and the additional agent are administered at times sufficiently close that the results observed are relatively indistinguishable from those achieved when they are administered at the same point in time.

The compounds may be administered to subjects by any suitable route, including orally (inclusive of administration via the oral cavity and further including administration via an orogastric feeding tube), parenterally, by inhalation spray, topically, transdermally, rectally, nasally (including a nasogastric feeding tube), sublingually, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, parenterally, transdermally or by inhalation spray.

Compounds are administered to the subjects in an effective amount. An effective amount is generally 0.01 mg/kg to 500 mg/kg body weight per day. In some embodiments, the pharmaceutically acceptable compositions may be formulated so that a dosage of between 0.01 mg/kg to 100 mg/kg body weight per day of the compound can be administered to a patient receiving these compositions. In certain embodiments, the compositions of the present invention are formulated to provide a dosage of between 0.01 mg and 70 mg. In other embodiments, the compositions of the present invention are formulated to provide a dosage of between 0.1 mg and 25 mg or between 5 mg and 60 mg.

In some embodiments, the effective dose is between about 5 and 250 mg/kg, between about 10 and 200 mg/kg, or between about 20 and 120 mg/kg. In some embodiments, effective dosages include 5 mg/kg, 10 mg/kg, 20 mg/kg, 25 mg/kg, 40 mg/kg, 50 mg/kg, 60 mg/kg, 75 mg/kg, 100 mg/kg, 120 mg/kg and 150 mg/kg. Dosage forms can be in the form, e.g., of tablets or capsules, and the effective dose may be provided in one or more tablets, capsules or the like, and be provided once a day or throughout the day at intervals, e.g., of 4, 8 or 12 hours. Tablets or capsules, for example, could contain, e.g., 10, 25, 50, 75, 100, 150, 200 mg of compound. Liquid formulations could also be prepared so that any dosage could readily and conveniently be dispensed.

In some embodiments, the amount of the compounds of the present invention that may be combined with the excipient materials to produce a composition in a single dosage form will vary depending, upon the host treated, and the particular route of administration.

It should also be understood that a specific dosage and treatment regimen for any particular patient will depend upon a variety of factors, including the activity of the specific compound employed, the age, body weight, general health, gender, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It should be understood that these examples are for illustrative purposes only and are not to be construed as limiting this invention in any manner. A comparator compound is used in several of the examples below. The formula of the comparator is as follows:

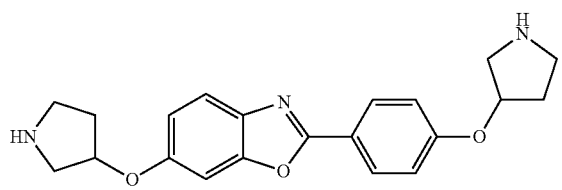 [SMILES: c1cc(-c2nc3ccc(OC4CCNC4)cc3o2)ccc1OC1CCNC1]

Exemplary compounds of the present invention were prepared in accordance with the schemes and experimental designs described below.

Example 1

Synthesis of Compound 40

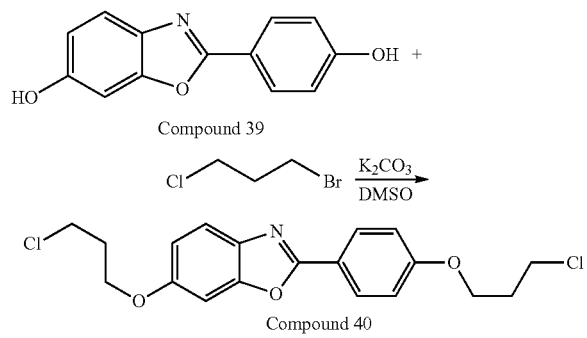

Compound 40. As depicted above, 1-bromo-3-chloropropane (7.3 mL, 0.074 mol) was added to a stirring mixture of Compound 39 (5.62 g, 0.0247 mol) and potassium carbonate (10 g, 0.074 mol) in DMSO (50 mL) at room temperature and the resulting mixture was stirred for 4 hours and thin-layer chromatography (TLC) showed the reaction was completed. The mixture was then poured into water (200 mL), extracted three times in 150 mL ethyl acetate (EtOAc), dried over $Na_2SO_4$, filtered and concentrated. Vacuum chromatography (10% to 30% EtOAc/hexane) of the residue gave a white solid product Compound 40 (8.10 g, 86%). Crystallization in hexane/EtOAc gave a white pure solid product (6.40 g) and mother liquor with minor impurities (1.60 g). $^1$H NMR (400 MHz, $CD_3OD$) δ 8.11 (d, J=9.1 Hz, 2H), 7.55 (d, J=8.8 Hz, 1H), 7.27 (d, J=2.3 Hz, 1H), 7.11 (d, J=9.1 Hz, 2H), 7.00 (dd, J=2.3, 8.8 Hz, 1H), 4.22 (t, J=5.9 Hz, 2H), 4.19 (t, J=6.15, 2H), 3.78 (tt, J=6.4 Hz, 4H), 2.30 (dt, J=1.76, 1.76 Hz, 4H). For preparation of starting compound Compound 39, see *J. Med. Chem.* 2004, 47, 5021-5040.

The same reaction was performed with isomers of Compound 39. Isomers Compound 47 and Compound 48 were prepared via the synthetic procedure in *J. Med. Chem.* 2004, 47, 5021-5040.

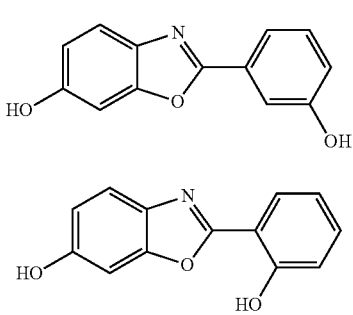

Compound 47

Compound 48

Example 2

Synthesis of Compound 49

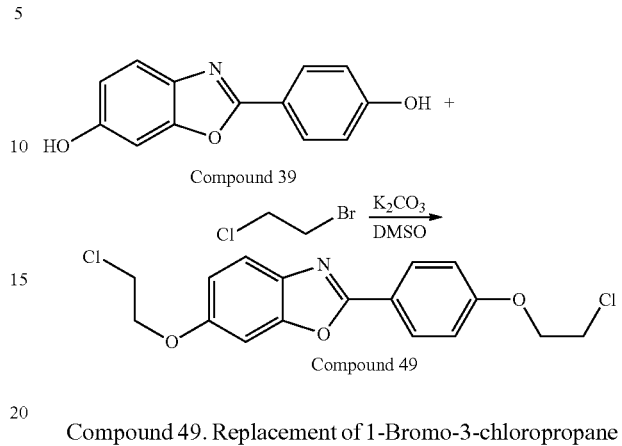

Compound 49. Replacement of 1-Bromo-3-chloropropane with 1-Bromo-2-chloroethane in Example 1 gave Compound 49.

Example 3

Synthesis of Compound 50

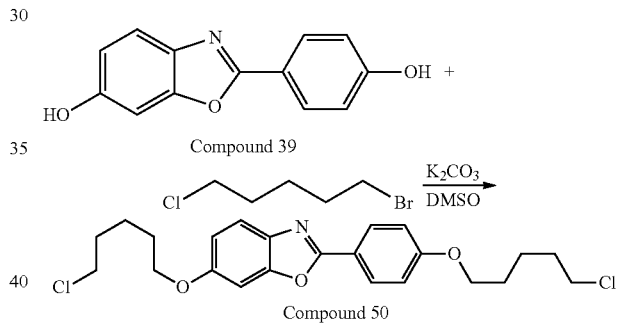

Compound 50. Replacement of 1-Bromo-3-chloropropane with 1-Bromo-5-chloropentane in Example 1 gave Compound 50.

Example 4

Synthesis of Compound 23

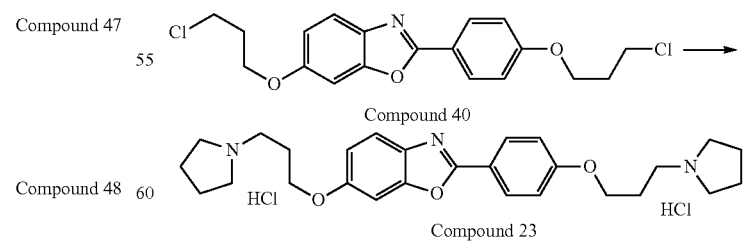

Compound 23. Referring to the scheme above, a mixture of Compound 40 (8.40 g, 0.0221 mol) produced as described in Example 1 and pyrrolidine (7.4 mL, 0.088 mol) in ethanol (50 mL) was heated at 100° C. for 12 hours under sealed tube.

TLC (20% triethylamine in methanol (Et₃N/MeOH)) showed a single new spot and mass spectroscopy showed one single desired peak of 450 (M+H). The mixture was cooled to room temperature, concentrated and the excess pyrrolidine was removed by azeotropic concentration with toluene (three times in 50 mL). The residue was dissolved in ethanol (EtOH), filtered and concentrated. The residual solid was crystallized in MeOH/EtOAc to give pure product Compound 23 (7.88 g, 68%). ¹H NMR (400 MHz, CD₃OD) δ 8.12 (d, J=8.9 Hz, 2H), 7.57 (d, J=8.8 Hz, 1H), 7.28 (d, J=2.2 Hz, 1H), 7.12 (d, J=8.9 Hz, 2H), 7.01 (dd, J=2.2, 8.8 Hz, 1H), 4.18 (t, J=5.86 Hz, 2H), 4.15 (t, J=6.15 Hz, 2H), 3.07-2.94 (m, 12H), 2.15 (m, 4H), 1.96 (m, 8H); MS (ES⁺) m/z 450.4.

Example 5

Synthesis of Compound 30

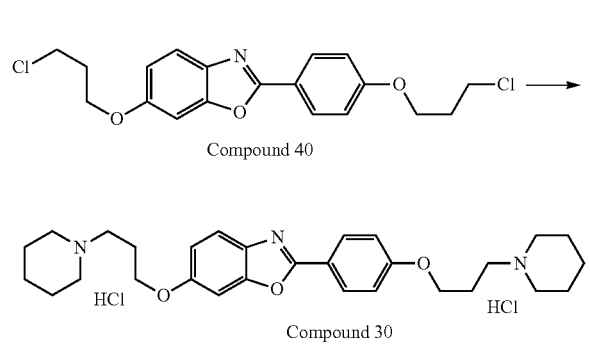

Compound 30. Referring to the scheme above, a mixture of Compound 40 (13.4 g, 0.0352 mol) produced as described in Example 1 and piperidine (14 mL, 0.14 mol) in ethanol (100 mL, 2 mol) was heated at 100° C. for 18 hours under sealed tube. TLC (10% Et₃N/MeOH) showed a single spot and MS showed one single desired peak of 478 (M+H). The mixture was concentrated and the excess piperidine was removed by azeotropic concentration with toluene (three times in 50 mL). The residue was dissolved in water with addition of MeOH, and then 1N NaOH was added until no further precipitate was formed with adequate stirring. The mixture was concentrated to remove any residual MeOH, filtered and washed with water. The collected free form solid (16.55 g, 34.7 mmol after dried under vacuum) was dissolved in warm MeOH (100 mL) and treated with 70 mL of 1N HCl (70 mmol) to form a di-HCl salt and the mixture was concentrated to dryness. The residual solid was crystallized in MeOH/EtOAc to give a pure product Compound 30 (16.0 g, 82%). ¹H NMR (400 MHz, CD₃OD) δ 8.13 (d, J=8.8 Hz, 2H), 7.58 (d, J=8.8 Hz, 1H), 7.29 (d, J=2.3 Hz, 1H), 7.14 (d, J=8.8 Hz, 2H), 7.02 (dd, J=2.3, 8.8 Hz, 1H), 4.21 (t, J=5.57 Hz, 2H), 4.19 (t, J=5.57 Hz, 2H), 3.59 (m, 4H), 3.34 (m, 4), 2.99 (m, 4H), 2.28 (tt, J=2.3, 5.6 Hz, 4H), 2.00-1.50 (m, 12H); MS (ES⁺) m/z 478.5.

Example 6

Synthesis of Compound 51

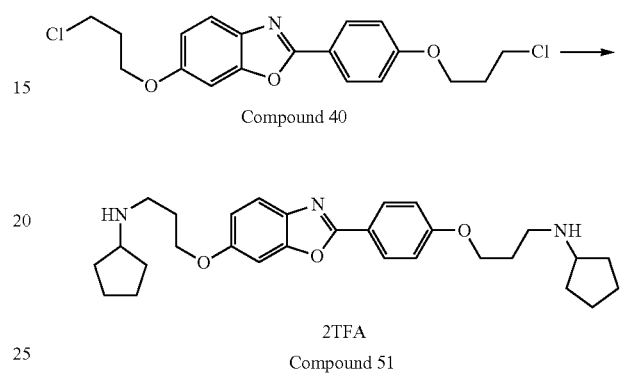

Compound 51. Analogs such as Compound 51 may be prepared using semi-automated synthesis (SAS) using the following procedure. A mixture of Compound 40 (27.0 mg, 0.071 mmol) and cyclopentylamine (98.6 mg, 1.16 mmol) in N-methylpyrrolidinone (0.5 mL) was heated by microwave at 180° C. for 300 seconds. The crude reaction mixture was purified by LC/MS under acidic conditions. The collected fractions containing the desired product were checked by analytical LC/MS for purity. The overall purity of this compound was >95% with an m/z=478.5. The two fractions containing pure product were combined and evaporated to give product Compound 51 (22.5 mg, 66.4%).

Example 7

Exemplary Compounds

The following analogs in Table 1 below have been prepared. These compounds may be prepared following the procedure for the preparation of Compound 23 (Example 4) and/or Compound 30 (Example 5) using the corresponding dichloroalkanes and the side chain amines identified in the table. These compounds may also be prepared following the procedure for the preparation of Compound 51 (Example 6).

TABLE 1

Exemplary Compounds

| Compound | Structure | Side chain amine |
|---|---|---|
| Compound 1 | (structure) | (amine) |

TABLE 1-continued

Exemplary Compounds

| Compound | Structure | Side chain amine |
|---|---|---|
| Compound 2 | 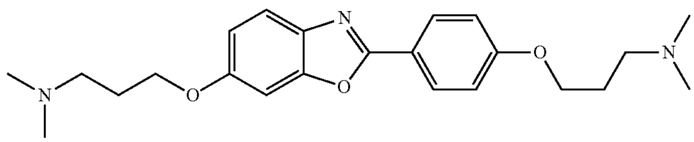 | HN(CH3)2 |
| Compound 3 | 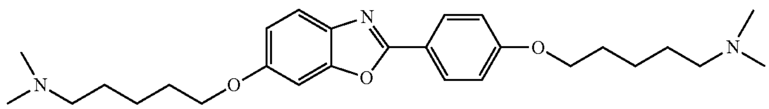 | HN(CH3)2 |
| Compound 4 | 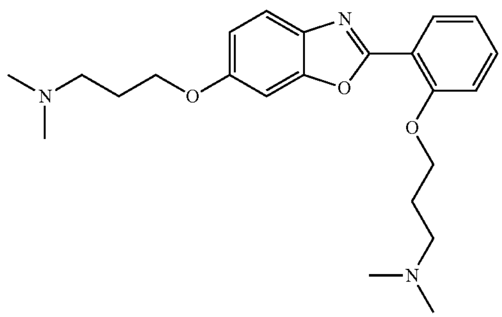 [SMILES: CN(C)CCCOc1ccc2nc(-c3ccccc3OCCCN(C)C)oc2c1] | HN(CH3)2 |
| Compound 5 | 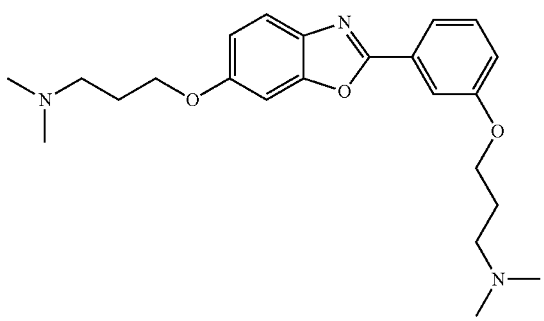 | HN(CH3)2 |
| Compound 6 | 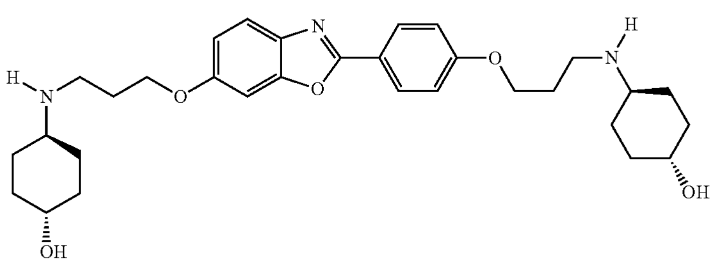 [SMILES: O[C@H]1CC[C@H](NCCCOc2ccc(-c3nc4ccc(OCCCN[C@H]5CC[C@H](O)CC5)cc4o3)cc2)CC1] | trans-4-aminocyclohexanol |
| Compound 7 | 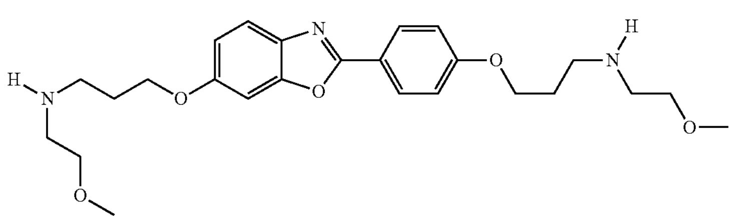 [SMILES: COCCNCCCOc1ccc(-c2nc3ccc(OCCCNCCOC)cc3o2)cc1] | 2-methoxyethylamine |

TABLE 1-continued

Exemplary Compounds

| Compound | Structure | Side chain amine |
|---|---|---|
| Compound 8 | 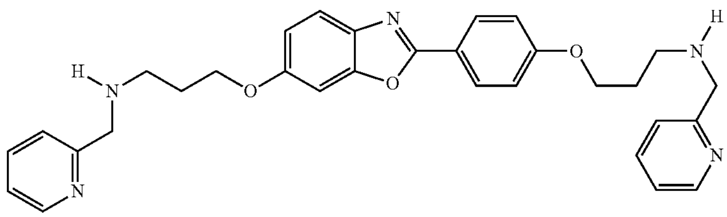 [SMILES: c1ccc(CNCCCOc2ccc(-c3nc4ccc(OCCCNCc5ccccn5)cc4o3)cc2)nc1] | |
| Compound 9 | 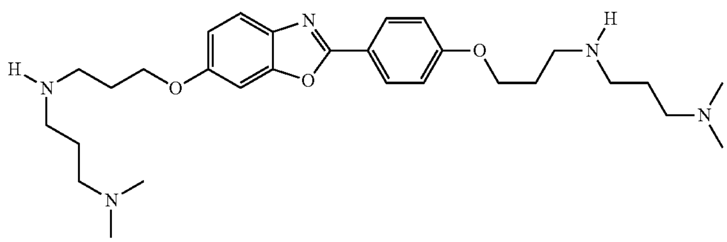 [SMILES: CN(C)CCCNCCCOc1ccc(-c2nc3ccc(OCCCNCCCN(C)C)cc3o2)cc1] | |
| Compound 10 | 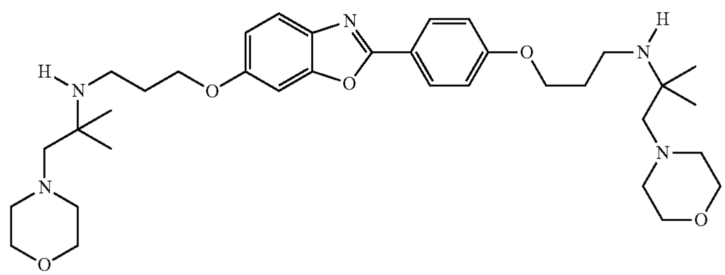 [SMILES: CC(C)(CN1CCOCC1)NCCCOc1ccc(-c2nc3ccc(OCCCNC(C)(C)CN4CCOCC4)cc3o2)cc1] | |
| Compound 11 | 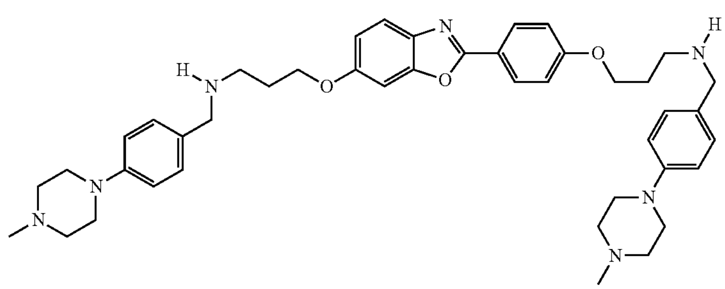 [SMILES: CN1CCN(c2ccc(CNCCCOc3ccc(-c4nc5ccc(OCCCNCc6ccc(N7CCN(C)CC7)cc6)cc5o4)cc3)cc2)CC1] | |
| Compound 12 | 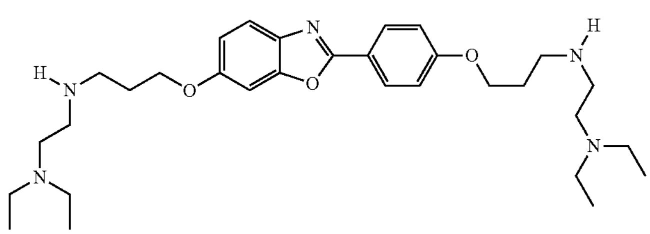 [SMILES: CCN(CC)CCNCCCOc1ccc(-c2nc3ccc(OCCCNCCN(CC)CC)cc3o2)cc1] | |

TABLE 1-continued

Exemplary Compounds

| Compound | Structure | Side chain amine |
|---|---|---|
| Compound 13 | 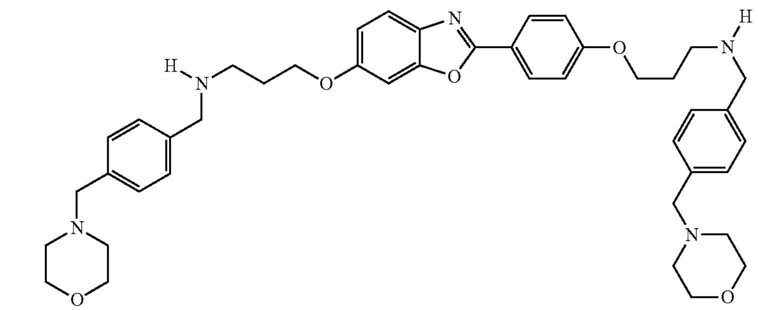 [SMILES: c1cc(CN2CCOCC2)ccc1CNCCCOc1ccc(-c2nc3ccc(OCCCNCc4ccc(CN5CCOCC5)cc4)cc3o2)cc1] | |
| Compound 14 | 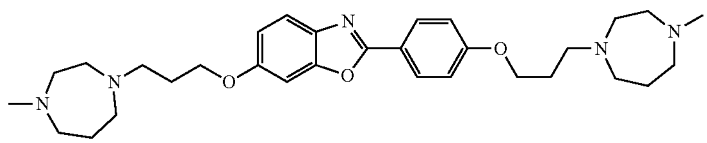 | |
| Compound 15 | 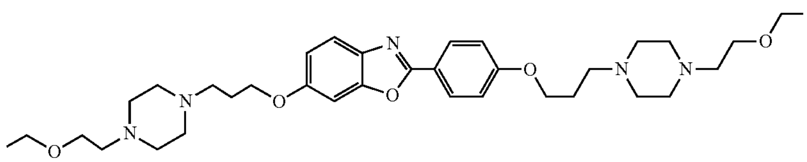 [SMILES: CCOCCN1CCN(CCCOc2ccc(-c3nc4ccc(OCCCN5CCN(CCOCC)CC5)cc4o3)cc2)CC1] | |
| Compound 16 | 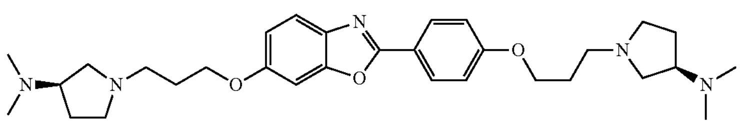 | |
| Compound 17 | 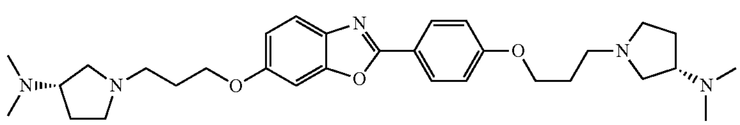 | |
| Compound 18 | 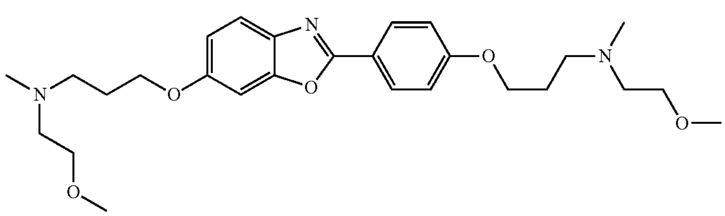 | |
| Compound 19 | 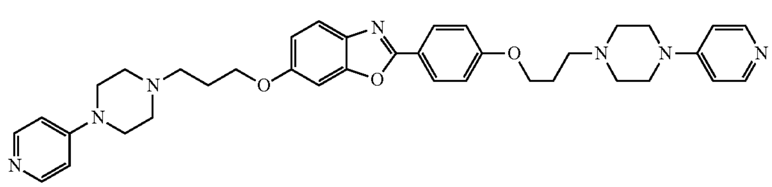 [SMILES: c1cc(N2CCN(CCCOc3ccc(-c4nc5ccc(OCCCN6CCN(c7ccncc7)CC6)cc5o4)cc3)CC2)ccn1] | |
| Compound 20 | 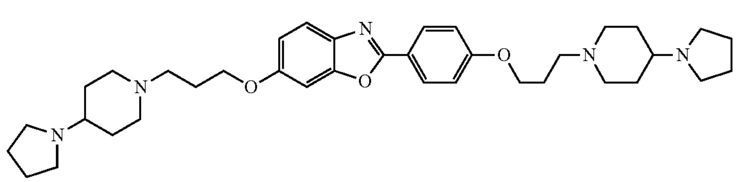 [SMILES: c1cc(-c2nc3ccc(OCCCN4CCC(N5CCCC5)CC4)cc3o2)ccc1OCCCN1CCC(N2CCCC2)CC1] | |

TABLE 1-continued

Exemplary Compounds

| Compound | Structure | Side chain amine |
|---|---|---|
| Compound 21 | 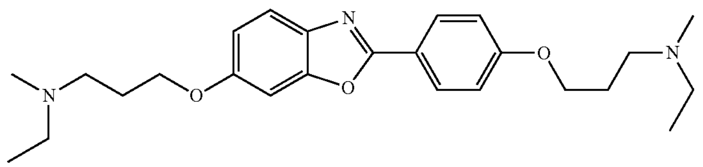 [SMILES: CCN(C)CCCOc1ccc(-c2nc3ccc(OCCCN(C)CC)cc3o2)cc1] | |
| Compound 22 | 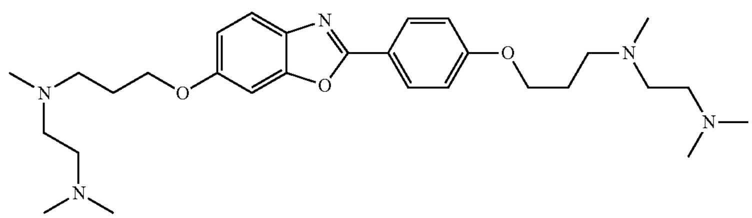 | |
| Compound 23 | 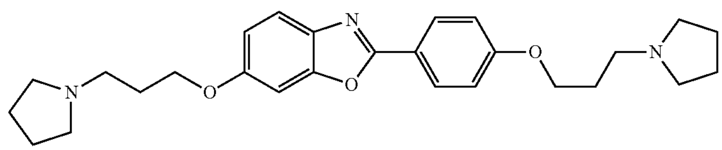 | |
| Compound 24 | 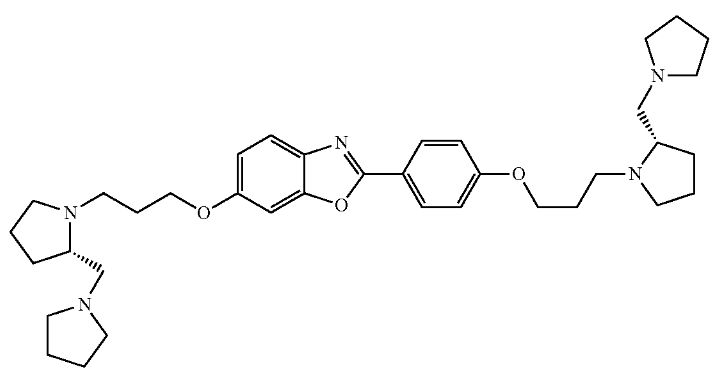 | |
| Compound 25 | 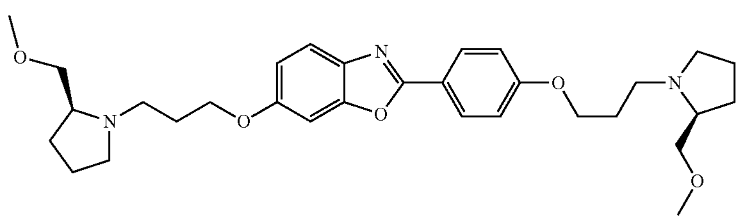 [SMILES: COC[C@@H]1CCCN1CCCOc1ccc(-c2nc3ccc(OCCCN4CCC[C@H]4COC)cc3o2)cc1] | |
| Compound 26 | 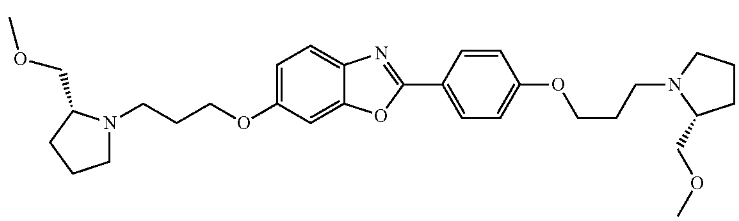 [SMILES: COC[C@H]1CCCN1CCCOc1ccc(-c2nc3ccc(OCCCN4CCC[C@@H]4COC)cc3o2)cc1] | |

TABLE 1-continued

Exemplary Compounds

| Compound | Structure | Side chain amine |
|---|---|---|
| Compound 27 | 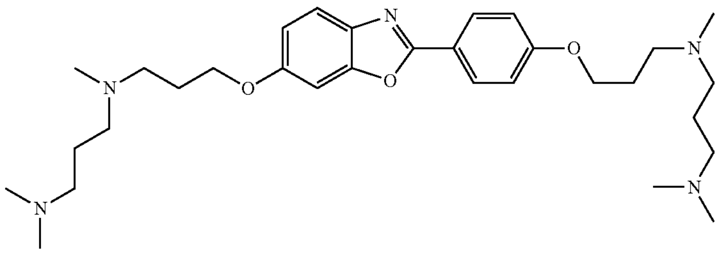 | |
| Compound 28 | 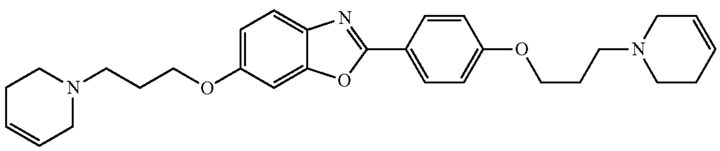 [SMILES: C1=CCN(CCCOc2ccc(-c3nc4ccc(OCCCN5CC=CCC5)cc4o3)cc2)CC1] | |
| Compound 29 | 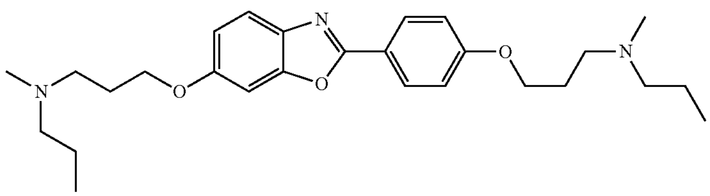 [SMILES: CCCN(C)CCCOc1ccc(-c2nc3ccc(OCCCN(C)CCC)cc3o2)cc1] | |
| Compound 30 | 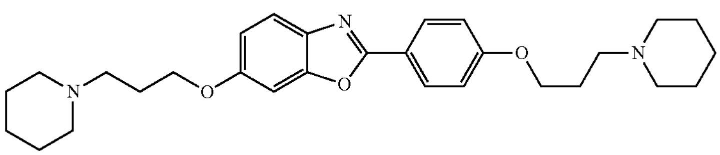 [SMILES: c1cc(-c2nc3ccc(OCCCN4CCCCC4)cc3o2)ccc1OCCCN1CCCCC1] | |
| Compound 31 | 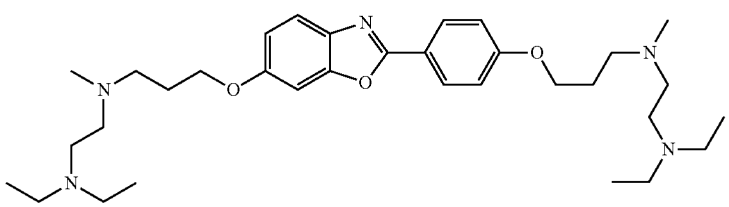 [SMILES: CCN(CC)CCN(C)CCCOc1ccc(-c2nc3ccc(OCCCN(C)CCN(CC)CC)cc3o2)cc1] | |
| Compound 32 | 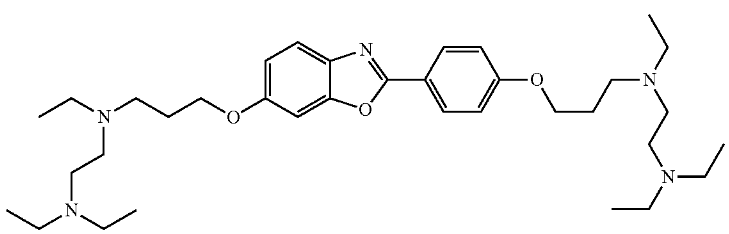 [SMILES: CCN(CC)CCN(CC)CCCOc1ccc(-c2nc3ccc(OCCCN(CC)CCN(CC)CC)cc3o2)cc1] | |
| Compound 33 | 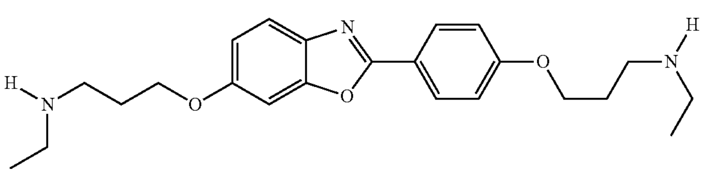 [SMILES: CCNCCCOc1ccc(-c2nc3ccc(OCCCNCC)cc3o2)cc1] | |

TABLE 1-continued

Exemplary Compounds

| Compound | Structure | Side chain amine |
|---|---|---|
| Compound 34 | 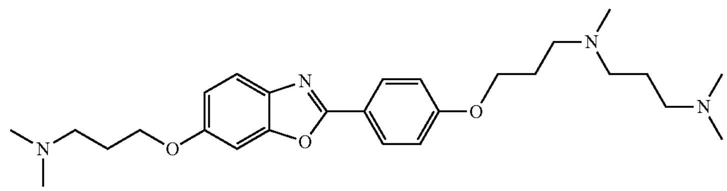 | |
| Compound 35 | 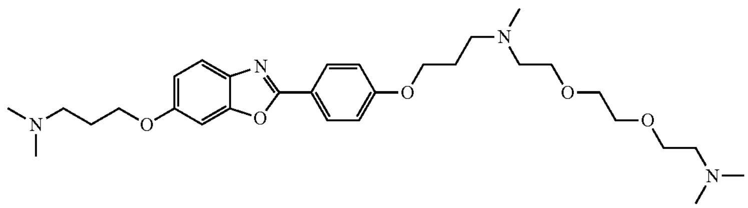 | |
| Compound 36 | 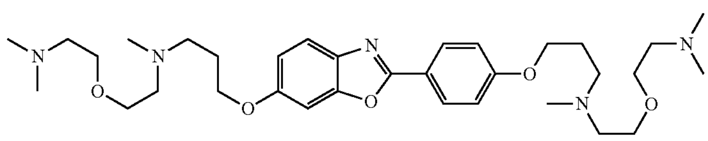 | |
| Compound 37 | 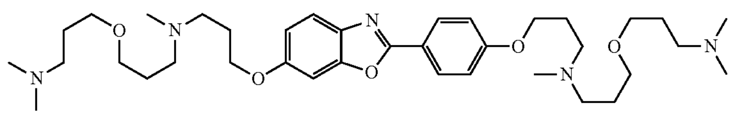 | |
| Compound 38 | 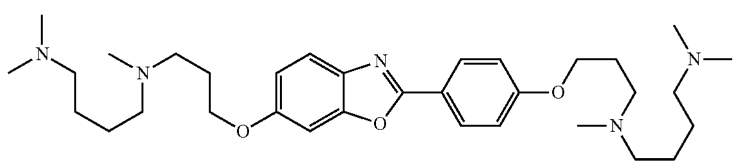 | |

NMR Data for Select Compounds in Table Above:

Compound 1: $^1$H NMR (400 MHz, CD$_3$OD) δ 8.14 (d, J=8.8 Hz, 2H), 7.58 (d, J=8.8 Hz, 1H), 7.33 (d, J=2.4 Hz, 1H), 7.16 (d, J=8.8 Hz, 2H), 7.06 (dd, J=2.2, 8.8 Hz, 1H), 4.28 (m, 4H), 3.10 (m, 4H), 2.68 (s, 6H), 2.57 (s, 6H).

Compound 2: $^1$H NMR (400 MHz, CD$_3$OD) δ 8.14 (d, J=8.8 Hz, 2H), 7.59 (d, J=8.8 Hz, 1H), 7.30 (d, J=2.4 Hz, 1H), 7.15 (d, J=8.8 Hz, 2H), 7.04 (dd, J=2.4, 8.8 Hz, 1H), 4.21 (m, 4H), 3.34 (m, 4H), 2.93 (s, 6H), 2.92 (s, 6H), 2.68 (s, 6H), 2.26 (m, 4H).

Compound 3: $^1$H NMR (400 MHz, CD$_3$OD) δ 8.15 (d, J=8.8 Hz, 2H), 7.55 (d, J=8.8 Hz, 1H), 7.24 (d, J=2.4 Hz, 1H), 7.10 (d, J=8.8 Hz, 2H), 6.98 (dd, J=2.4, 8.8 Hz, 1H), 4.10 (m, 4H), 3.25 (m, 4H), 1.90 (m, 4H), 1.78 (m, 4H), 1.59 (m, 4H).

Compound 4: $^1$H NMR (400 MHz, CD$_3$OD) δ 8.18 (dd, J=1.6, 8.0 Hz, 1H), 7.72 (d, J=9.0 Hz, 1H), 7.60 (m, 1H), 7.37 (d, J=2.4 Hz, 1H), 7.30 (d, J=8.4 Hz, 1H), 7.21 (dd, J=7.2, 8.0 Hz, 1H), 7.09 (dd, J=2.6, 9.0 Hz, 1H) 4.39 (t, J=5.6 Hz, 2H), 4.20 (t, J=5.8 Hz, 2H), 3.22 (dd, J=7.6, 8.4 Hz, 2H), 3.05 (s, 6H), 2.82 (s, 6H), 2.38 (m, 2H), 2.23 (m, 2H).

Compound 5: $^1$H NMR (400 MHz, CD$_3$OD) δ 7.79 (d, J=8.0 Hz, 1H), 7.75 (dd, J=1.6, 2.4 Hz, 1H), 7.63 (d, J=8.8 Hz, 1H), 7.50 (dd, J=8.0, 8.0 Hz, 1H), 7.32 (d, J=2.4 Hz, 1H), 7.18 (dd, J=2.6, 8.6 Hz, 1H), 7.06 (dd, J=2.4, 8.8 Hz, 1H) 4.21 (m, 4H), 3.32 (m, 4H), 2.91 (s, 6H), 2.90 (s, 6H), 2.25 (m, 4H).

Compound 20: $^1$H NMR (400 MHz, CD$_3$OD) δ 8.10 (d, J=8.8 Hz, 2H), 7.55 (d, J=8.8 Hz, 1H), 7.25 (d, J=2.4 Hz, 1H), 7.10 (d, J=8.8 Hz, 2H), 6.99 (dd, J=2.4, 8.8 Hz, 1H), 4.12 (m, 4H), 3.04 (bd, J=10.8 Hz, 4H), 2.66 (bs, 8H), 2.57 (m, 4H), 2.15-1.90 (m, 14H), 1.82 (m, 8H), 1.60 (m, 4H).

Compound 27: $^1$H NMR (400 MHz, CD$_3$OD) δ 8.13 (d, J=9.2 Hz, 2H), 7.58 (d, J=8.8 Hz, 1H), 7.29 (d, J=2.4 Hz, 1H), 7.13 (d, J=9.2 Hz, 2H), 7.03 (dd, J=2.2, 8.6 Hz, 1H), 4.20 (m, 4H), 3.60-3.10 (m, 12H), 2.98 (s, 6H), 2.93 (s, 12H), 2.25 (m, 8H).

Compound 35: $^1$H NMR (400 MHz, CD$_3$OD) δ 8.10 (d, J=8.8 Hz, 2H), 7.55 (d, J=8.8 Hz, 1H), 7.25 (d, J=2.4 Hz, 1H), 7.10 (d, J=8.8 Hz, 2H), 6.99 (dd, J=2.4, 8.8 Hz, 1H), 4.10 (m, 4H), 3.60 (m, 8H), 2.65 (m, 8H), 2.35 (m, 18H), 2.02 (m, 4H).

Compound 36: $^1$H NMR (400 MHz, CD$_3$OD) δ 8.14 (d, J=8.8 Hz, 2H), 7.55 (d, J=8.8 Hz, 1H), 7.30 (d, J=2.4 Hz, 1H), 7.13 (d, J=8.8 Hz, 2H), 7.03 (dd, J=2.4, 8.8 Hz, 1H), 4.22 (m, 4H), 3.92 (bs, 4H), 3.87 (m, 4H), 3.60-3.20 (m, 12H), 3.00 (s, 6H), 2.92 (s, 12H), 2.30 (m, 4H).

Compound 37: $^1$H NMR (400 MHz, CD$_3$OD) δ 8.14 (d, J=8.8 Hz, 2H), 7.59 (d, J=8.8 Hz, 1H), 7.31 (d, J=2.4 Hz, 1H), 7.15 (d, J=8.8 Hz, 2H), 7.04 (dd, J=2.4, 8.8 Hz, 1H), 4.23 (m, 4H), 3.58 (m, 8H), 3.55-3.35 (m, 6H), m 3.23 (m, 6H), 2.96 (s, 6H), 2.90 (m, 12H), 2.30 (m, 4H), 2.05 (m, 8H).

Compound 38: $^1$H NMR (400 MHz, CD$_3$OD) δ 8.13 (d, J=8.8 Hz, 2H), 7.58 (d, J=8.8 Hz, 1H), 7.29 (d, J=2.0 Hz, 1H), 7.13 (d, J=8.8 Hz, 2H), 7.02 (dd, J=2.4, 8.8 Hz, 1H), 4.20 (m, 4H), 3.30-3.50 (m, 4H), 3.18 (m, 6H), 2.85-2.96 (m, 18H), 2.28 (m, 4H), 1.82 (m, 6H).

Example 8

Synthesis of Compound 34

MHz, CD$_3$OD) δ 8.09 (d, J=9.1 Hz, 2H), 7.47-7.4 (m, 6H), 7.16 (d, J=9.1 Hz, 2H), 7.02 (d, J=2.4 Hz, 1H), 7.02 (dd, J=2.4, 8.5 Hz, 1H), 5.18 (s, 2H); MS (ES$^-$) m/z 316.4.

A mixture of Compound 42 (1.77 g, 5.58 mmol), 1-bromo-3-chloropropane (1.6 mL, 17 mmol) and potassium carbonate (2.7 g, 20 mmol) in 10 mL DMSO at room temperature was stirred for 2.5 hours until the reaction was completed by TLC. The reaction was quenched by addition of water and then extracted five three times with EtOAc. The combined organic phase was dried over Na$_2$SO$_4$, filtered and concentrated. The residue was crystallized from ethyl acetate-hexane to give Compound 43 as a light solid (1.93 g, 88%).

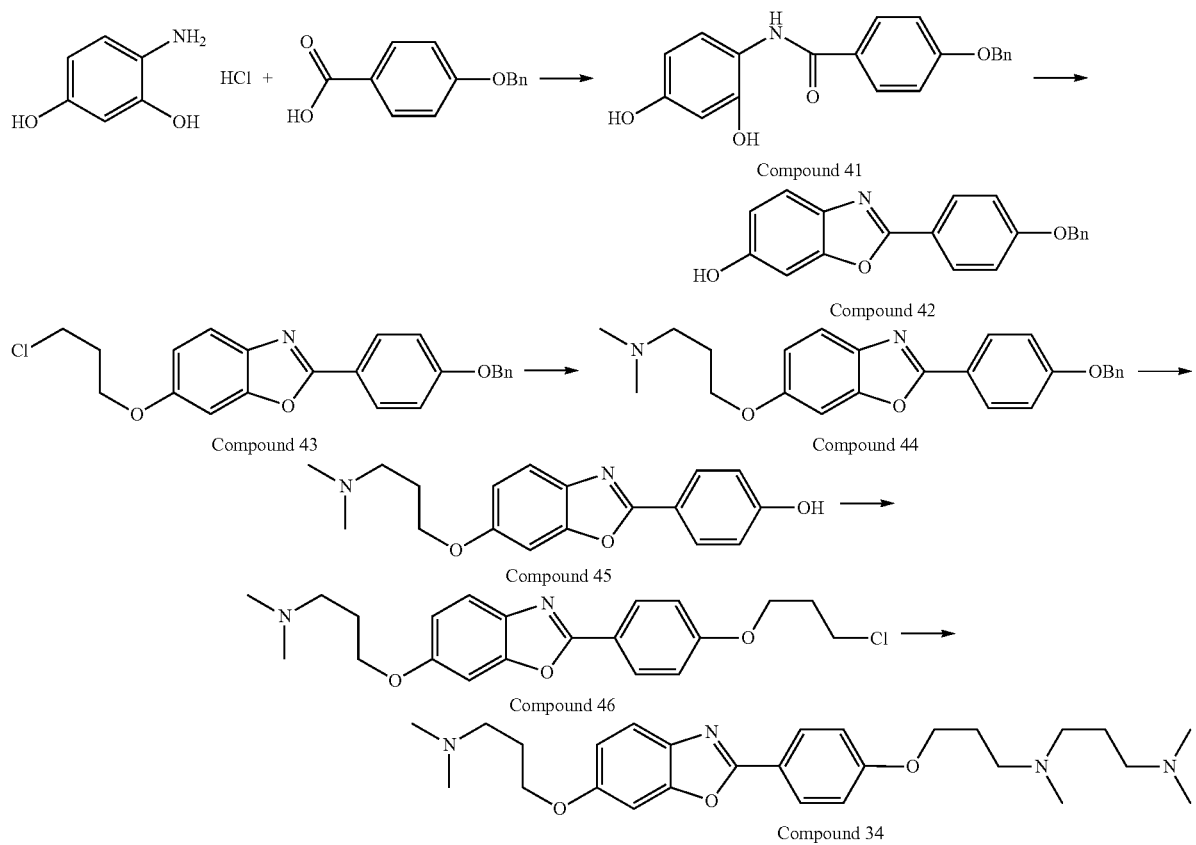

Compound 34. Referring to the scheme above, a mixture of 4-aminoresorsinol hydrochloride (5.3 g, 33 mmol), 4-benzyloxybenzoic acid (5.0 g, 22 mmol), 1-hydroxybenzotriazole (5.9 g, 44 mmol), benzotriazole-1-yl-oxytripyrrolidinophosphonium hexafluorophosphate (23 g, 44 mmol) and N,N-diisopropylethylamine (19 mL, 110 mmol) in dimethylformamide (DMF) (50 mL) was stirred at 0° C. to room temperature overnight. After concentration to remove DMF, the reaction mixture was purified by silica gel chromatography (20% to 80% EtOAc/hexane, EtOAc and 30% MeOH/EtOAc) to give desired amide Compound 41 (or/and ester, 7.3 g, 95%).

A solution of Compound 41 (7.3 g, 22 mmol) in acetic acid (90 mL) was heated at 120° C. for 3 hours. The reaction mixture was cooled to room temperature and concentrated. The residue was purified by silica gel chromatography (10% to 30% EtOAc/hexanes) to give the desired product Compound 42 (2.0 g, 29%) as light yellow solid. $^1$H NMR (400

To a suspension of Compound 43 (1.10 g, 2.8 mmol) in 40 mL of ethanol was added 5 mL of dimethylamine at −78° C. The mixture was sealed in a sealed tube and heated at 100° C. for 10 hours. The mixture was concentrated to give Compound 44 (1.1 g, 98%). The product was carried on to next step reaction.

A mixture of Compound 44 (1.1 g, 2.7 mmol) and palladium hydroxide (7 mg) in 32 mL of methanol and 5 mL of dichloromethane was stirred under a hydrogen balloon at room temperature over night. The mixture was filtered through celite and the filtrate was concentrated to give crude product Compound 45. Assuming a theoretical yield of 0.85 and the product was carried on to the next step directly without further purification.

A mixture of Compound 45 (200 mg, 0.64 mmol), 1-bromo-3-chloropropane (0.32 mL, 3.2 mmol) and potassium carbonate (470 mg, 3.4 mmol) in 4 mL DMSO at room temperature was stirred for 2 hours until the reaction was completed by TLC. The reaction was quenched by addition of water and then extracted four times with EtOAc. The combined organic phase was dried over $Na_2SO_4$, filtered and concentrated. The residue was purified by preparative TLC (4% $Et_3N$ in 5% MeOH/THF) to give Compound 46 (170 mg, 68%).

A mixture of Compound 46 (30 mg, 0.08 mmol), N,N,N'-trimethyl-1,3-propane-diamine (50 mg, 0.43 mmol) in 2 mL of ethanol under a sealed tube was heated at 100° C. for 10 hours. The mixture was concentrated and the residue was purified by HPLC to give 8 mg of Compound 34 as a white solid (8 mg, 20%). $^1$H NMR (400 MHz, $CD_3OD$) δ 8.10 (d, J=8.8 Hz, 2H), 7.55 (d, J=8.8 Hz, 1H), 7.25 (d, J=2.3 Hz, 1H), 7.10 (d, J=8.8 Hz, 2H), 7.00 (dd, J=2.3, 8.8 Hz, 1H), 4.14 (t, J=5.9 Hz, 2H), 4.10 (t, J=6.2 Hz, 2H), 2.69 (m, 4H), 2.56 (m, 4H), 2.39 (s, 12H), 2.36 (s, 3H), 2.04 (m, 4H), 1.77 (m, 2H); MS ($ES^-$) m/z+H 469.55.

Example 9

In Vitro Biological Activity

A. Primary Assay. The primary assay involved transfecting human embryonic kidney epithelial (HEK) cells with TLR9. More specifically, HEK293 fibroblast cells (ATCC No. CRP-1573, American Type Culture Collection, Manassas, Va.) were transfected with pcDNA3.1D/V5-His-TOPO® plasmid (Invitrogen, Carlsbad, Calif.) encoding human TLR9 (directly inserted as a Tag polymerase-amplified PCR product) and firefly luciferase under the control of three NF-kB binding sites contained in the E-selectin-1 promoter, which was cloned into a pGL3-Enhancer Vector (Promega Corp, Madison, Wis.). The compounds tested in this assay are listed in Table 1, below. Each compound was added to cells 30 min. before stimulation with Oligo CpG 2006, a synthetic phosphorothioate oligonucleotide (Hartmann et al., J Immunol. 164:1617-24 (2000)), with nucleotide sequence 5'-TCG TCG TTT TGT CGT TTT GTC GTT-3' (SEQ ID NO:1). The cells were incubated overnight at 37° C. The luciferase substrate Steady-Glo® (Promega) was added to the wells, and luminescence was measured to determine the extent of TLR9-driven gene activation. The luminescence data was used to calculate an $IC_{50}$ for each sample. The $IC_{50}$ is defined as the concentration of compound that suppresses the luminescence to 50% of that observed in the absence of compound, in other words, with full stimulation. The results of this assay are shown in Table 2, below. The $IC_{50}$ of the Comparator was found to be 0.16 micromolar. The $IC_{50}$ for Compound 1 was found to be 0.06 micromolar and the $IC_{50}$ for the remaining compounds was less than 0.04 micromolar.

B. Secondary Assays.

(1) HEK/TLR7Activation Assay: The same compounds were tested in the same way as the primary assay with the following differences. The plasmid used to transfect the HEK cell line encoded for human TLR7 instead of TLR9, and R848 was used to stimulate the cells instead of Oligo CpG 2006. The results of this assay are also shown in Table 2. For each compound tested the $IC_{50}$ from the HEK/TLR9 activation assay, above, was significantly lower than the $IC_{50}$ from the HEK/TLR7 assay, indicating a greater specificity for TLR9 than for TLR7.

(2) Splenocyte CpG 1668 Assay: Some of the compounds tested in the primary assay were also assayed for suppression of mouse spleen IL-6 production in response to stimulation with Oligo CpG 1668, a synthetic phosphorothioate oligonucleotide (Krieg et al. Nature. 374:546-9 (1995)), with nucleotide sequence 5'-TCC ATG ACG TTC CTG ATG CT-3' (SEQ ID NO:2). Each compound was added to dissociated splenocytes before addition of stimulatory oligonucleotide. Cells were stimulated in culture for 72 hrs and the supernatant was removed for ELISA analysis of IL-6 level. Here the $IC_{50}$ is defined as the concentration of compound that suppresses cytokine production to 50% of that observed in the absence of compound, i.e., full stimulation. All compounds that were tested, except the comparator, inhibited stimulation of mouse splenocytes with an $IC_{50}$ below 1 μM. The results of this assay are shown in Table 2, below.

(3) Spleen CT Glo Assay: To determine if compounds had adverse effects on living cells, dissociated mouse splenocytes were incubated with some of the compounds for 72 hours. At the end of the incubation Celliter-Glo™ reagent (Promega Corporation, Madison, Wis.) was added and luminescence was read per manufacturer's instructions. This reagent measures ATP as an indication of cell metabolism. Dead cells will not produce signal. $IC_{50}$ is defined as the concentration of compound that suppresses viability to 50% of that observed in the absence of compound. The few compounds that measurably affected viability did so at concentrations far above those that affected cytokine release in response to TLR9 stimulation. The results are shown in Table 2. These results indicate that the TLR9 suppression was not due to cell death or weakness.

(4) PBMC CpG 2216 Assay: A subset of compounds tested as described above were also assayed for suppression of human peripheral blood mononuclear cells (PBMC) α-interferon response to stimulation with Oligo CpG 2216, a synthetic oligo phosphorothioate/phosphodiester oligonucleotide (Vollmer et al. Eur J. Immunol. 34:251-62 (2004)), with nucleotide sequence 5'-ggG GGA CGA CGT CGt ggg gG-3' (small letters indicate phosphorothioate linkages, all others are phosphodiester) (SEQ ID NO:3). Each compound was added to Ficoll-Paque™ (GE Healthcare, UK) to separate mononuclear cells from healthy volunteer donors before addition of stimulatory oligonucleotide. Cells were stimulated in culture for 72 hrs and the supernatant was removed for ELISA analysis of α-interferon level was performed using a VeriKine™ Human IFN-Alpha ELISA kit (Pestka Biomedical Laboratories, N.J.). All the compounds tested in this assay inhibited stimulation of human PBMC with an $IC_{50}$ below 1 μM.

Table 2 below shows the compounds tested and results obtained from each of the assays described and discussed above.

TABLE 2

In Vitro Assay Results

| Compound Number | HEK/ TLR9 $IC_{50}$ (μM) | HEK/ TLR7 $IC_{50}$ (μM) | Splenocyte CpG 1668 $IC_{50}$ (μM) | Spleen CellTiter-Glo $IC_{50}$ (μM) | PBMC CpG2216 $IC_{50}$ (μM) |
|---|---|---|---|---|---|
| Comparator | 0.160 | 2.69 | 1.02 | | |
| Compound 1 | 0.031 | 7.80 | 0.29 | | |
| Compound 2 | 0.0154 | 2.21 | 0.048 | >10 | 0.5 |
| Compound 3 | 0.0230 | 1.4 | | | |
| Compound 4 | 0.0120 | 1.8 | | | |
| Compound 5 | 0.0110 | 2.0 | | | |
| Compound 6 | 0.0202 | 8.41 | | | |
| Compound 7 | 0.0233 | 1.31 | | >10 | |
| Compound 8 | 0.0197 | 1.23 | | 7.82 | |
| Compound 9 | 0.12 | 9.05 | | | |
| Compound 10 | 0.0153 | 0.35 | 0.026 | 9.8 | |
| Compound 11 | 0.0048 | 0.47 | 0.002 | 10 | 0.6 |
| Compound 12 | 0.0058 | 0.78 | 0.004 | >10 | 0.5 |
| Compound 13 | 0.0071 | 0.46 | 0.003 | 7.07 | |

TABLE 2-continued

In Vitro Assay Results

| Compound Number | HEK/ TLR9 IC$_{50}$ (μM) | HEK/ TLR7 IC$_{50}$ (μM) | Splenocyte CpG 1668 IC$_{50}$ (μM) | Spleen CellTiter- Glo IC$_{50}$ (μM) | PBMC CpG2216 IC$_{50}$ (μM) |
|---|---|---|---|---|---|
| Compound 14 | 0.0056 | 0.62 | 0.004 | >10 | |
| Compound 15 | 0.0232 | 2.24 | | >10 | |
| Compound 16 | 0.0055 | 0.43 | 0.008 | >10 | 0.4 |
| Compound 17 | 0.0053 | 0.17 | 0.006 | >10 | |
| Compound 18 | 0.0192 | 1.40 | | 9.9 | |
| Compound 19 | 0.0276 | 1.10 | | 10 | |
| Compound 20 | 0.0125 | 1.82 | 0.006 | >10 | 0.7 |
| Compound 21 | 0.0133 | 1.24 | | 9.58 | |
| Compound 22 | 0.0087 | 0.50 | 0.010 | 7.11 | |
| Compound 23 | 0.0111 | 1.55 | 0.018 | >10 | 0.6 |
| Compound 24 | 0.0064 | 0.60 | 0.008 | >10 | |
| Compound 25 | 0.0182 | 0.90 | 0.048 | >10 | |
| Compound 26 | 0.0124 | 0.99 | 0.042 | >10 | |
| Compound 27 | 0.0034 | 0.98 | 0.004 | 8.96 | |
| Compound 28 | 0.0125 | 1.55 | | >10 | |
| Compound 29 | 0.0193 | 0.78 | 0.042 | 10.39 | |
| Compound 30 | 0.0121 | 1.14 | 0.025 | >10 | 0.5 |
| Compound 31 | 0.0072 | 0.44 | 0.006 | >10 | 0.2 |
| Compound 32 | 0.0096 | 0.58 | 0.010 | >10 | |
| Compound 33 | 0.100 | 8.52 | | | |
| Compound 34 | 0.004 | 0.8 | | | |
| Compound 35 | 0.029 | 1.4 | 0.04 | | |
| Compound 36 | 0.038 | >2.5 | | | |
| Compound 37 | 0.030 | >2.5 | | | |
| Compound 38 | 0.034 | >2.5 | | | |

Example 10

In Vivo Biological Activity

Short Term CpG Stimulation

Short Term CpG Stimulation Assay: Compounds identified as having potency in the HEK/TLR9 and splenocyte CpG 1668 assays described in Example 9, above, were tested in an in vivo short term CpG stimulation assay. Mice were orally administered compound in water, and challenged within 90 minutes by subcutaneous (s.c.) injection of 30 micrograms of oligo CpG 1668. Two hours later serum was taken and assayed for IL-6 using ELISA analysis. The results of this assay are shown in Table 3, below. Results from assays repeated on different dates are set forth as multiple numbers separated by commas.

TABLE 3

CpG Stimulation Assay

| Compound number | Percent short-term IL-6 suppression |
|---|---|
| Comparator | 7, 32 |
| Compound 13 | 40, 44 |
| Compound 14 | 0 |
| Compound 16 | 50, 45 |
| Compound 20 | 0 |
| Compound 22 | 36 |
| Compound 23 | 91, 75 |
| Compound 26 | 81, 69 |
| Compound 27 | 30 |
| Compound 30 | 93, 79 |
| Compound 34 | 26 |
| Compound 35 | 38 |

Table 3 shows that at least 69% suppression of IL-6 was observed 1.5 hours after oral administration of 20 mg/kg Compound 23, Compound 30, or Compound 26. At least 75% suppression of IL-6 was observed after oral administration of Compound 23 and Compound 30. No suppression was observed after administration of two of the compounds tested, Compound 14 and Compound 20, despite the high levels of suppression exhibited in the in vitro assays described above. The remaining compounds exhibited varying levels of IL-6 suppression.

Example 11

In Vivo Biological Activity

Lymph Node Response

Two compounds assayed as described in Example 10 above, Compound 23 and Compound 30, showed a particularly high level of suppression. Mice were orally administered one of those two compounds or hydroxychloroquine ("HCQ") at either 20 mg/kg or 60 mg/kg daily for two weeks. After in vivo dosing, lymph nodes were removed and stimulated in vitro with CpG 1668 at 1 μg/ml for 72 hrs, after which supernatants were removed and assayed by ELISA for IL-6. Results of this assay are shown in FIG. 1. Levels of dosing are indicated after each compound name appearing in the Figure.

The results in FIG. 1 show that both Compound 2 and Compound 23 suppressed IL-6 release in the lymph nodes, and Compound 23 showed particularly high levels of suppression even upon administration of only 20 mg/kg.

Example 12

In Vivo Biological Activity

Spontaneous Lupus Models

A. MRL/MpJ-faslpr/J Experiment 1.

Figure 2:
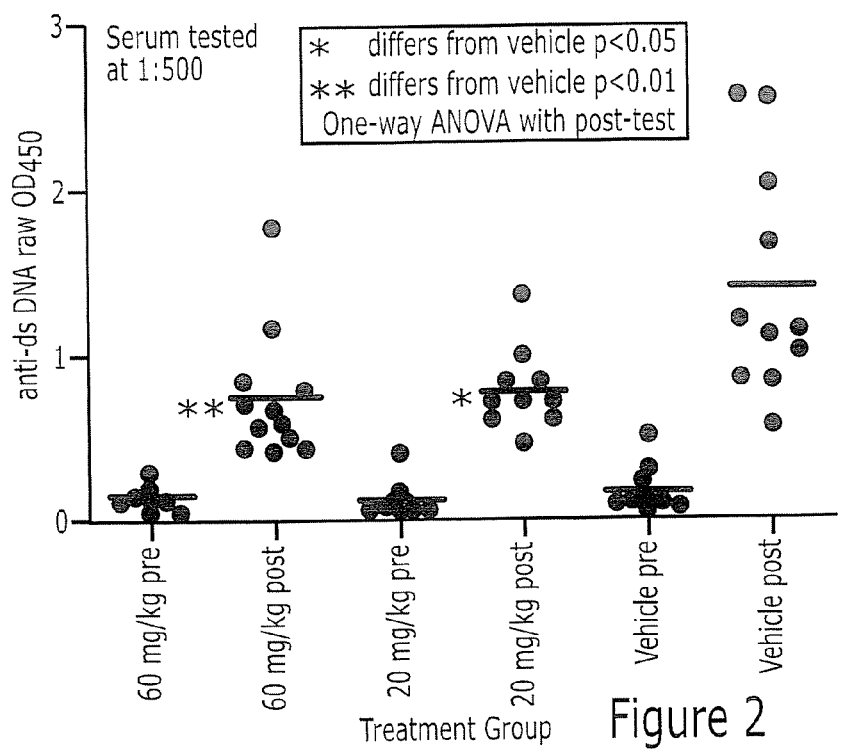
FIG. 2 is a plot showing the results of optical density measurements at 450 nanometers (OD$_{450}$) in an ELISA assay of mouse anti-dsDNA, before and after 7 weeks of dosing of MRL/MpJ-faslpr/J ("MRL/lpr") mice with 20 mg/kg or 60 mg/kg of Compound 23, as described in Example 12A.
Figure 3A:
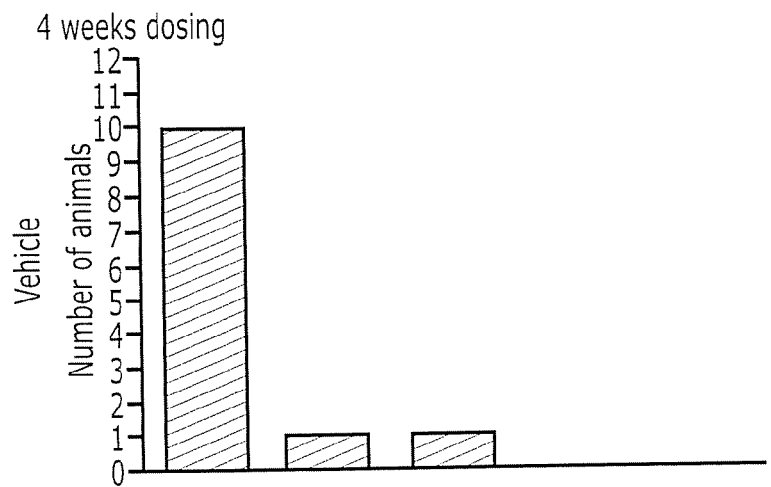
FIG. 3 is a set of bar graphs showing the results of antinuclear antibodies (ANA) testing in the MRL/lpr spontaneous lupus model of mice administered 20 mg/kg or 60 mg/kg of Compound 23 after 4, 10 or 12 weeks of dosing, as described in Example 12A. The results are shown as the number of mice scored in each of five possible categories of ANA results (−, −/+, 0, +, or ++).
Figure 3B:
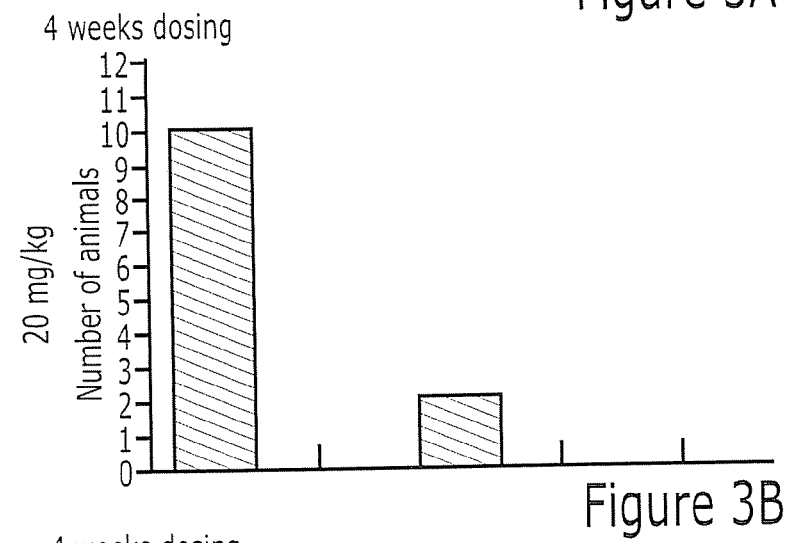
Figure 3C:
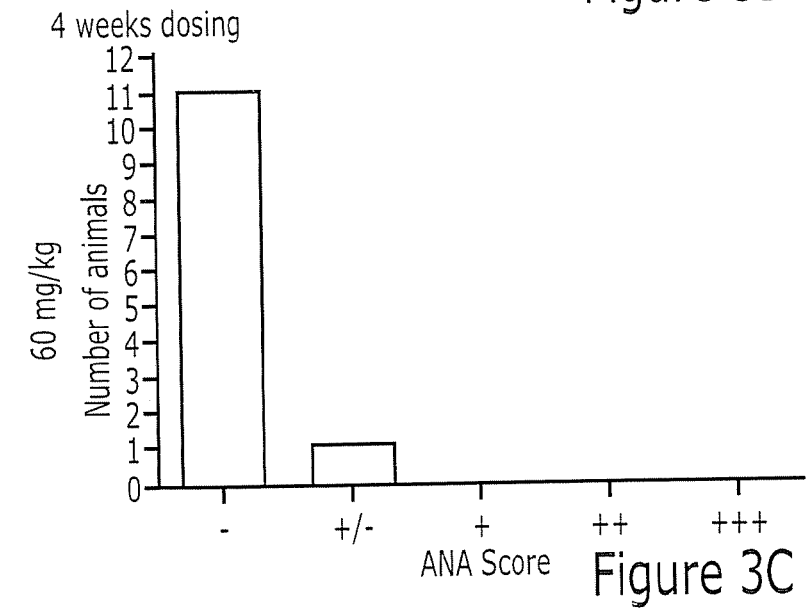
Figure 3D:
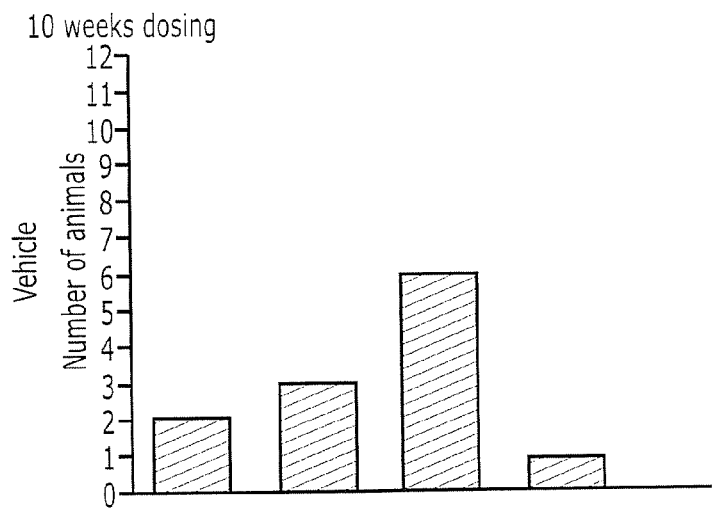
Figure 3E:
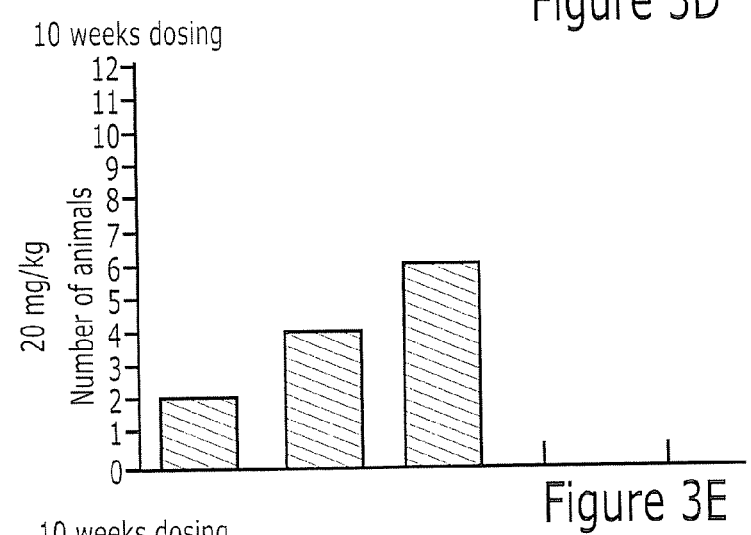
Figure 3F:
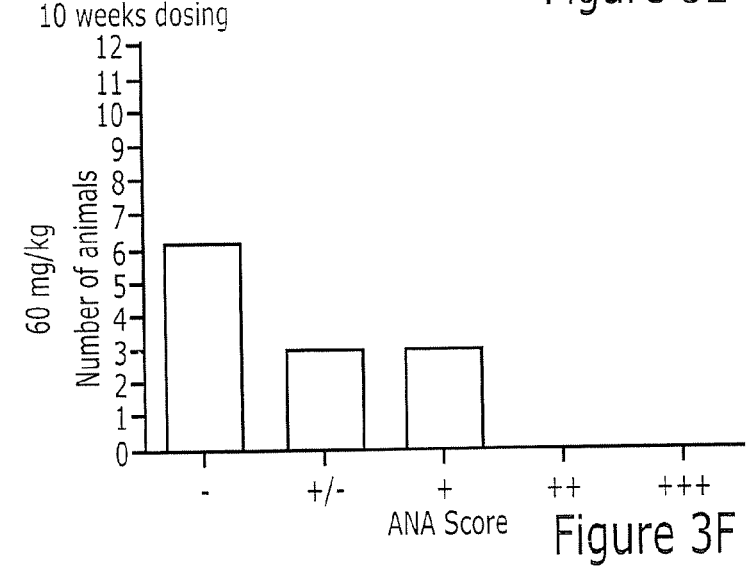
Figure 3G:
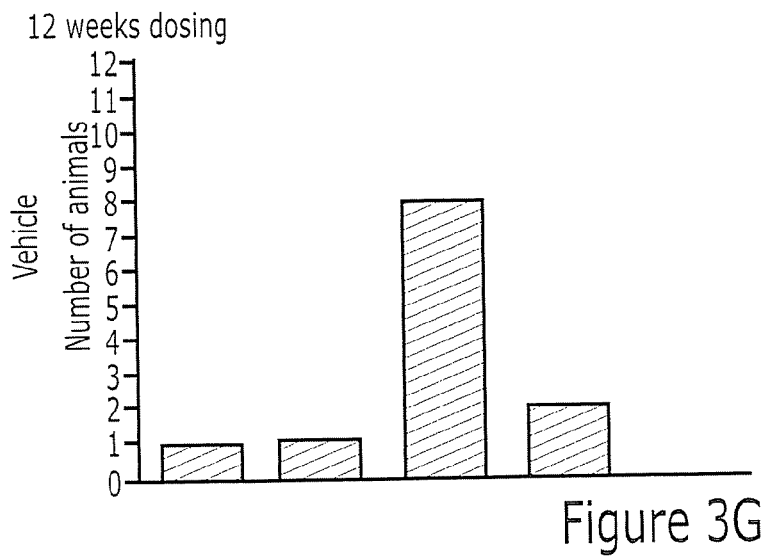
Figure 3H:
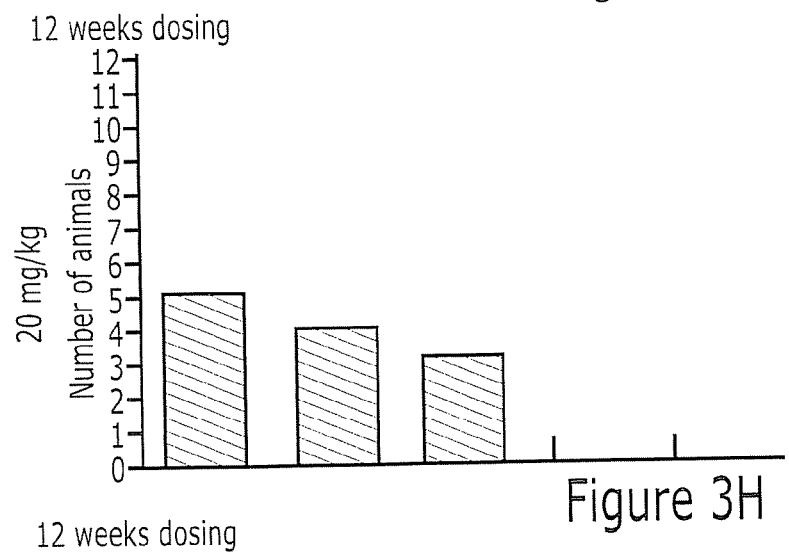
Figure 3I:
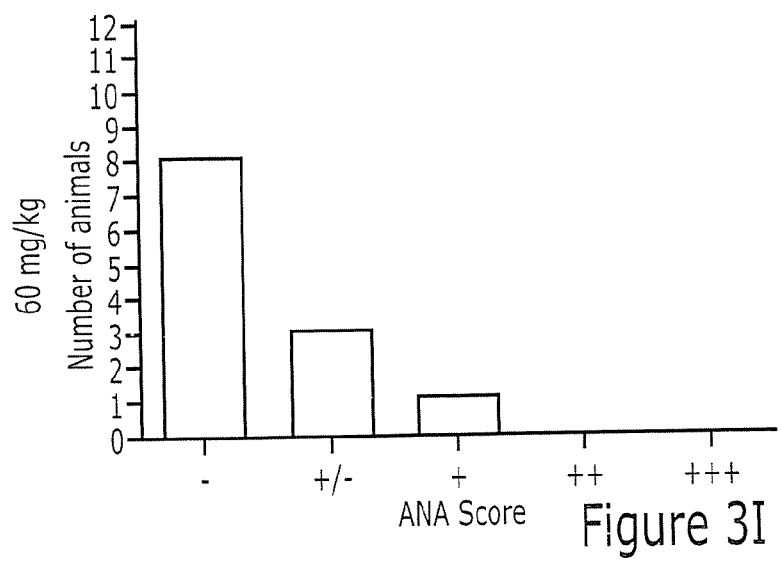

In this experiment, MRL/MpJ-faslpr/J mice ("MRL/lpr") obtained from Jackson Laboratories were dosed orally with Compound 23 at 20 or 60 mg/kg in water. MRL/lpr mice have a defect in lymphocyte death and spontaneously develop autoantibodies including the anti-nuclear antibodies found in human systemic lupus erythematosus (SLE). Dosing was performed daily five days a week beginning at 5 weeks of age. Blood and urine samples were taken prior to dosing on day one and every three to four weeks thereafter. An ELISA assay was used to measure serum anti-dsDNA before and after 7 weeks of dosing. The assay was conducted using a Mouse Anti-dsDNA Total Ig Qualitative ELISA kit (Alpha Diagnostic International, San Antonio. TX). The results are shown in FIG. 2. FIG. 2 shows that there was a dose-titrating effect on this autoantibody, with statistically significant suppression of the mean Optical Density at 450 nm (OD$_{450}$) versus vehicle-dosed animals. The statistical difference was still observed at 10 weeks of dosing, but then compound-treated groups became more similar to vehicle-treated animals dosed with dH$_2$O, given orally, at 12 weeks and beyond. No evidence of dosage-related toxicity was seen as judged by general appearance or body weight measurements.

Anti-nuclear antibodies ("ANA") in this experiment were also examined by exposing fixed HepG2 cells, obtained as fixed samples on slides from Antibodies Inc., to diluted serum from the mice dosed with Compound 23 at 20 or 60 mg/kg, as described above, and staining for mouse immunoglobulin using the kit reagents supplied by Antibodies Inc. according to the kit instructions. Intensity of fluorescent staining was then read by microscope, and scores were assigned values between − and +++. Sample identifications were blinded for data collection.

FIG. 3 is a graphic illustration of the results of the ANA testing. FIG. 3 shows that there was a dose-dependent suppression of ANA development, in that vehicle-treated mice gradually became ANA positive between 5 and 12 weeks of age, while sera from compound treated mice showed much slower progression to positive ANA staining.

B. MRL/lpr Experiment 2.

Figure 4:
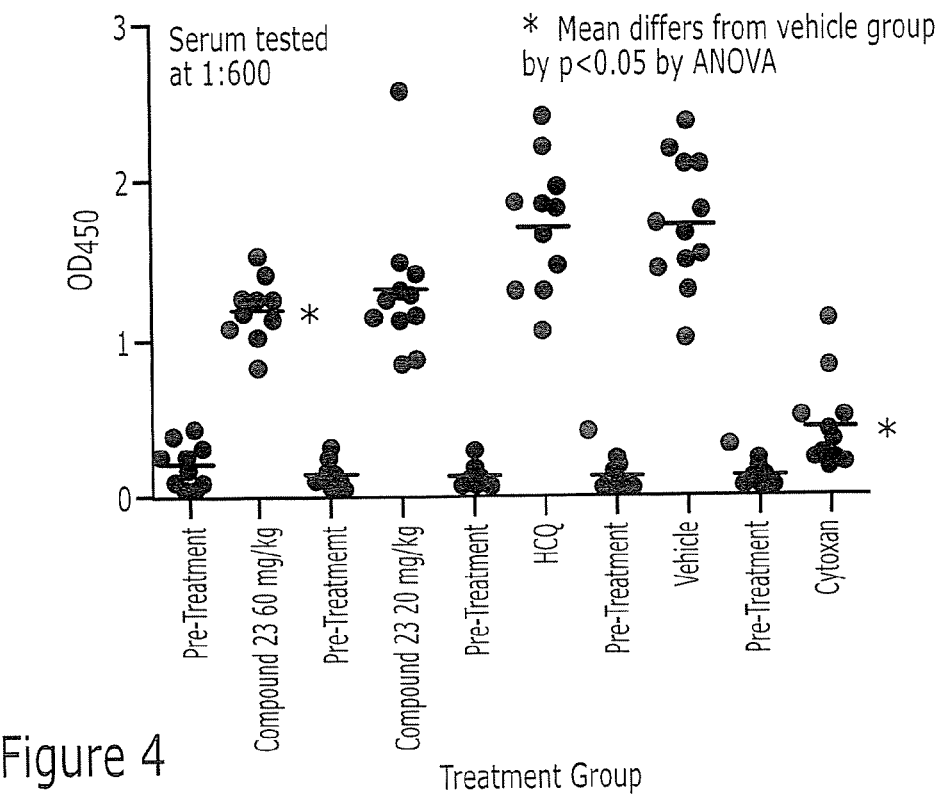
FIG. 4 is a graph showing results of an ELISA assay at OD$_{450}$ of MRL/lpr mouse anti-dsDNA pre- and post-dosing for 12 weeks with Compound 23 (20 mg/kg or 60 mg/kg), HCQ, or cyclophosphamide, as described in Example 12B.

In this SLE experiment, dosing, groups were as described in Table 4 below. Two dose levels of Compound 23 were compared to HCQ and cyclophosphamide (Cytoxan®). HCQ and cyclophosphamide are currently used in the treatment of cutaneous and systemic lupus, respectively. Cyclophosphamide showed consistent suppression of serum anti-dsDNA levels. This difference was statistically significant at the 8 and 12 week dosing points, when tested vs. vehicle by ANOVA. Results from ELISA assays of optical densities at 450 nanometers ($OD_{450}$) for individual animal sera pre- and post-dosing for 12 weeks are shown in FIG. 4. Sera were assayed at a 1:600 dilution in PBS. (Mouse Anti-dsDNA Total Ig Qualitative ELISA kits, Alpha Diagnostic International). Dosing was conducted by either oral (p.o.) or intraperitoneal (i.p.) administration. Individual data points from this assay are illustrated in FIG. 4. FIG. 4 shows that at 12 weeks, there was also a statistically significant difference in mean dsDNA level between vehicle and the high dose of Compound 23.

No effect on proteinuria (measured by BCA protein assay) or skin lesions was seen by any compound in this experiment.

TABLE 4

Dosing Regimen

| Group | Compound | Dose (mg/kg) | Route of admin. | Regimen |
|---|---|---|---|---|
| 1 | Compound 23 | 60 | p.o. | M-F |
| 2 | Compound 23 | 20 | p.o. | M-F |
| 3 | Hydroxychloroquine | 60 | p.o. | M-F |
| 4 | Vehicle | — | p.o. | M-F |
| 5 | Cyclophosphamide | 50 | i.p. | Every 10 days |

Example 13

In Vivo Biological Activity

NZBWF1/J Spontaneous Lupus Model

An in vivo study of Compound 23 and Compound 30 was conducted in an NZBWF1/J mouse model. Mice were obtained from Jackson Laboratories, divided into groups of 12, and dosed orally with compounds in water five days a week beginning at 5 months of age. Dosing details are provided in Table 5 below:

TABLE 5

Dosing Regimen

| Group | Compound | Dose (mg/kg) | Route of admin. | regimen | Dose/head (ml) |
|---|---|---|---|---|---|
| 1 | Compound 23 | 60 | p.o. | M-F | 0.2 |
| 2 | Compound 23 | 20 | p.o. | M-F | 0.2 |
| 3 | Compound 30 | 60 | p.o. | M-F | 0.2 |
| 4 | Compound 30 | 20 | p.o. | M-F | 0.2 |
| 5 | Vehicle ($dH_2O$) | — | p.o. | M-F | 0.2 |

Figure 5:
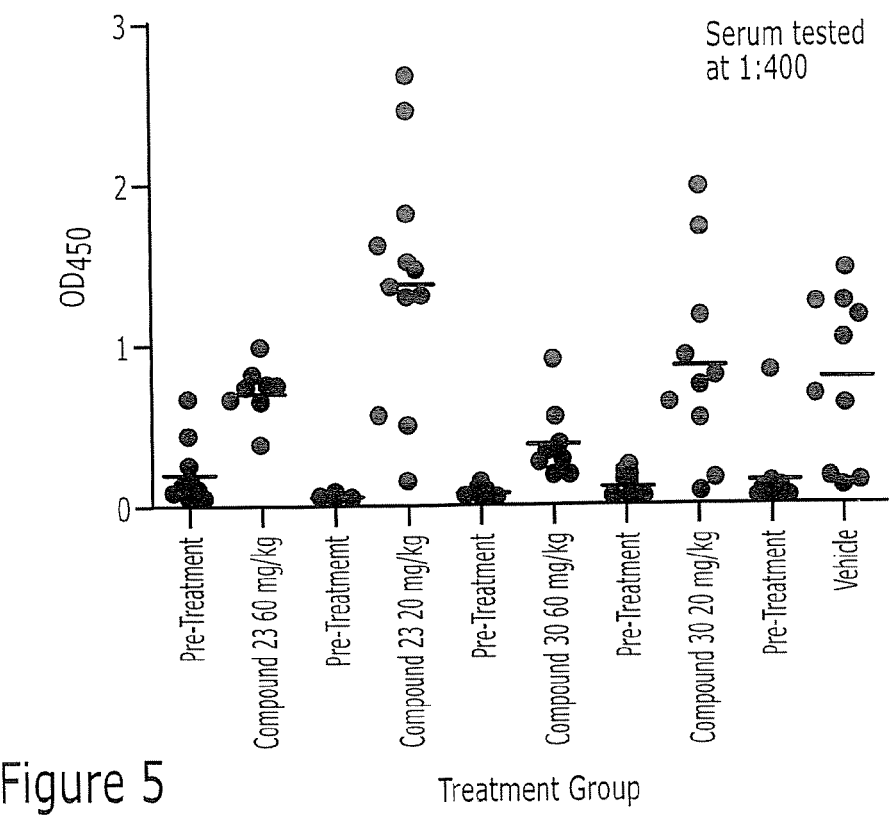
FIG. 5 is a plot showing results of an ELISA assay at OD$_{450}$ of mouse anti-dsDNA pre- and post-dosing of NZB/WF1/J mice for 16 weeks with 20 mg/kg or 60 mg/kg Compound 23 or Compound 30, as described in Example 13.
Figure 6A:
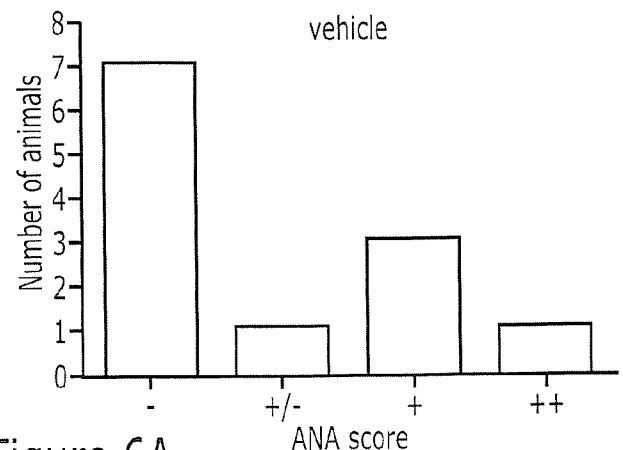
FIG. 6 is a set of bar graphs showing the number of NZB/WF1/J mice with each of the five possible ANA scores, after 16 weeks of dosing with 20 mg/kg or 60 mg/kg of Compound 23 or Compound 30, as described in Example 13
Figure 6B:
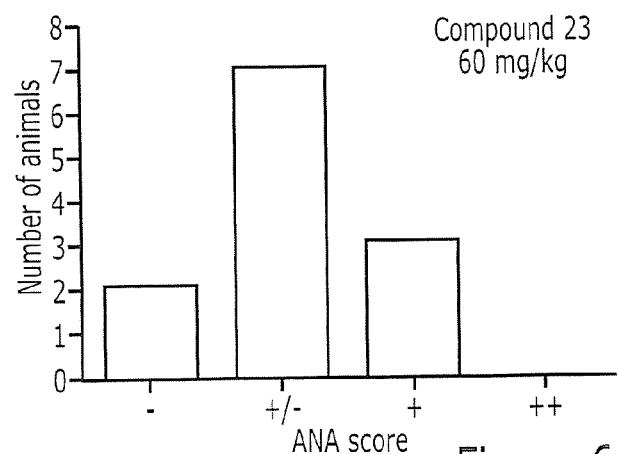
Figure 6C:
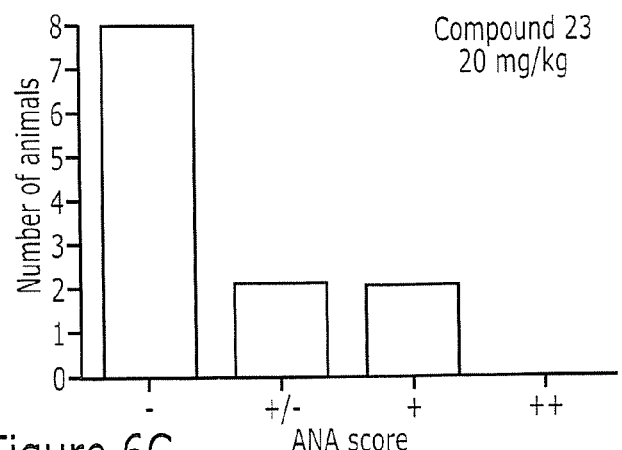
Figure 6D:
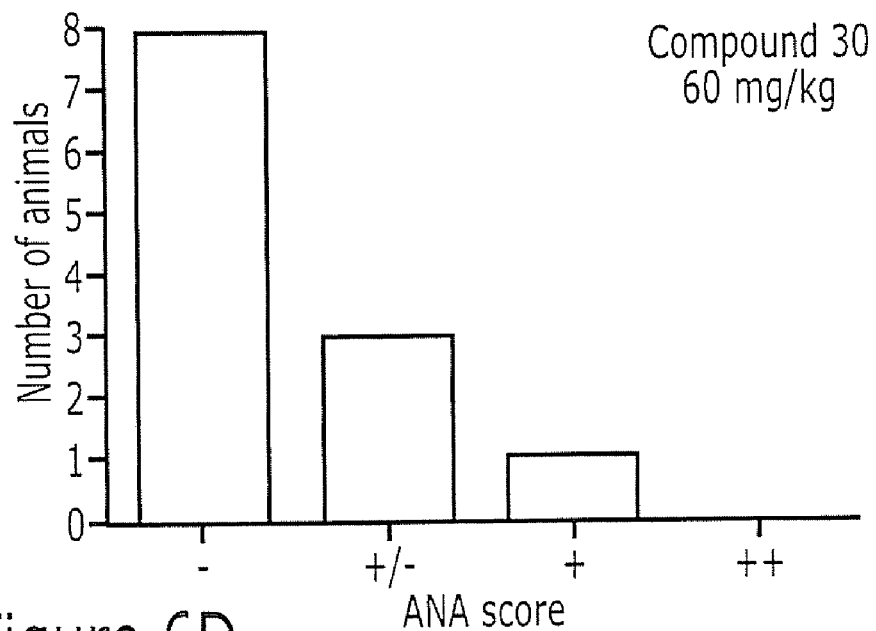
Figure 6E:
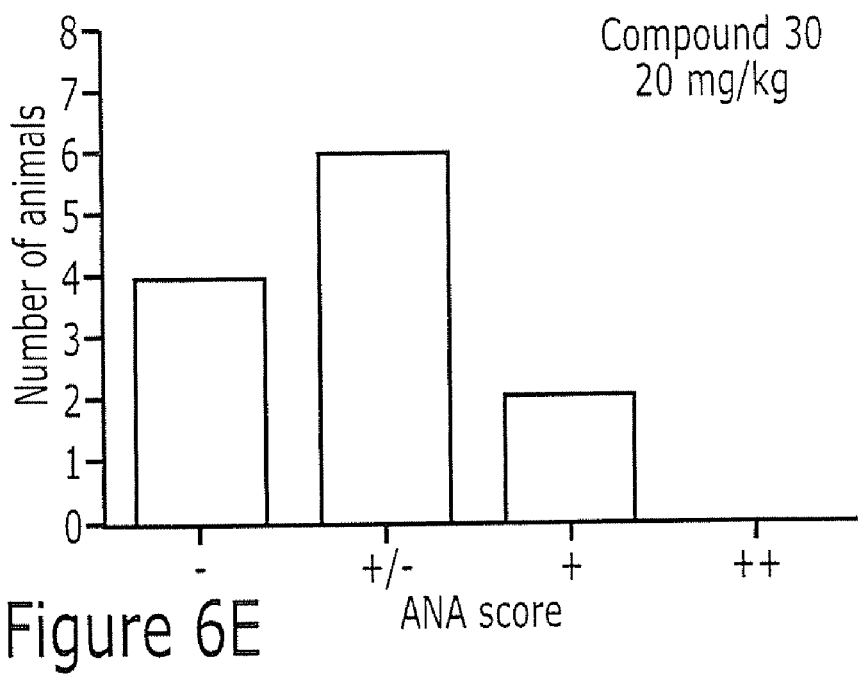

Neither of the compounds tested in this study, Compound 23 or Compound 30, showed an effect on anti-dsDNA during the 16 weeks of treatment after dosing with 20 mg/kg or 60 mg/kg of compound. Results of the study are illustrated in FIG. 5. Compound 30, which showed a somewhat higher potency than Compound 23 in the short-term assay, gave some suppression of anti-dsDNA at the high dose of 60 mg/kg, but, this was not statistically significant. ANA was measured in the same experiment, and although only 5 of 12 vehicle-treated animals progressed to scores of +/− or higher there was no effect of compound on distribution of ANA scores after 12 weeks of treatment. Results of the ANA scoring are illustrated in FIG. 6.

Compound 23 and Compound 30 consistently produced a dose-related weight loss in the NZBWF1/J mouse strain after 3 to 4 months of dosing. Histological examination of muscle, brain, kidney and spleen showed no obvious pathology in hematoxylin and eosin staining.

Daily oral dosing with 60 and 20 mg/kg Compound 23 resulted in suppression of anti-dsDNA in the MLR/lpr model of SLE. Compound 23 also showed a dose-dependent inhibition of anti-nuclear antibody development. Cyclophosphamide suppressed anti-dsDNA in the MRL/lpr model, while hydroxychloroquine had no detectable effect. Further, the test of Compound 23 in the NZB/W system showed no effect on anti-dsDNA, ANA, or proteinuria. Dose-dependent weight loss was observed after several months of dosing in NZB/W mice.

Example 14

In Vivo Biological Activity

Experimental Autoimmune Encephalitis Multiple Sclerosis Model

Experimental autoimmune encephalitis (EAE) is an induced autoimmunity in mice that mimics human multiple sclerosis, including autoantibody and cellular responses targeted against central nervous system antigens. To induce EAE, groups of 8 male C57BL/6J mice (Jackson Laboratories) were immunized subcutaneously on day 0 with the synthetic peptide MOGp35-55 (Becher et al. *J. Clin. Invest.* 112:1186-1191 (2003)), with amino acid sequence MEVG-WYRSPFSRVVHLYRNGK (SEQ ID NO:4) at a dose of 200 µg/mouse in complete Freund's adjuvant (CFA). At the same time the animals received pertussis toxin, i.p. at 30 ng/mouse. On day 2 the pertussis injection was repeated. On day 7 the mice were boosted with MOGp35-55, 200 µg/mouse in incomplete Freund's. Beginning on day 9 the mice were dosed daily by oral gavage with Compound 23 in water at 20 mg/kg or 60 mg/kg. Symptoms were scored by observing degree and location of paralysis of the tail and limbs, the average score for each group of 8 mice is shown.

Figure 7:
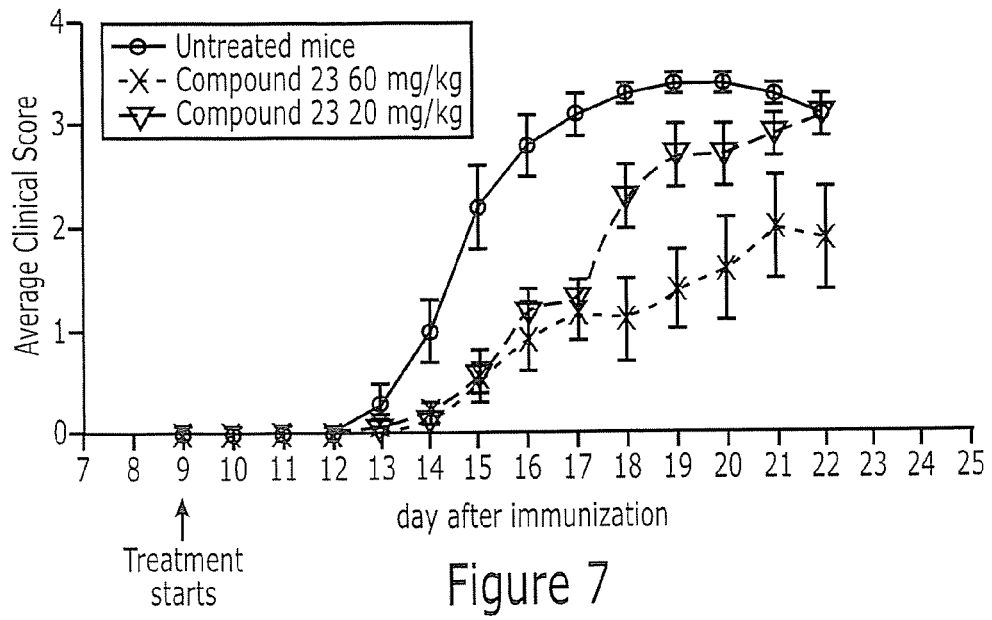
FIG. 7 is a graph showing results of administration of 20 mg/kg or 60 mg/kg of Compound 23 to C57BL/6J mice immunized with synthetic peptide MOGp35-55 to induce experimental autoimmune encephalitis (EAE), which mimics multiple sclerosis, as described in Example 14.

The results of this study are shown in FIG. 7. It can be observed that MOG-induced EAE was suppressed significantly in mice administered 20 mg/kg Compound 23, compared to the control mice, and was suppressed further in mice administered 60 mg/kg of the same compound.

Example 15

In Vivo Biological Activity

Collagen Induced Arthritis

The type II collagen induced arthritis model was used for the purpose of in vivo evaluation of Compound 2 for the treatment of arthritis. In this model, arthritis was induced in male DBA/1J (Jackson Labs) mice using complete Freund's adjuvant. A first priming/immunization dose of 300 µg of bovine type II collagen emulsified in an equal volume of complete Freund's adjuvant is injected subcutaneously (s.c.) at least 5 mm from the base of the tail.

Starting on day 9 after immunization and each day for 5 days per week thereafter, each mouse was dosed orally with 6 mg/kg, 20 mg/kg, or 60 mg/kg of Compound 2 or placebo 5 days per week.

A second immunization dose was administered 21 days after the first immunization by s.c. injection above the first immunization site of 200 µg of bovine type II collagen emulsified in an equal volume of incomplete Freund's adjuvant. To further promote arthritis progression, animals receive an intraperitoneal injection of lipopolysaccharide (LPS) (1 µg/mouse in PBS) three days after the second immunization.

Figure 8:
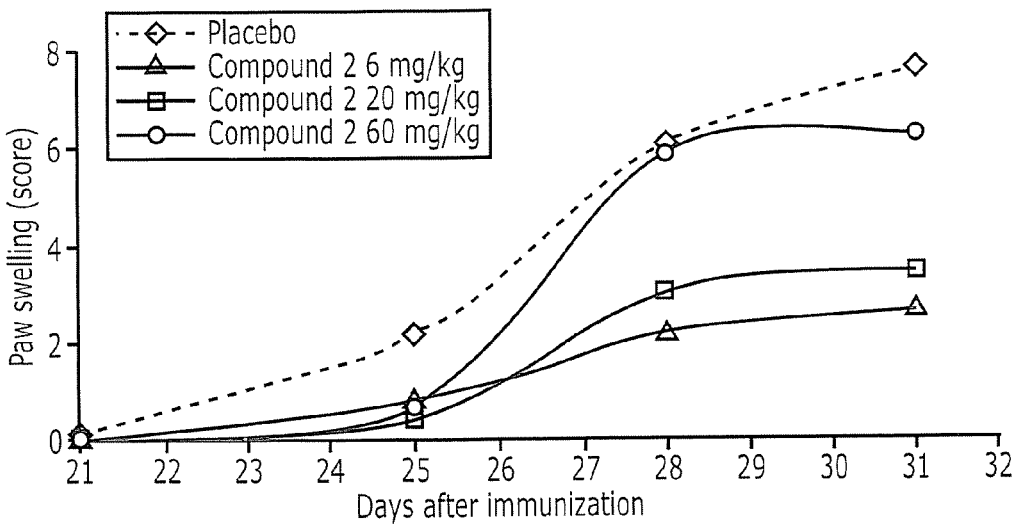
FIG. 8 is a graph showing results of administration of 6 mg/kg, 20 mg/kg or 60 mg/kg Compound 2 to male DBA/1J mice immunized with bovine type II collagen emulsified in complete Freund's adjuvant to induce arthritis, as described in Example 15.

At 21, 25, 28, and 31 days after the first immunization dose, the animals were examined for evidence of paw swelling and assigned an arthritis score at each time point. The results of this assay are shown in FIG. 8. Suppression of paw swelling was observed after dosing with 6 and 20 mg/kg, but, the results after dosing with 60 mg/kg were not clear. The anomalous 60 mg/kg result suggest the need for further studies to determine an appropriate upper dosing level for this particular animal model.

Example 16

In Vivo Biological Activity

Cecal Ligation and Puncture Surgery

The cecal ligation and puncture (CLP) model involves a surgical procedure where an abdominal incision is made to expose the cecum (an easily isolated section of the digestive tract) and a portion of the cecum is ligated. The cecum is then punctured and a small amount of the intestinal contents is extruded. The incision is closed and the animals are given resuscitative saline and antibiotics. Sepsis develops primarily due to bacteria from the extruded intestinal contents and disease development occurs with a rapidity and severity that depends on the size and number of punctures in the cecum.

A. Cecal Ligation and Puncture Surgery.

Anesthesia is induced in mice by i.p. administration of a combination of ketamine, xylazine and acepromazine. The animal's abdominal region can be closely shaved and a transponder for measuring body temperature is implanted subcutaneously. The procedure takes place in an area suitable for aseptic survival surgery. Animals are placed on a warming, pad throughout the procedure. The abdominal area is prepped with a minimum of three alternating wipes of povidone/iodine and alcohol.

A midline incision is made to open the abdomen and expose the cecum. The cecum is removed from the abdominal cavity using cotton-tipped applicators moistened with saline. The tip of the cecum is ligated using 4-0 sutures just distal to the ileocecal valve. Cecal contents are shifted to one end and the cecum is then punctured with a sterile needle. Pressure is applied to extrude a small amount of material from the cecum into the peritoneal cavity. The ligature is left in place and not removed. The muscle and fascia is closed with continuous 4-0 sutures and the skin is closed with wound staples.

Immediately after surgery, 5 ml per 100 g body weight of warm resuscitative saline is injected s.c. Baseline readings for temperature and body weight are recorded. One hour after surgery, a 20 mg/kg dose of the antibiotic moxifloxacin is administered i.p. along with any anti-sepsis drug candidates being tested. Antibiotics are administered at 24 hr intervals for the duration of the study. The dose of antibiotic administered is not intended to eradicate the bacteria released by CLP, but is instead used to model the clinical scenario where humans would be receiving antibiotics although they may be ineffective. Although moxifloxacin is associated with prolongation of the QT interval, it is considered safe for clinical use as long as unfavorable drug, interactions are avoided (Torres et al., *J Surg Res.* 125: 88-93 (2005)) and the antibiotic has previously proven safe and effective in another mouse sepsis model (Alkorta et al., *Int J. Antimicrob. Agents* 25 (2): 163-7, (2005)).

B. Administration of Test Compound.

Compounds are administered approximately 1 hr after surgery at the time of antibiotic injection, although the timing can vary. Compounds are administered twice per day depending on the pharmacokinetic properties of the candidate compounds. Administration of test compound is performed by any of the following routes according to established guidelines for administration: oral, intraperitoneal, subcutaneous, or intravenous injection through the tail vein.

Groups of around 10 animals are used. Drug evaluation experiments have a group that experiences cecal ligation and puncture and receives only vehicle (control group), and a group(s) that experiences CLP and receives a test treatment compound. Compounds are administered 1 hr post-surgery and animals are monitored for survival every two hours during the day. Body temperatures are taken via transponder every two hours and animal health is monitored at each point. Body weights are taken at 4 hr intervals. Animals are monitored for a period of at least 8 hrs each day. Serum samples are taken for measurement of cytokine levels. Mortality is monitored, and used as a measure of the efficacy of drug treatment.

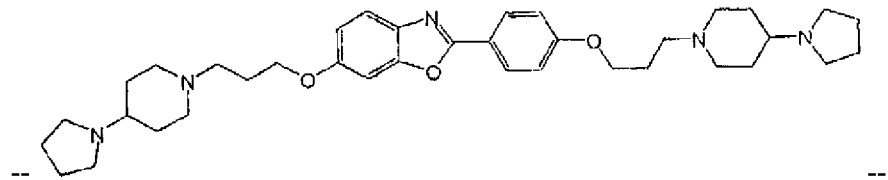

We claim:

1. A compound of formula (I):

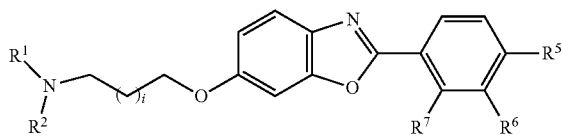

(I)

or a pharmaceutically acceptable salt thereof,
wherein one of $R^5$, $R^6$, or $R^7$ is a group of formula (a):

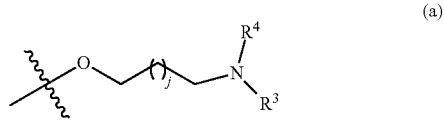

(a)

and when $R^5$ is (a), $R^6$ and $R^7$ are both H; when $R^6$ is (a), $R^5$ and $R^7$ are both H; and when $R^7$ is (a), $R^5$ and $R^6$ are both H;

i and j are the same and are 0, 1, 2, 3, or 4;

$R^1$ and $R^4$ are the same and selected from the group consisting of H, $CH_3$, and $CH_2CH_3$;

$R^2$ is $CH_3$ and $R^3$ is selected from the group consisting of $(CH_2)_hN(CH_3)_2$ and $(CH_2)_2O(CH_2)_2O(CH_2)_2N(CH_3)_2$, wherein h is 2, 3, or 4; or $R^2$ and $R^3$ are the same and selected from the group consisting of:

$(CH_2)_kCH_3$, wherein k is 0, 1 or 2,
$(CH_2)_mN(CH_2CH_3)_2$, wherein m is 2 or 3,
$(CH_2)_nN(CH_3)_2$, wherein n is 2, 3 or 4,
$(CH_2)_pO(CH_2)_qN(CH_3)_2$, wherein p and q are the same and are 2 or 3;
a group of formula (b):

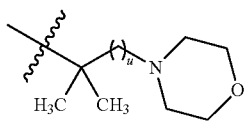
(b)

wherein u is 0 or 1; or
a group of formula (c):

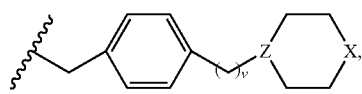
(c)

wherein v is 0 or 1, Z is N or CH, and X is O or $NCH_3$; or
$R^1$—N—$R^2$ and $R^3$—N—$R^4$ are the same and selected from the group consisting of:
a group of formula (d):

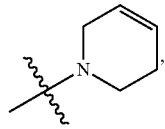
(d)

and
a group of formula (e):

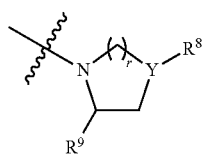
(e)

wherein
r is 1, 2, or 3,
Y is CH or N,
$R^8$ is H, $CH_3$, $CH(CH_3)_2$, $N(CH_3)_2$, $CH_2OCH_3$, or a group of formula (f):

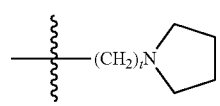
(f)

wherein t is 0 or 1, and
$R^9$ is H, $CH_2OCH_3$, or a group of formula (f).

2. The compound of claim 1, wherein i and j are both 1.
3. The compound of claim 1, wherein $R^2$ and $R^3$ are the same and selected from the group consisting of:
$(CH_2)_kCH_3$, wherein k is 0, 1 or 2;
$(CH_2)_mN(CH_2CH_3)_2$, wherein m is 2 or 3;
the group of formula (b); and
the group of formula (c).
4. The compound of claim 1, wherein $R^1$—N—$R^2$ and $R^3$—N—$R^4$ are the same and selected from the group consisting of:
a group of formula (g): a group of formula (h):

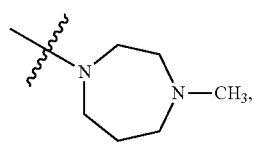
(g)

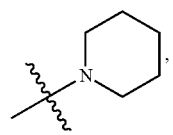
(h)

a group of formula (i): a group of formula (j):

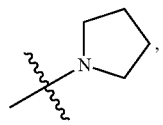
(i)

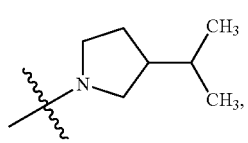
(j)

a group of formula (k): a group of formula (m):

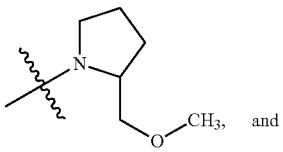
(k)

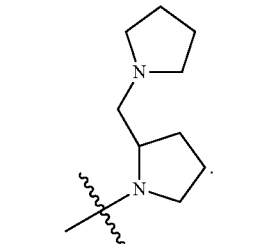
(m)

5. The compound of claim 1, wherein:
i and j are both 1;
$R^1$ and $R^4$ are the same and selected from the group consisting of H and $CH_3$;

$R^2$ is $CH_3$ and $R^3$ is selected from the group consisting of $(CH_2)_2N(CH_3)_2$ and $(CH_2)_2O(CH_2)_2O(CH_2)_2N(CH_3)_2$; or $R^2$ and $R^3$ are the same and selected from the group consisting of:
a) $(CH_2)_kCH_3$, wherein k is 0, 1 or 2;
b) $(CH_2)_mN(CH_2CH_3)_2$, wherein m is 2 or 3;
c) the group of formula (b); and
d) the group of formula (c);

or $R^1$—N—$R^2$ and $R^3$—N—$R^4$ are the same and selected from the group consisting of:
the group of formula (g), the group of formula (h), the group of formula (i), the group of formula (j), the group of formula (k), and the group of formula (m).

6. The compound of claim 1, wherein:
$R^5$ is the group of formula (a), and $R^6$ and $R^7$ are each H.

7. The compound of claim 1, wherein the compound is selected from the group consisting of:

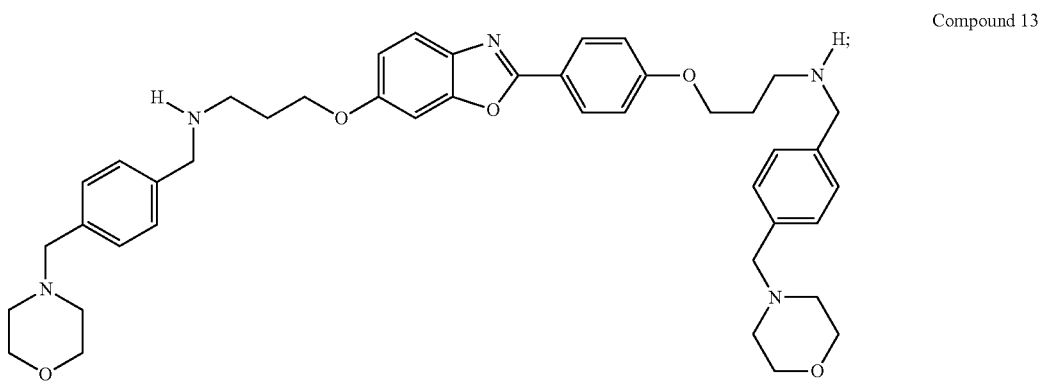

Compound 13

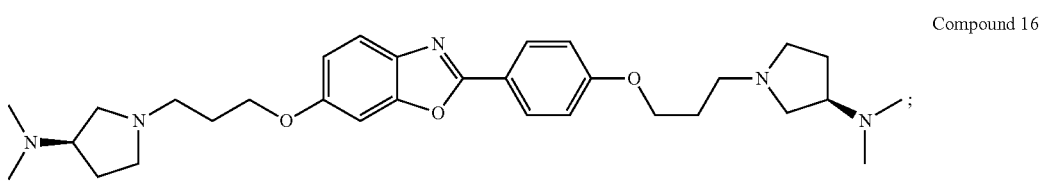

Compound 16

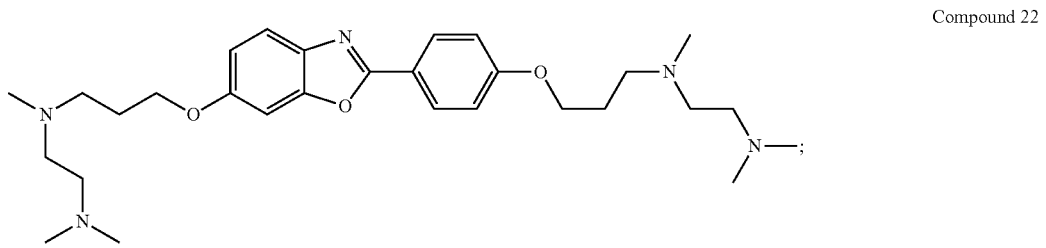

Compound 22

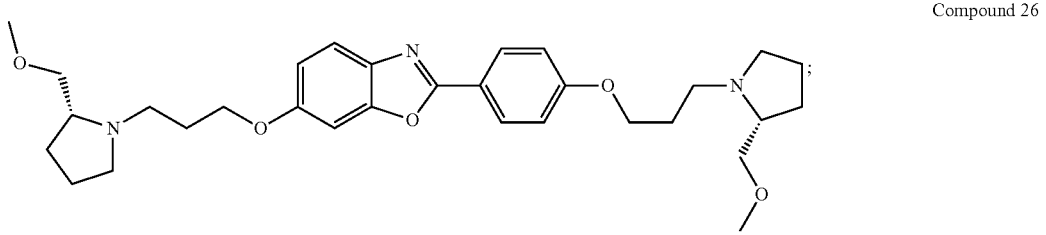

Compound 26

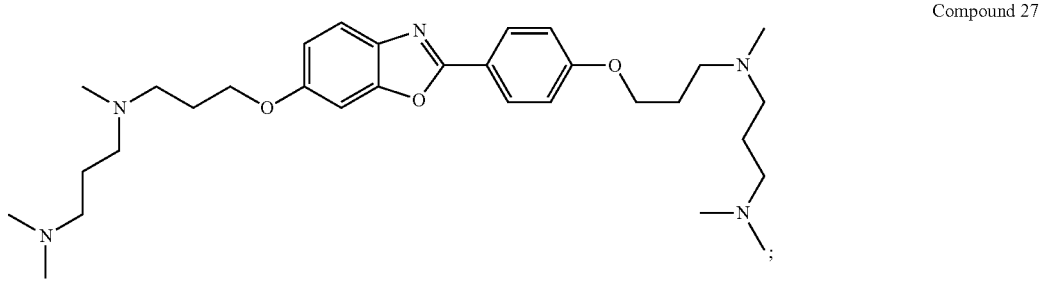

Compound 27

-continued
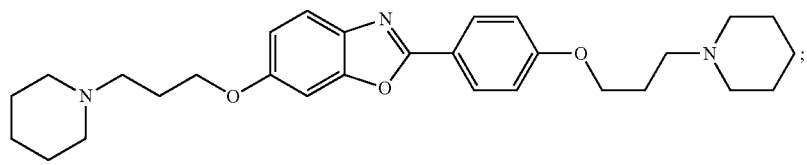
Compound 30
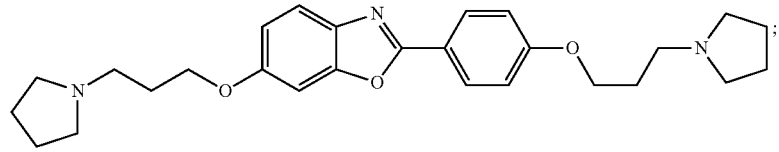
Compound 23
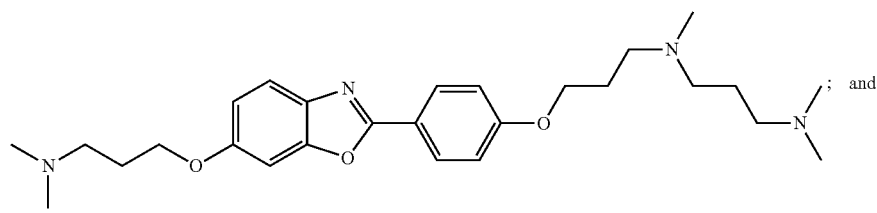
Compound 34
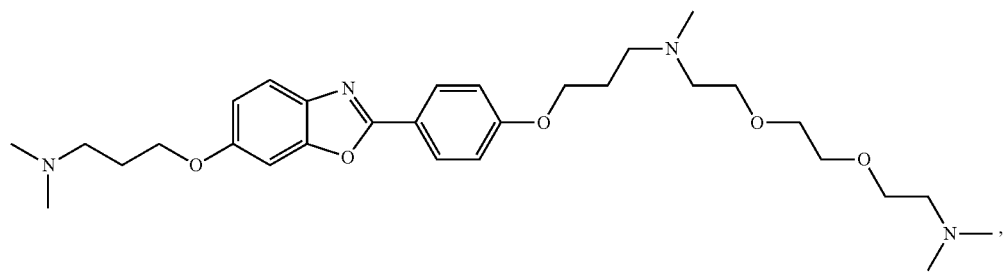
Compound 35
or a pharmaceutically acceptable salt thereof.
8. The compound of claim 7, wherein the compound is
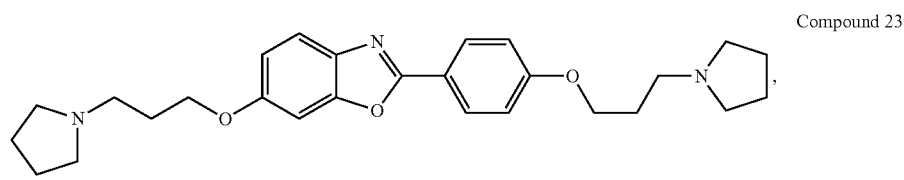 [SMILES: c1cc(-c2nc3ccc(OCCCN4CCCC4)cc3o2)ccc1OCCCN1CCCC1]
Compound 23
or a pharmaceutically acceptable salt thereof.
9. The compound of claim 8, wherein the compound is a bromide salt.
10. A compound selected from the group consisting of:
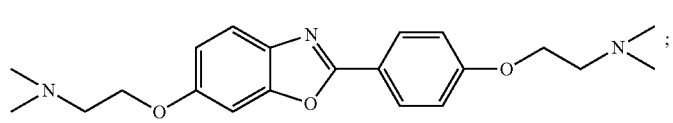
Compound 1
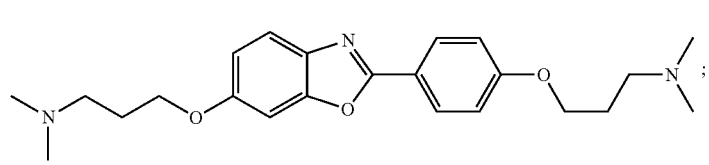
Compound 2

-continued
Compound 3
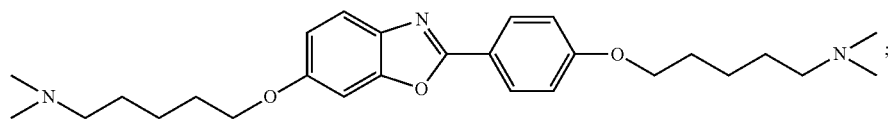
Compound 4
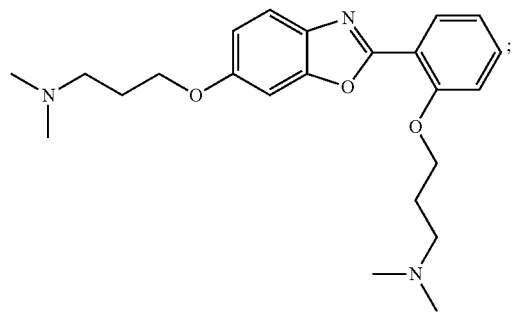
Compound 5
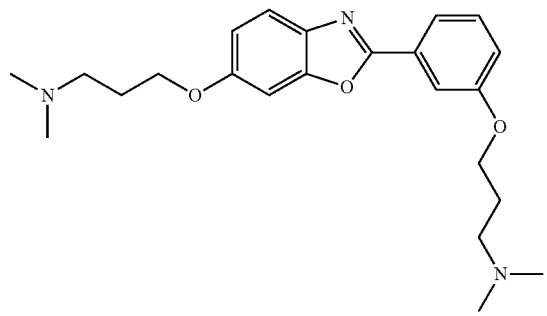
Compound 6
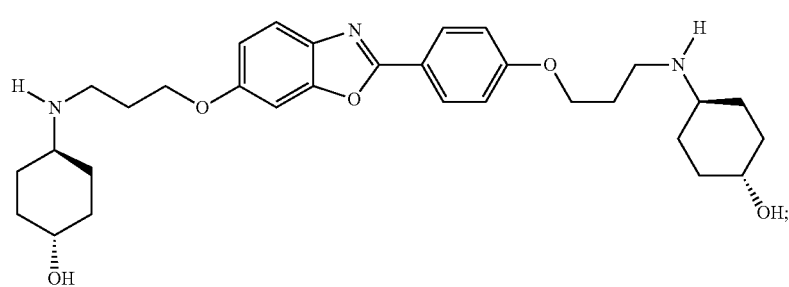
Compound 7
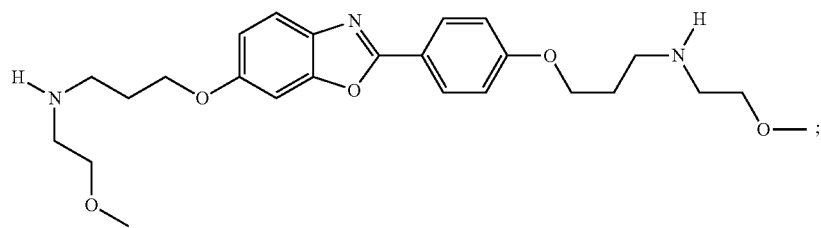
Compound 8
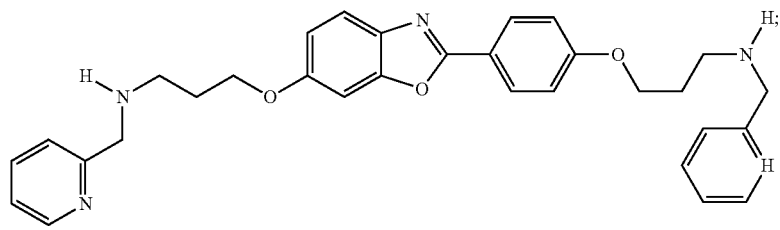
Compound 9
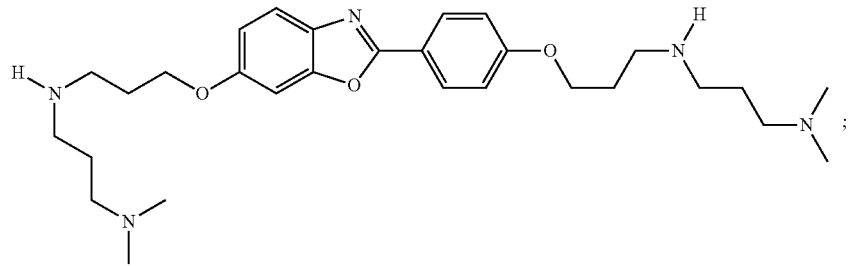

-continued
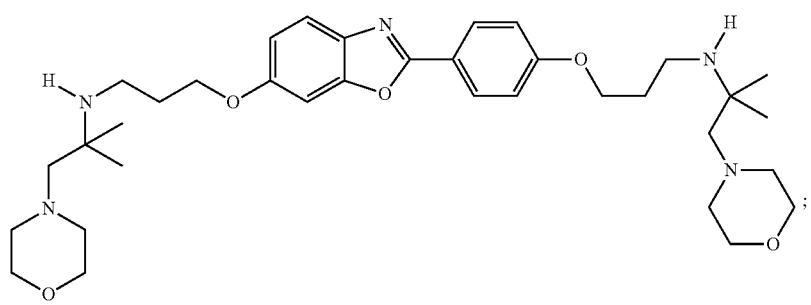
Compound 10
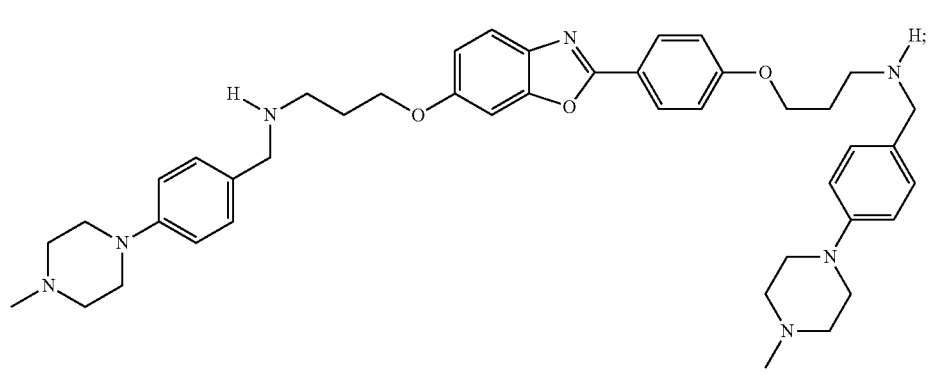
Compound 11
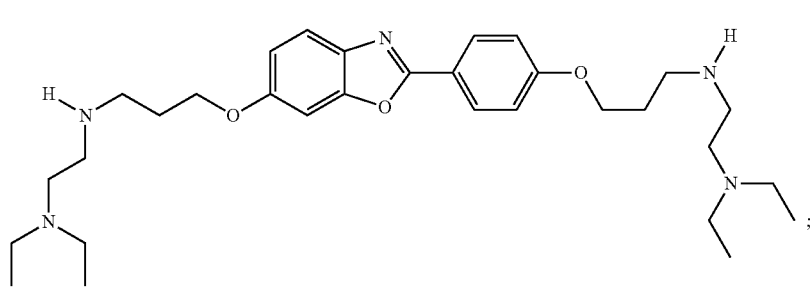
Compound 12
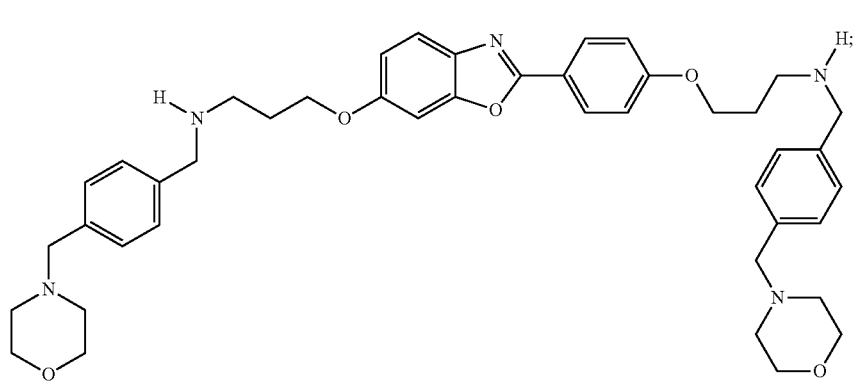
Compound 13
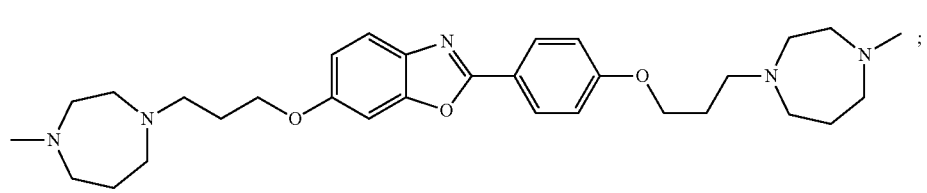
Compound 14

-continued
Compound 15
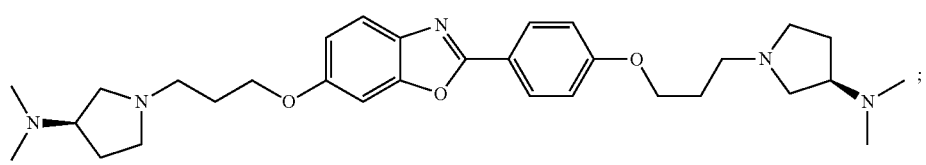
Compound 16
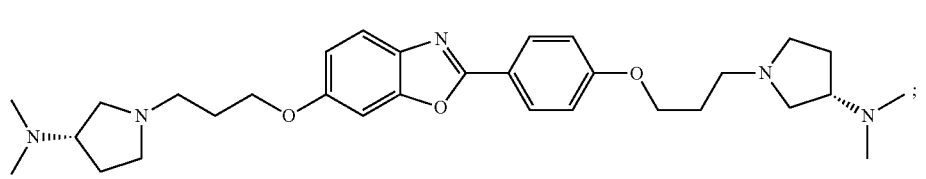
Compound 17
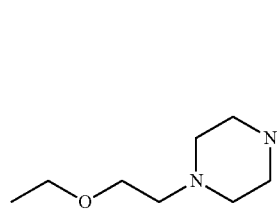
Compound 18
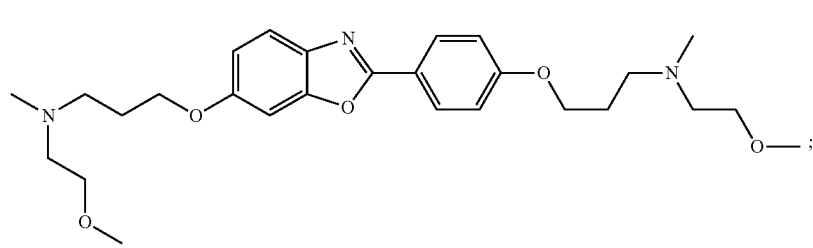
Compound 19
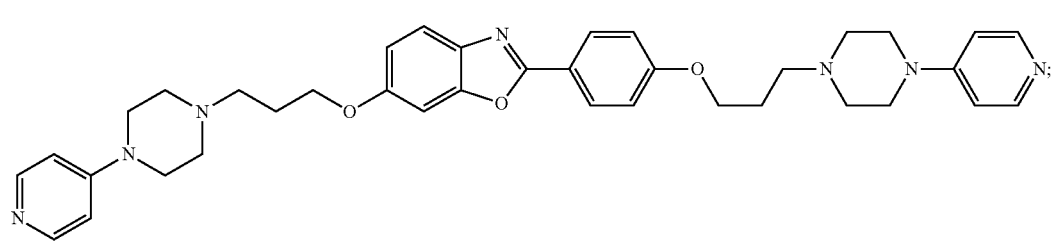
Compound 20
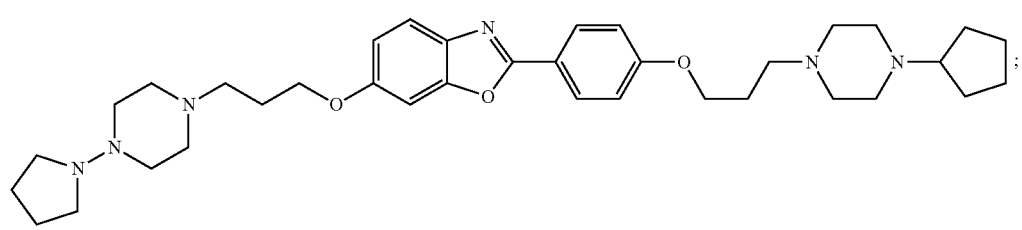
Compound 21
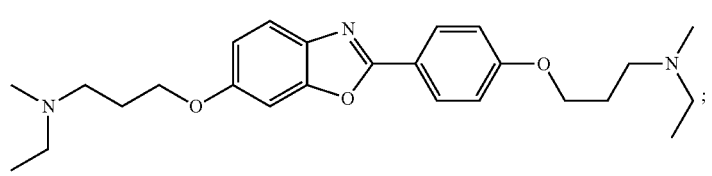

-continued
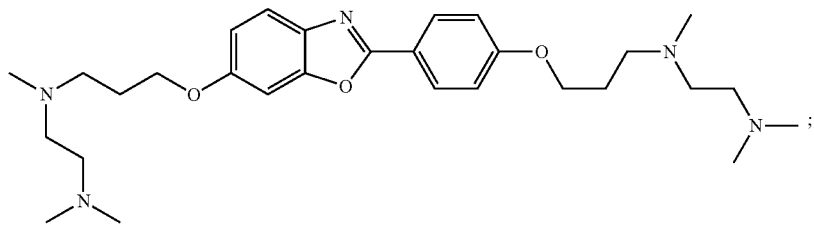
Compound 22
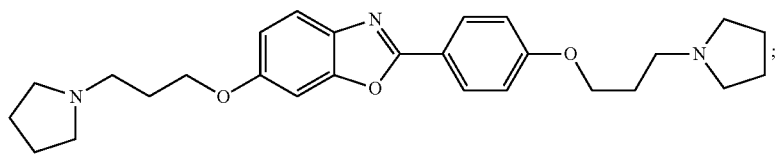
Compound 23
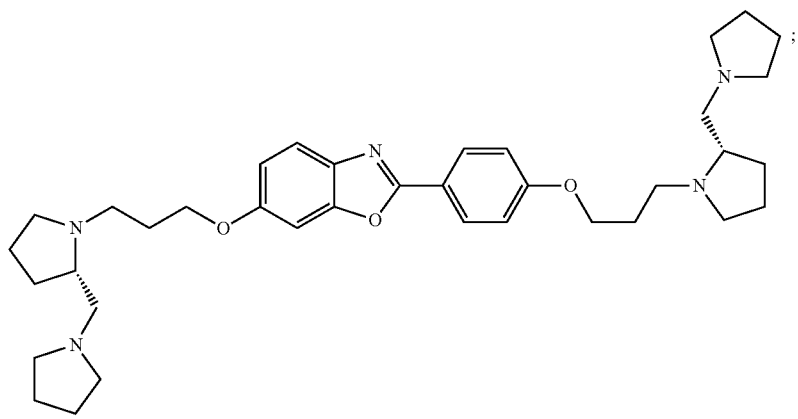
Compound 24
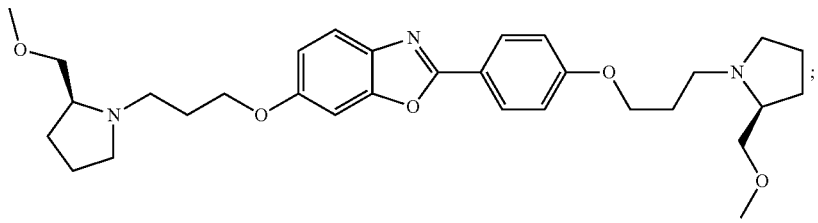
Compound 25
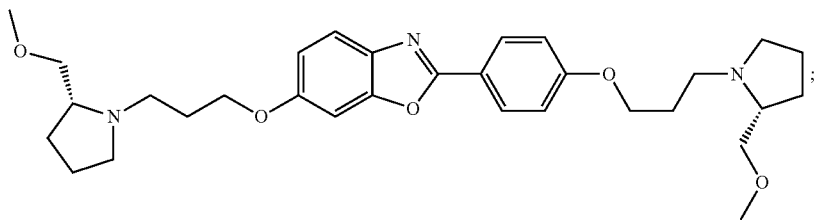
Compound 26
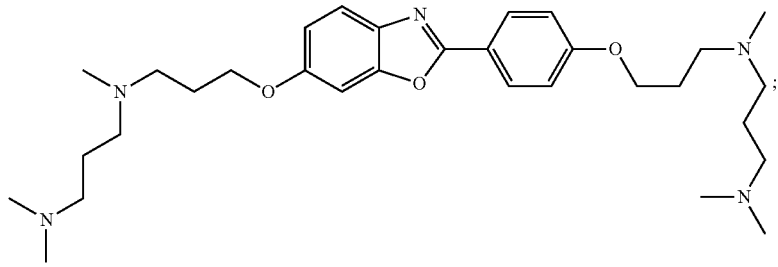
Compound 27

-continued
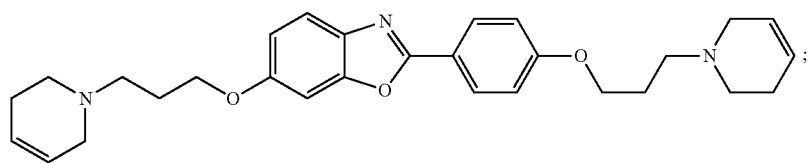
Compound 28
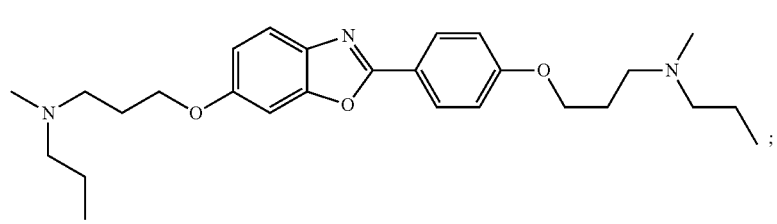
Compound 29
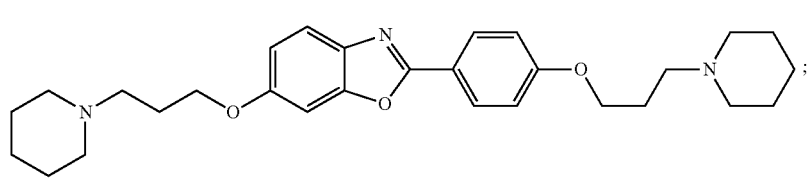
Compound 30
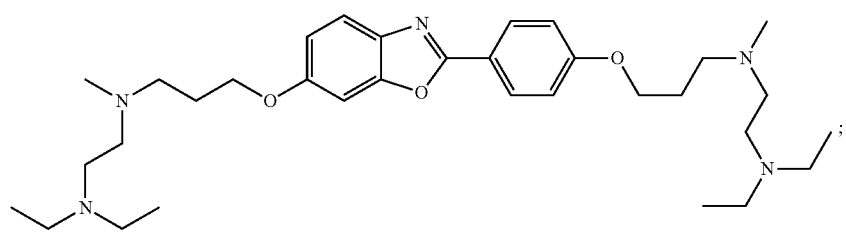
Compound 31
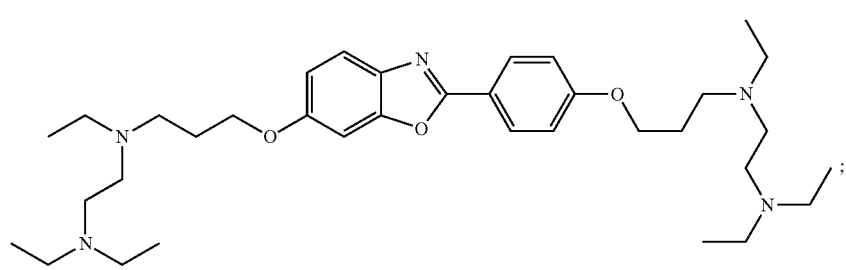
Compound 32
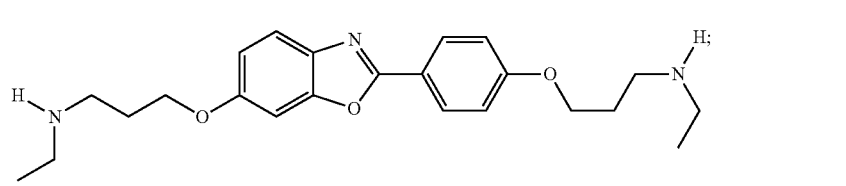
Compound 33
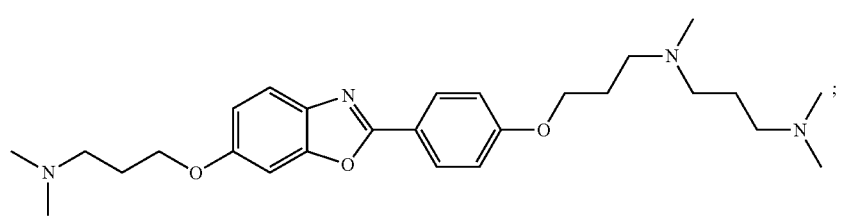
Compound 34

-continued

Compound 35
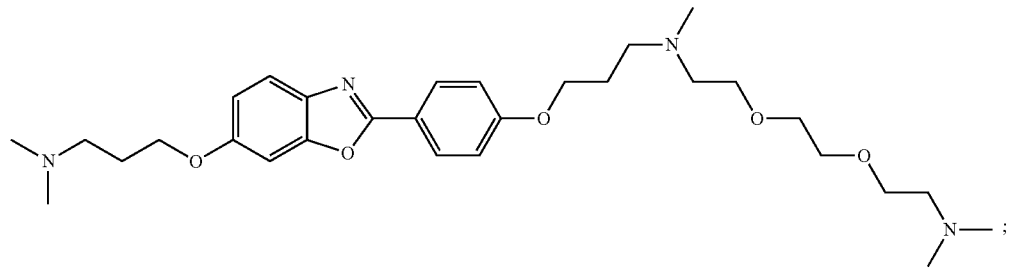

Compound 36
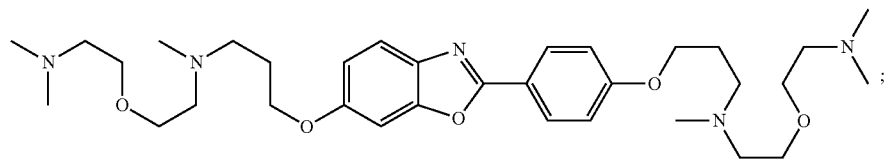

Compound 37
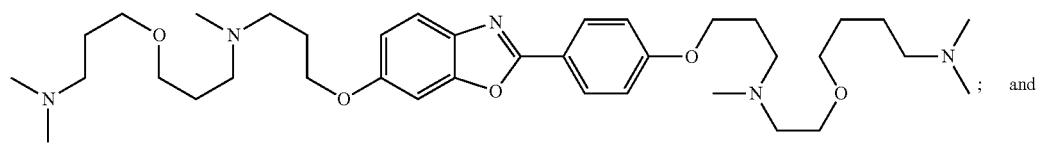

and

Compound 38
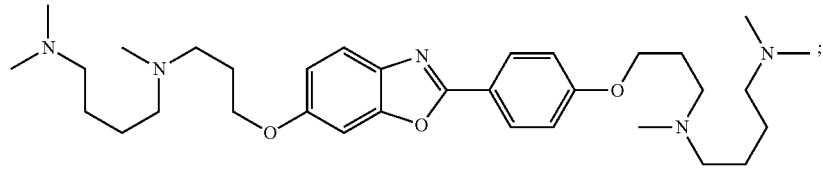

or a pharmaceutically acceptable salt thereof.

11. A pharmaceutical composition comprising a compound of formula (I):

(I)
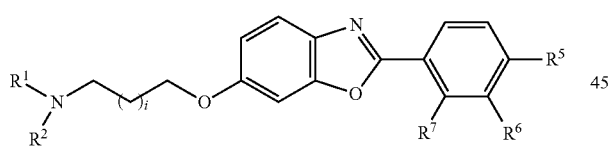

or a pharmaceutically acceptable salt thereof and a pharmaceutically acceptable carrier, wherein one of $R^5$, $R^6$, or $R^7$ is a group of formula (a):

(a)
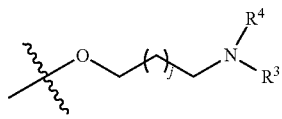

and when $R^5$ is (a), $R^6$ and $R^7$ are both H; when $R^6$ is (a), $R^5$ and $R^7$ are both H; and when $R^7$ is (a), $R^5$ and $R^6$ are both H;

i and j are the same and are 0, 1, 2, 3, or 4;

$R^1$ and $R^4$ are the same and selected from the group consisting of H, $CH_3$, and $CH_2CH_3$;

$R^2$ is $CH_3$ and $R^3$ is selected from the group consisting of $(CH_2)_hN(CH_3)_2$ and $(CH_2)_2O(CH_2)_2O(CH_2)_2N(CH_3)_2$, wherein h is 2, 3, or 4; or $R^2$ and $R^3$ are the same and selected from the group consisting of:
- $(CH_2)_kCH_3$, wherein k is 0, 1 or 2,
- $(CH_2)_mN(CH_2CH_3)_2$, wherein m is 2 or 3,
- $(CH_2)_nN(CH_3)_2$, wherein n is 2, 3 or 4,
- $(CH_2)_pO(CH_2)_qN(CH_3)_2$, wherein p and q are the same and are 2 or 3;

a group of formula (b):

(b)
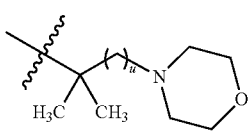

wherein u is 0 or 1; or
a group of formula (c):

(c)
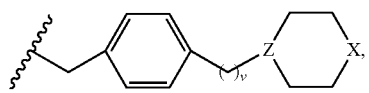

wherein v is 0 or 1, Z is N or CH, and X is O or $NCH_3$; or $R^1$—N—$R^2$ and $R^3$—N—$R^4$ are the same and selected from the group consisting of:

a group of formula (d):

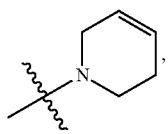

(d)

and
a group of formula (e):

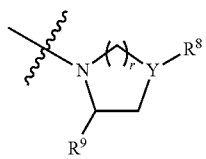

(e)

wherein
r is 1, 2, or 3,
Y is CH or N,
$R^8$ is H, $CH_3$, $CH(CH_3)_2$, $N(CH_3)_2$, $CH_2OCH_3$, or a group of formula (f):

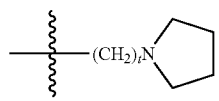

(f)

wherein t is 0 or 1, and
$R^9$ is H, $CH_2OCH_3$, or a group of formula (f).

12. The pharmaceutical composition of claim 11, wherein the compound is selected from the group consisting of:

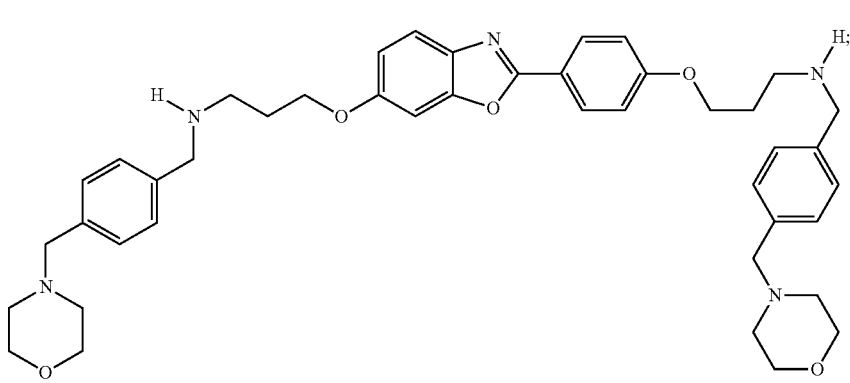

Compound 13

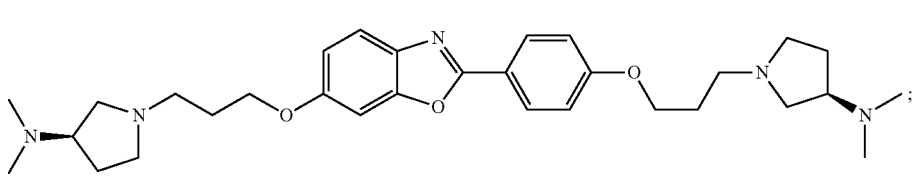

Compound 16

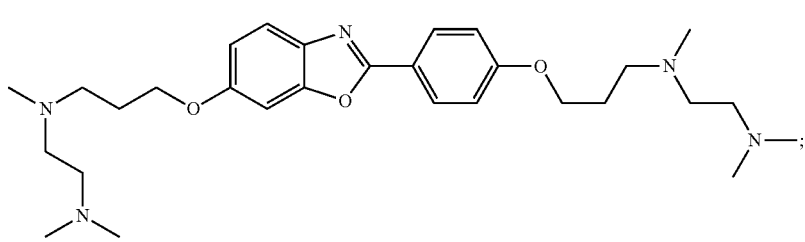

Compound 22

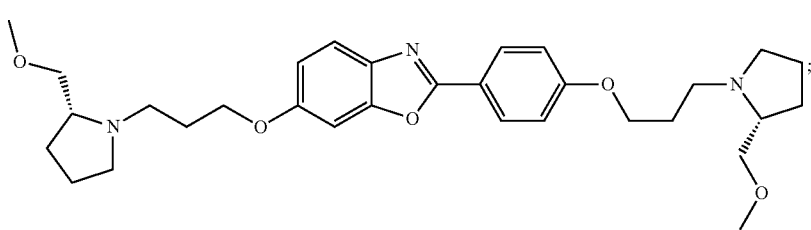

Compound 26

-continued
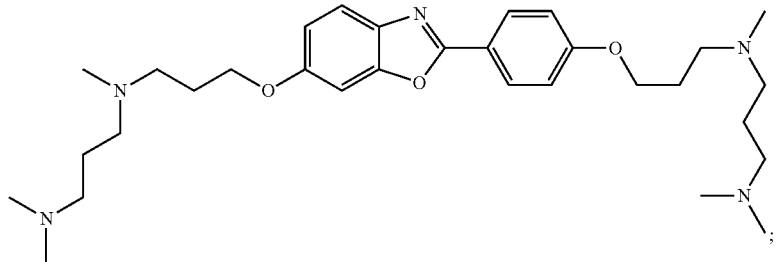
Compound 27
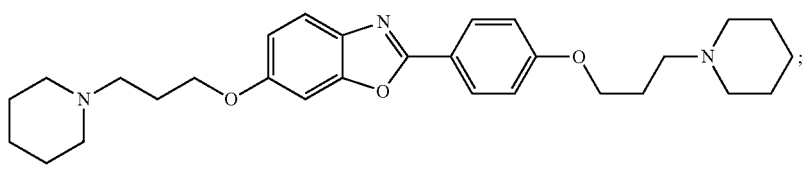
Compound 30
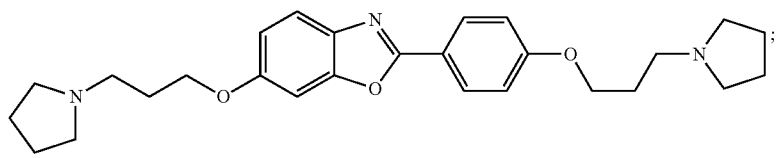
Compound 23
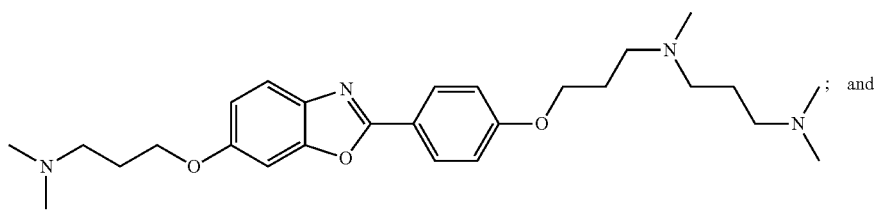
; and
Compound 34
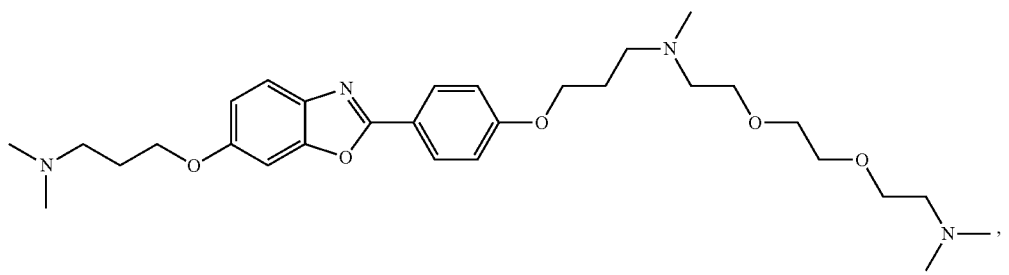
Compound 35
or a pharmaceutically acceptable salt thereof.

13. The pharmaceutical composition of claim 11, wherein the compound has the following formula:
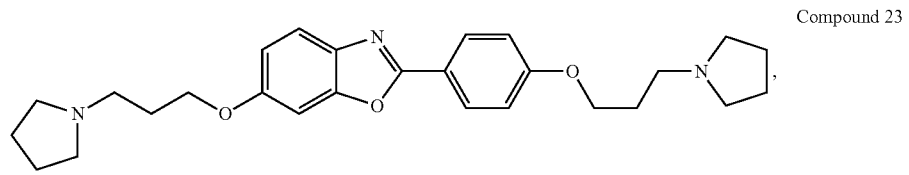 [SMILES: c1cc(-c2nc3ccc(OCCCN4CCCC4)cc3o2)ccc1OCCCN1CCCC1]
Compound 23
or a pharmaceutically acceptable salt thereof.
14. A pharmaceutical composition comprising a compound selected from the group consisting of:
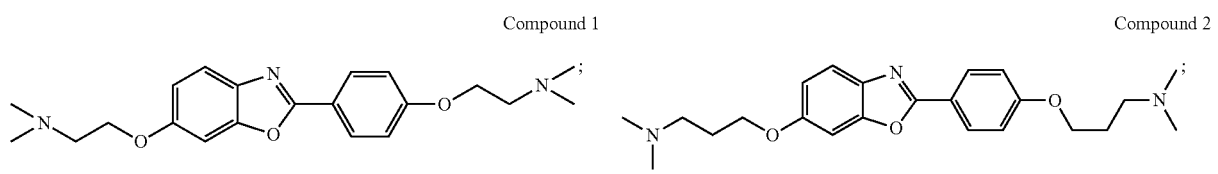
Compound 1
Compound 2
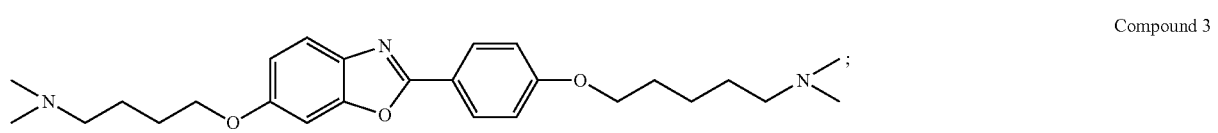
Compound 3
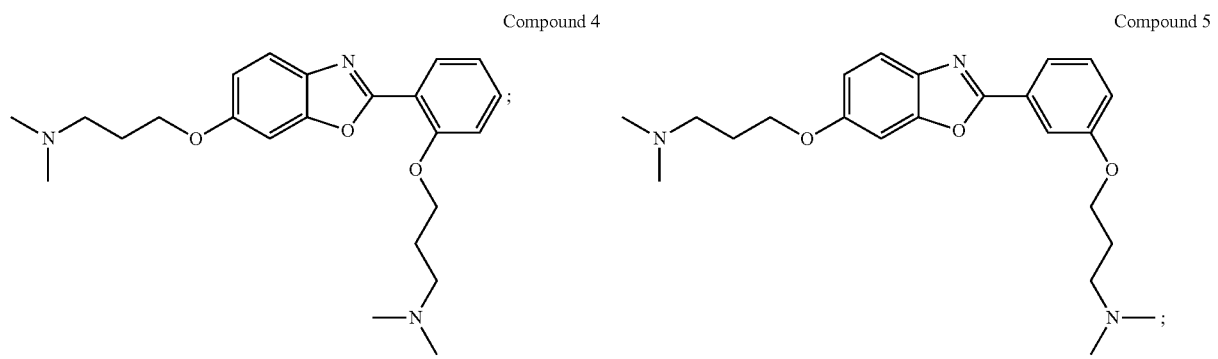
Compound 4
Compound 5
Compound 6
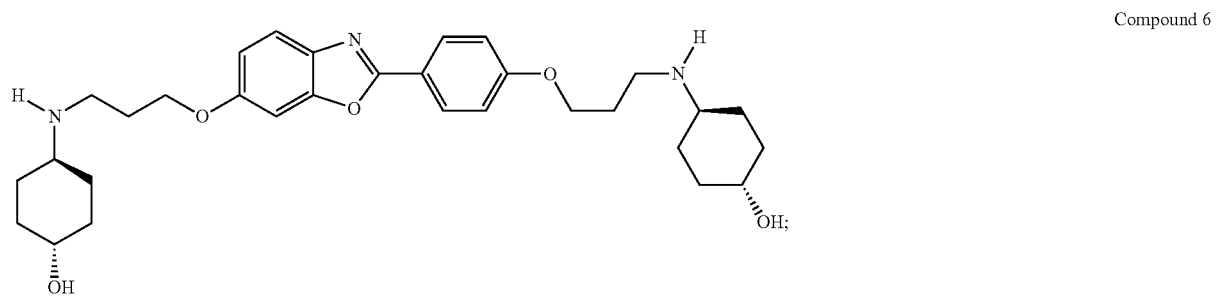
Compound 7
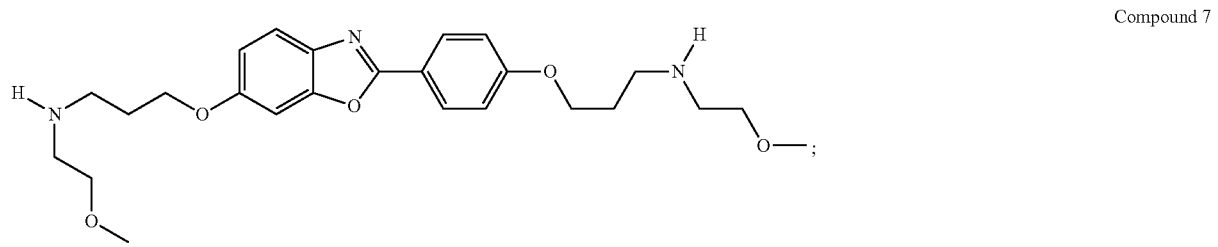

-continued
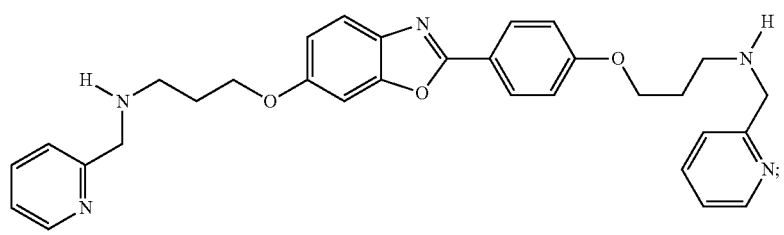
Compound 8
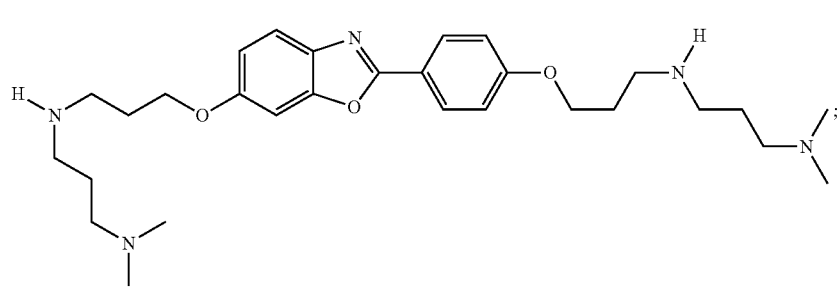
Compound 9
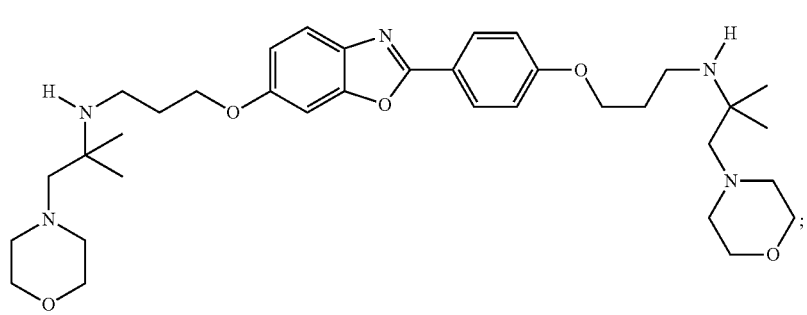
Compound 10
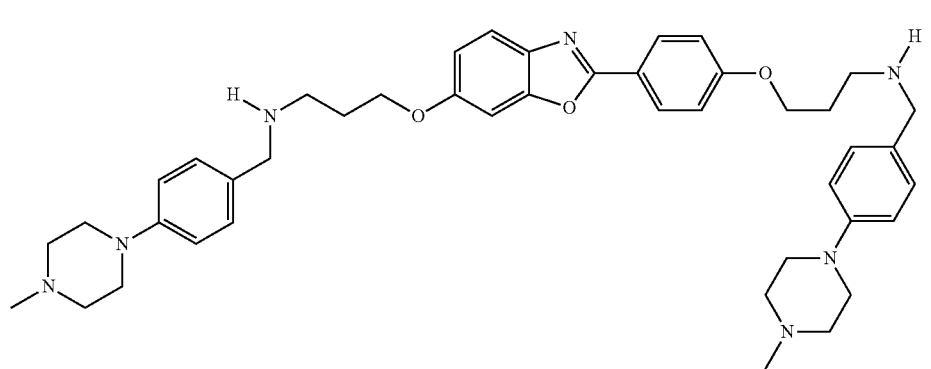
Compound 11
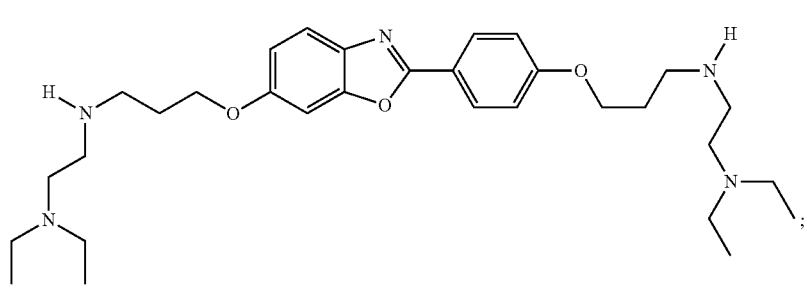
Compound 12

-continued
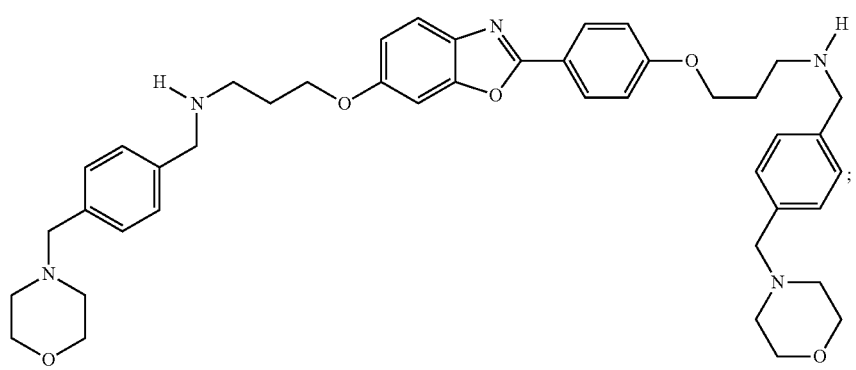
Compound 13
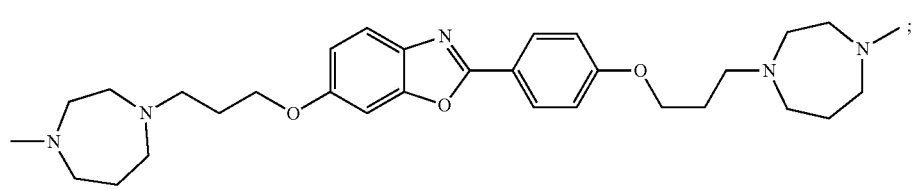
Compound 14
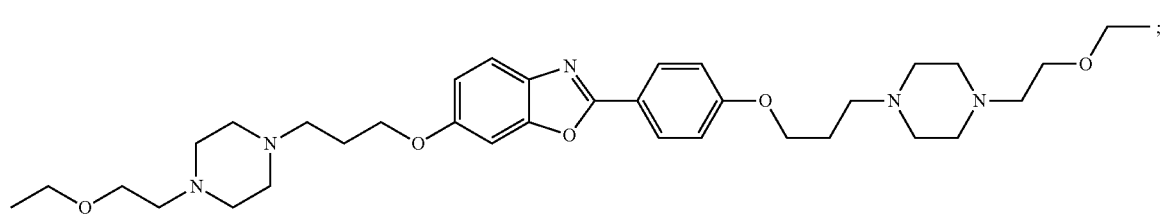
Compound 15
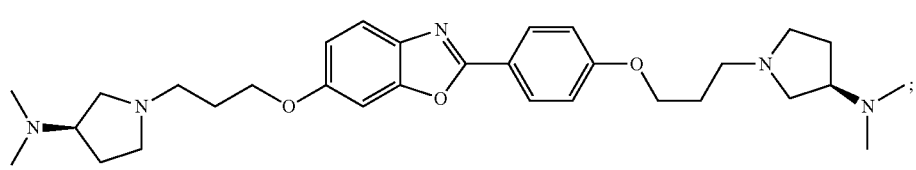
Compound 16
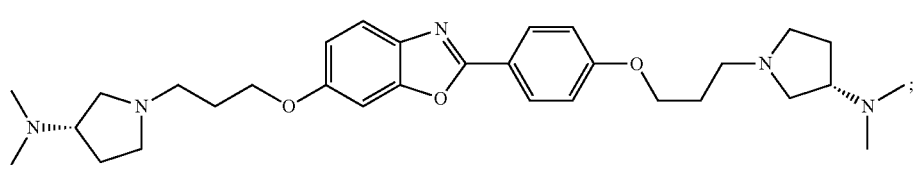
Compound 17
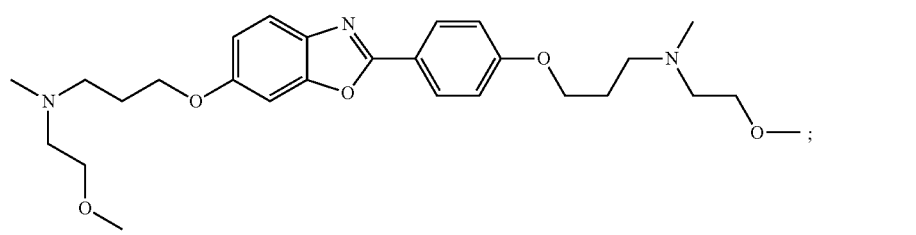
Compound 18
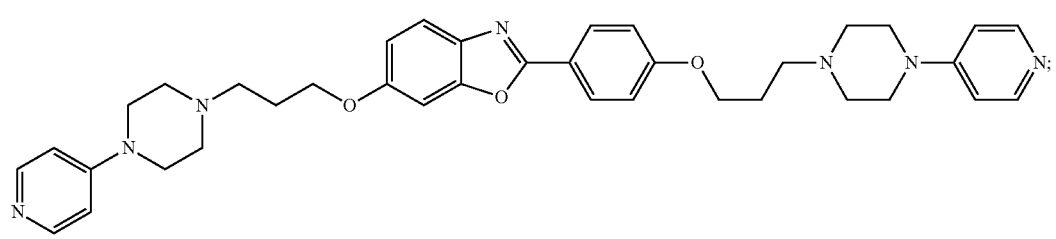
Compound 19

-continued
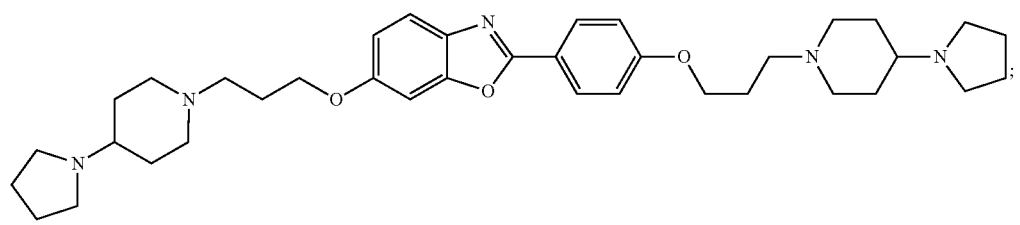
Compound 20
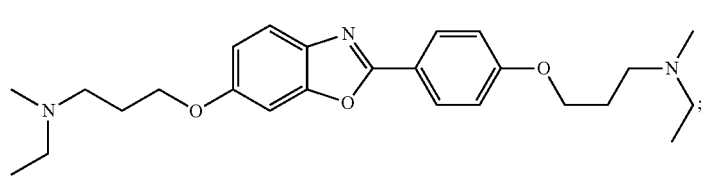
Compound 21
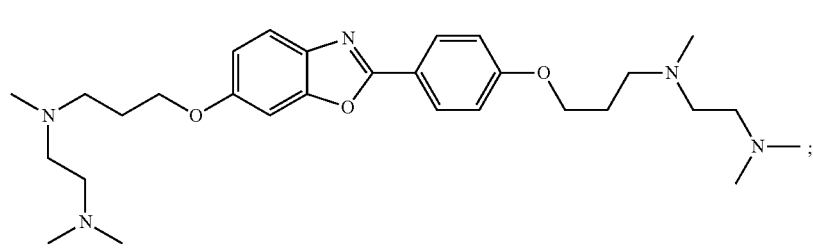
Compound 22
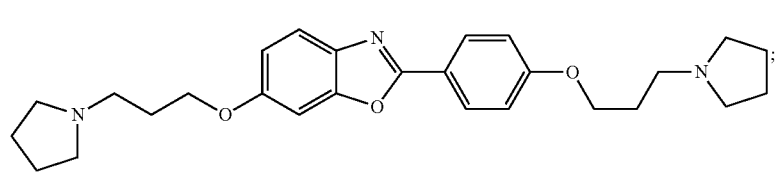
Compound 23
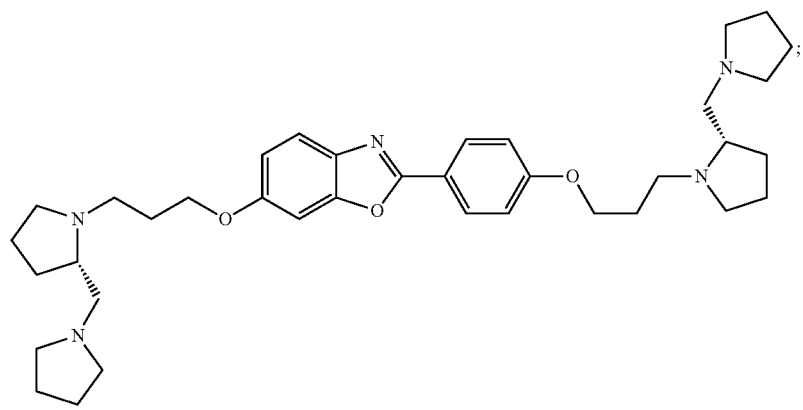
Compound 24
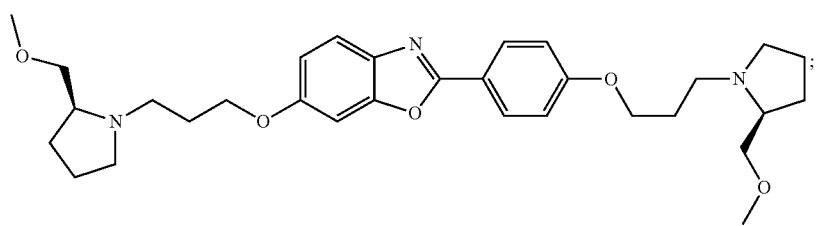
Compound 25

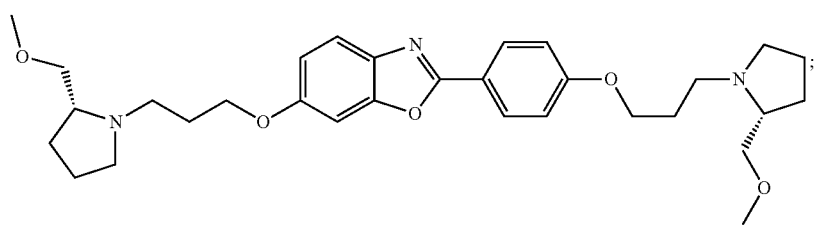
Compound 26
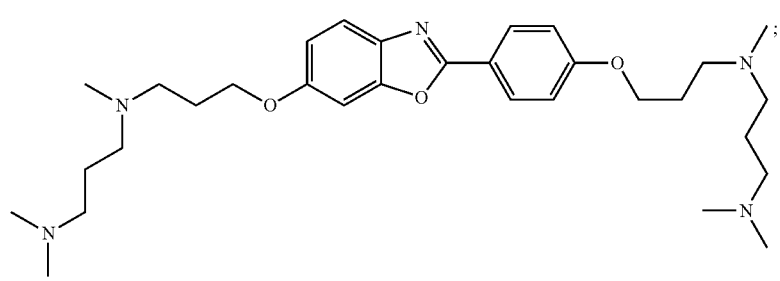
Compound 27
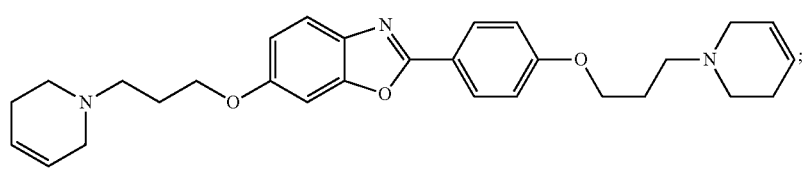
Compound 28
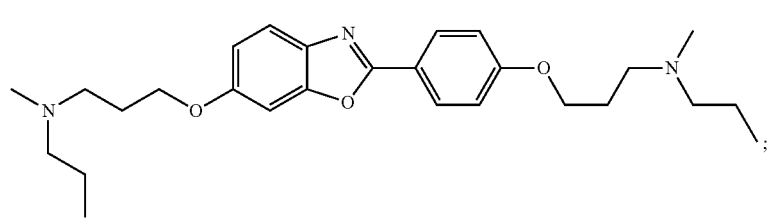
Compound 29
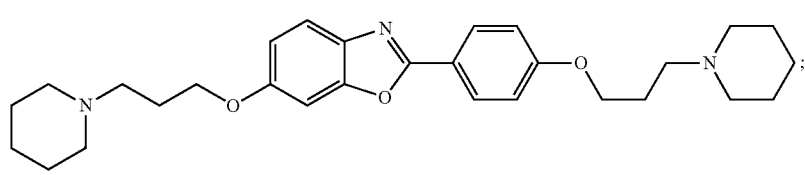
Compound 30
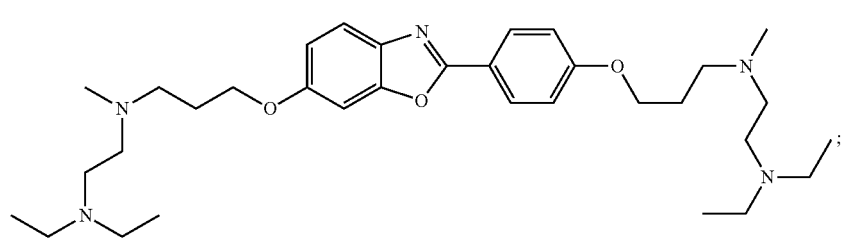
Compound 31
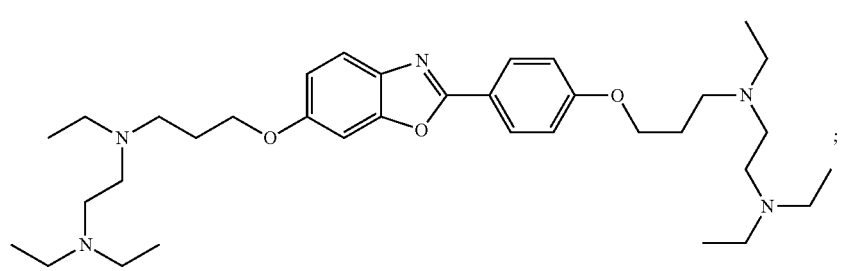
Compound 32

-continued

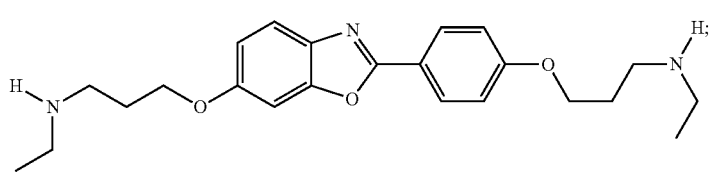

Compound 33

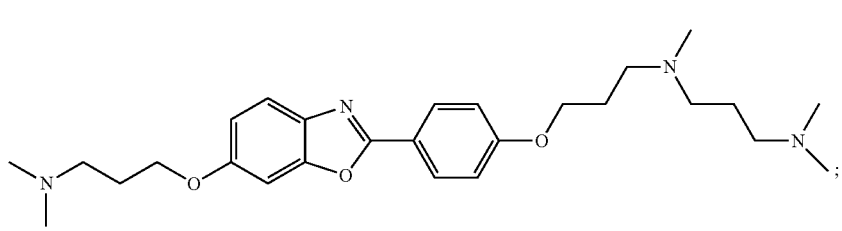

Compound 34

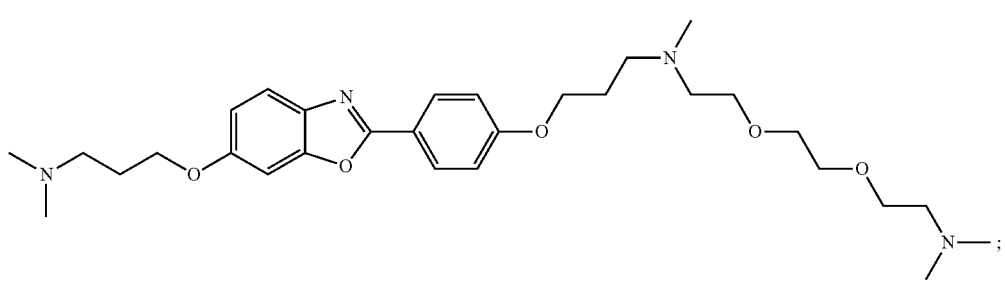

Compound 35

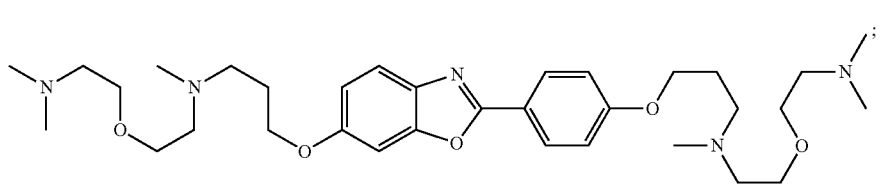

Compound 36

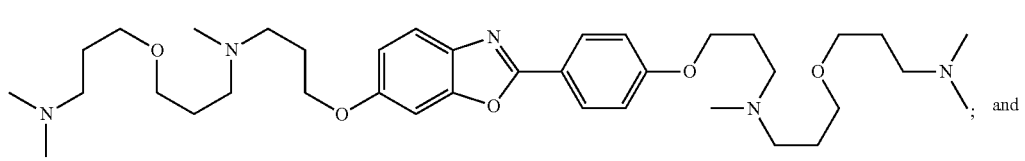

Compound 37

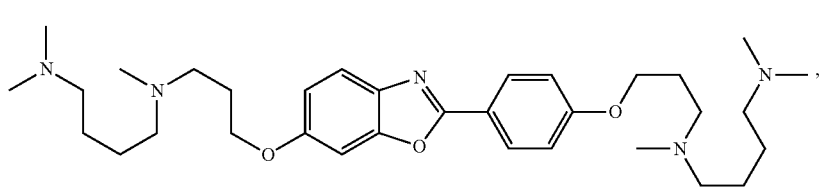

Compound 38 or a pharmaceutically acceptable salt thereof; and a pharmaceutically acceptable carrier.

15. A method of treating an immunological disorder selected from the group consisting of sepsis, lupus, rheumatoid arthritis and multiple sclerosis in a subject, comprising administering to the subject an effective amount of a compound selected from the group consisting of:

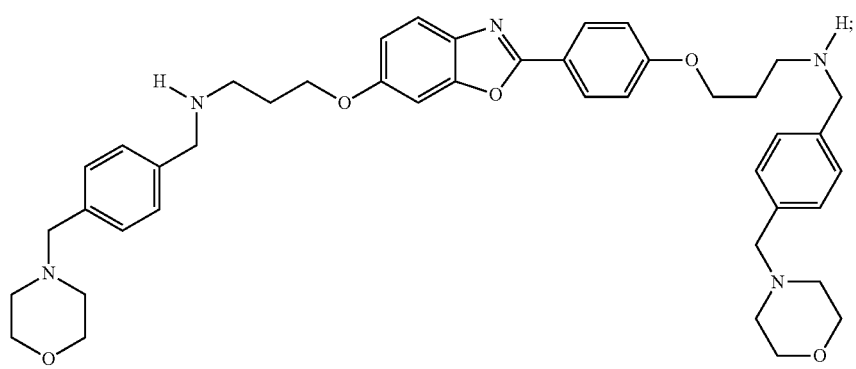
Compound 13
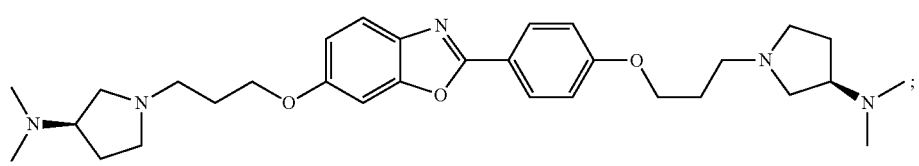
Compound 16
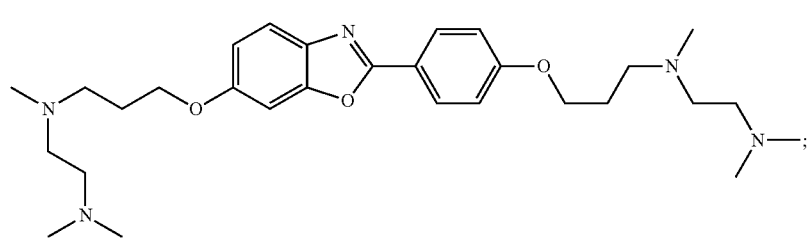
Compound 22
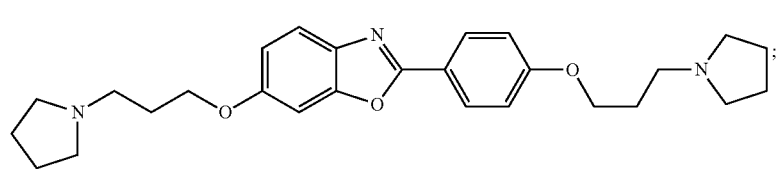
Compound 23
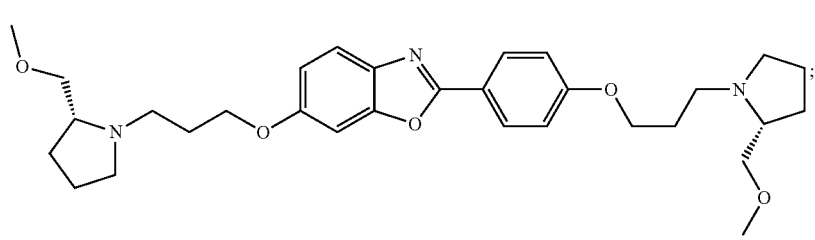
Compound 26
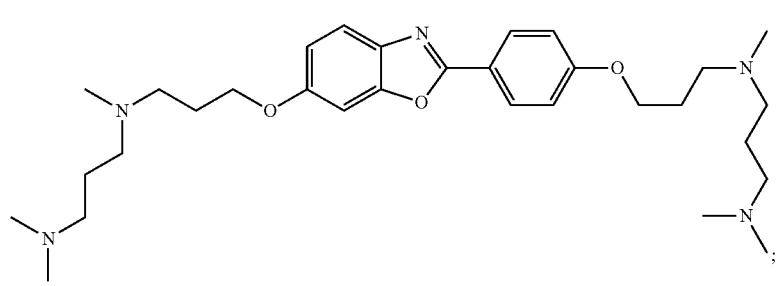
Compound 27
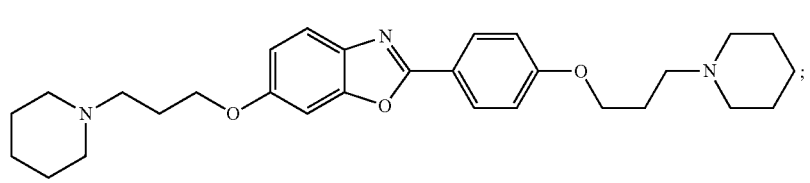
Compound 30

-continued

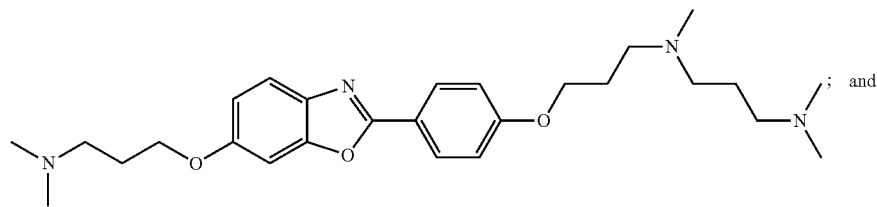

Compound 34

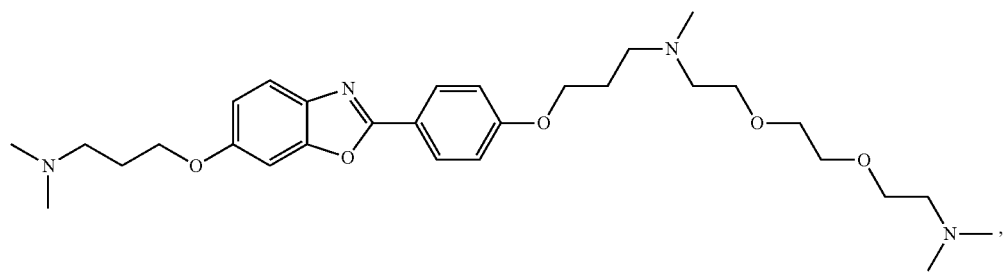

Compound 35 or a pharmaceutically acceptable salt thereof.

16. The method of claim 15, wherein the subject is human.

17. The method of claim 15, wherein the compound is selected from the group consisting of:

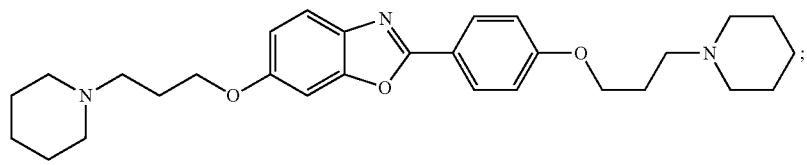

Compound 30

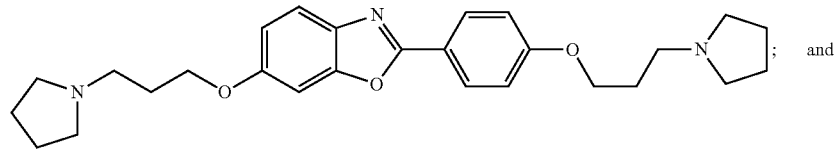

Compound 23

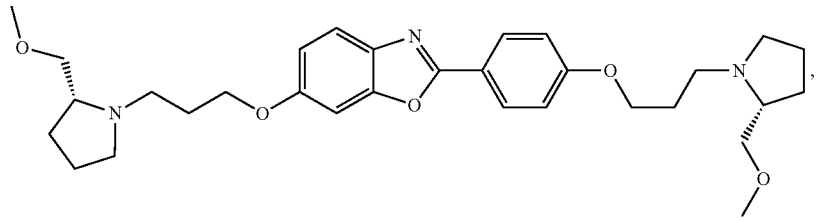

Compound 26 or a pharmaceutically acceptable salt thereof.

18. The method of claim 15, wherein the compound is

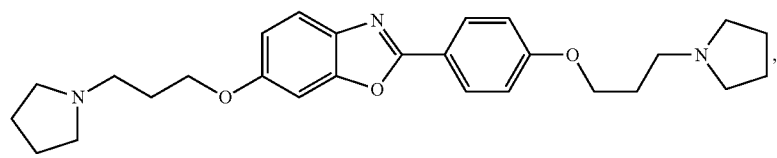

Compound 23 or a pharmaceutically acceptable salt thereof.

19. The method of claim 15, wherein the immunological disorder is sepsis.

20. The method of claim 15, wherein the immunological disorder is selected from the group consisting of lupus, rheumatoid arthritis and multiple sclerosis.

21. The method of claim 20, wherein the immunological disorder is lupus.

* * * * *

UNITED STATES PATENT AND TRADEMARK OFFICE
CERTIFICATE OF CORRECTION

PATENT NO. : 8,354,400 B2
APPLICATION NO. : 13/121012
DATED : January 15, 2013
INVENTOR(S) : Zheng et al.

It is certified that error appears in the above-identified patent and that said Letters Patent is hereby corrected as shown below:

On Title Page:
Item 73, Assignee: Please correct "Eisai R&D Co., Ltd. (JP)"
to read -- Eisai R&D Management Co., Ltd. (JP) --

In the Specification:
Column 2, Lines 47-48: Please correct "$(CH_2)_2$—O—$(CH_2)_2$—O—$(CH_2)_2N(CH_3)_2$,"
to read -- $(CH_2)_2O(CH_2)_2O(CH_2)_2N(CH_3)_2$, --

Column 2, Line 54: Please correct "$(CH_2)_p$—O—$(CH_2)_g N(CH_3)_2$,"
to read -- $(CH_2)_p O(CH_2)_q N(CH_3)_2$, --

Column 6, Line 17: Please correct "wherein $R^1$, $R^2$,"
to read -- wherein i, $R^1$, $R^2$, --

Column 6, Line 32: Please correct "a group of formula (g): a group of formula (h):"
to read -- a group of formula (g): --

Column 6, Line 42: Please insert the following, above item (h):
-- a group of formula (h): --

Column 6, Line 49: Please correct "a group of formula (i): a group of formula (j):"
to read -- a group of formula (i): --

Column 6, Line 60: Please insert the following, above item (j):
-- a group of formula (j): --

Column 7, Line 1: Please correct "a group of formula (k): a group of formula (m):"
to read -- a group of formula (k): --

Signed and Sealed this
Fourteenth Day of October, 2014

Michelle K. Lee
*Deputy Director of the United States Patent and Trademark Office*

CERTIFICATE OF CORRECTION (continued)
U.S. Pat. No. 8,354,400 B2

Column 7, Line 10: Please insert the following, above item (m):
-- a group of formula (m): --

Column 8, Lines 6-7: Please correct "$(CH_2)_2$—O—$(CH_2)_2$—O—$(CH_2)_2N(CH_3)_2$,"
to read -- $(CH_2)_2O(CH_2)_2O(CH_2)_2N(CH_3)_2$, --

Columns 19-20, Lines 40-50: Please correct to read

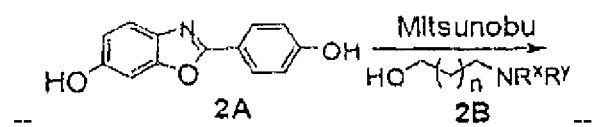

Column 21, Lines 15-22, Item 3D: Please correct

Column 21, Lines 33-38, Item 3G: Please correct

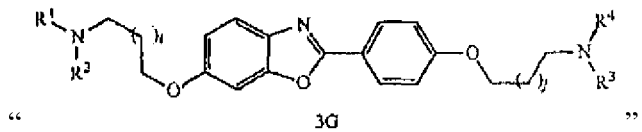

to read

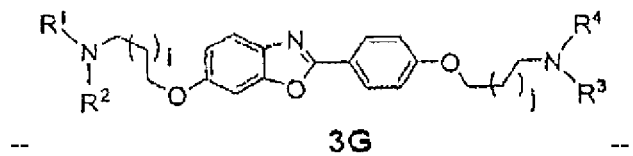

Column 21, Lines 44-45: Please correct "$(CH_2)_2$—O—$(CH_2)_2$—O—$(CH_2)_2N(CH_3)_2$."
to read -- $(CH_2)_2O(CH_2)_2O(CH_2)_2N(CH_3)_2$. --

In the Claims:
Column 56, Claim 4, Line 11:
Please correct "a group of formula (g): a group of formula (h):"
to read -- a group of formula (g): --

Column 56, Claim 4, Line 20: Please insert the following, above item (h):
-- a group of formula (h): --

CERTIFICATE OF CORRECTION (continued)
U.S. Pat. No. 8,354,400 B2

Column 56, Claim 4, Line 27:
Please correct "a group of formula (i): a group of formula (j):"
    to read -- a group of formula (i): --

Column 56, Claim 4, Line 36: Please insert the following, above item (j):
    -- a group of formula (j): --

Column 56, Claim 4, Line 43:
Please correct "a group of formula (k): a group of formula (m):"
    to read -- a group of formula (k): --

Column 56, Claim 4, Line 53: Please insert the following, above item (m):
    -- a group of formula (m): --

Column 62, Claim 10, Compound 8: Please correct the compound below:

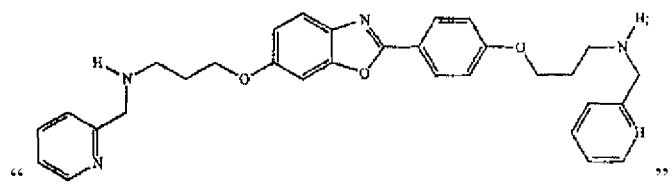

to read:

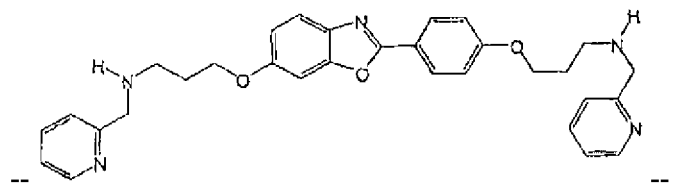

Columns 65 and 66, Claim 10, Compound 20: Please correct the compound below:

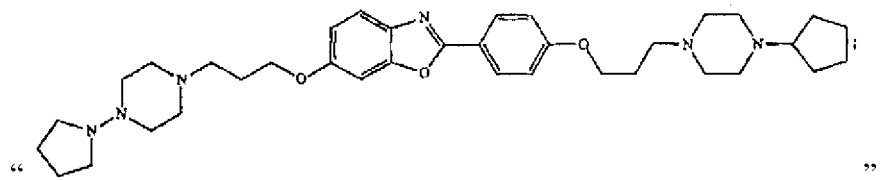

to read:

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial
<220> FEATURE:
<223> OTHER INFORMATION: Synthetic phosphorothioate oligonucleotide
<220> FEATURE:
<221> NAME/KEY: misc_feature
<222> LOCATION: (1)..(24)
<223> OTHER INFORMATION: Phosphorothioate linkage
```

```
<400> SEQUENCE: 1
tcgtcgtttt gtcgttttgt cgtt                                           24

<210> SEQ ID NO 2
<211> LENGTH: 20
<212> TYPE: DNA
<213> ORGANISM: Artificial
<220> FEATURE:
<223> OTHER INFORMATION: Synthetic phosphorothioate oligonucleotide
<220> FEATURE:
<221> NAME/KEY: misc_feature
<222> LOCATION: (1)..(20)
<223> OTHER INFORMATION: Phosphorothioate linkage

<400> SEQUENCE: 2
tccatgacgt tcctgatgct                                                20

<210> SEQ ID NO 3
<211> LENGTH: 20
<212> TYPE: DNA
<213> ORGANISM: Artificial
<220> FEATURE:
<223> OTHER INFORMATION: Synthetic phosphorothioate/phosphodiester
      oligonucleotide
<220> FEATURE:
<221> NAME/KEY: misc_feature
<222> LOCATION: (1)..(2)
<223> OTHER INFORMATION: Phophorothioate linkage
<220> FEATURE:
<221> NAME/KEY: misc_feature
<222> LOCATION: (15)..(19)
<223> OTHER INFORMATION: Phophorothioate linkage

<400> SEQUENCE: 3
gggggacgat cgtcgggggg                                                20

<210> SEQ ID NO 4
<211> LENGTH: 21
<212> TYPE: PRT
<213> ORGANISM: Artificial
<220> FEATURE:
<223> OTHER INFORMATION: Synthetic polypeptide

<400> SEQUENCE: 4

Met Glu Val Gly Trp Tyr Arg Ser Pro Phe Ser Arg Val Val His Leu
1               5                   10                  15

Tyr Arg Asn Gly Lys
            20
```